(12) United States Patent
Meller et al.

(10) Patent No.: US 12,168,265 B2
(45) Date of Patent: Dec. 17, 2024

(54) NANOPORE FABRICATION

(71) Applicant: TECHNION RESEARCH & DEVELOPMENT FOUNDATION LIMITED, Haifa (IL)

(72) Inventors: Amit Meller, Haifa (IL); Tal Gilboa, Haifa (IL); Adam Zrehen, Haifa (IL); Arik Girsault, Haifa (IL); Eran Zvuloni, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 397 days.

(21) Appl. No.: 17/482,904

(22) Filed: Sep. 23, 2021

(65) Prior Publication Data

US 2022/0009034 A1     Jan. 13, 2022

Related U.S. Application Data

(63) Continuation-in-part of application No. PCT/IL2020/050356, filed on Mar. 25, 2020.

(60) Provisional application No. 63/217,368, filed on Jul. 1, 2021, provisional application No. 62/823,065, filed on Mar. 25, 2019.

(51) Int. Cl.
| | |
|---|---|
| *B23K 26/36* | (2014.01) |
| *B01D 71/02* | (2006.01) |
| *B23K 26/362* | (2014.01) |
| *G01B 11/06* | (2006.01) |
| *G01N 33/487* | (2006.01) |

(52) U.S. Cl.
CPC .......... *B23K 26/36* (2013.01); *B01D 71/0215* (2022.08); *B23K 26/362* (2013.01); *G01B 11/06* (2013.01); *G01N 33/48721* (2013.01); *B01D 2325/0283* (2022.08)

(58) Field of Classification Search
CPC ...... B23K 26/36; B23K 26/362; G01B 11/06; G01N 33/48721
See application file for complete search history.

(56) References Cited

U.S. PATENT DOCUMENTS

2018/0043310 A1    2/2018   Bustamante

FOREIGN PATENT DOCUMENTS

| WO | 2014153047 A1 | 9/2014 |
|---|---|---|
| WO | 2016135656 A1 | 9/2016 |

OTHER PUBLICATIONS

Yanwen Yuan, Sub-20 nm Nanopores Sculptured by a Single Nanosecond Laser Pulse, 2018, arXiv, arXiv:1806.08172 (Year: 2018).*

(Continued)

*Primary Examiner* — Janie M Loeppke
*Assistant Examiner* — Theodore J Evangelista
(74) *Attorney, Agent, or Firm* — The Roy Gross Law Firm, LLC; Roy Gross

(57) ABSTRACT

Systems comprising a light source, thin membrane immersed in an aqueous solution and a system to direct and focus light from the light source to a spot on the membrane are provided. Methods of thinning and etching a membrane are also provided, as are membranes comprising a nanopore with a Gaussian curve shaped cross-section.

17 Claims, 59 Drawing Sheets
(38 of 59 Drawing Sheet(s) Filed in Color)

(56) References Cited

OTHER PUBLICATIONS

Tal Gilboa, Optically-Monitored Nanopore Fabrication Using a Focused Laser Beam, Jun. 27, 2018, Scientific Reports, vol. 8 Issue 1 (Year: 2018).*

Dela Torre R, Larkin J, Singer A, Meller A. Fabrication and characterization of solid-state nanopore arrays for high-throughput DNA sequencing. Nanotechnology. Sep. 28, 2012;23(38):385308. doi: 10.1088/0957-4484/23/38/385308. Epub Sep. 5, 2012. PMID: 22948520; PMCID: PMC3557807.

Mohammadamir Ghaderi and Reinoud F. Wolffenbuttel. Design and fabrication of ultrathin silicon-nitride membranes for use in UV-visible airgap-based MEMS optical filters. 2016 J. Phys.: Conf. Ser. 757 012032; doi:10.1088/1742-6596/757/1/012032.

Gilboa T, Zrehen A, Girsault A, Meller A. Optically-Monitored Nanopore Fabrication Using a Focused Laser Beam. Sci Rep. Jun. 27, 2018;8(1):9765. doi: 10.1038/s41598-018-28136-z. PMID: 29950607; PMCID: PMC6021433. DOI:10.1038/s41598-018-28136-z.

Meng-Yue Wu, Diego Krapf, Mathijs Zandbergen, and Henny Zandbergen. Formation of nanopores in a SiN/SiO2 membrane with an electron beam, Appl. Phys. Lett. 87, 113106 (2005) https://doi.org/10.1063/1.2043247.

Yuan, Y. et al.(2018). Sub-20 nm nanopores sculptured by a single nanosecond laser pulse. arXiv preprint arXiv:1806.08172.

Wang R, Gilboa T, Song J, Huttner D, Grinstaff MW, Meller A. Single-Molecule Discrimination of Labeled DNAs and Polypeptides Using Photoluminescent-Free TiO2 Nanopores. ACS Nano. Nov. 27, 2018;12(11):11648-11656. doi: 10.1021/acsnano.8b07055. Epub Nov. 1, 2018. PMID: 30372037.

Park J, Heo S, Chung JG, Kim H, Lee H, Kim K, Park GS. Bandgap measurement of thin dielectric films using monochromated STEM-EELS. Ultramicroscopy. Aug. 2009;109(9):1183-8. doi: 10.1016/j.ultramic.2009.04.005. Epub May 13, 2009. PMID: 19515492.

Assad ON, Di Fiori N, Squires AH, Meller A. Two color DNA barcode detection in photoluminescence suppressed silicon nitride nanopores. Nano Lett. Jan. 14, 2015;15(1):745-52. doi: 10.1021/nl504459c. Epub Dec. 22, 2014. PMID: 25522780; PMCID: PMC4296929.

Yamazaki, H., Kimura, S., Tsukahara, M. et al. Optical detection of DNA translocation through silicon nanopore by ultraviolet light. Appl. Phys. A 115, 53-56 (2014). https://doi.org/10.1007/s00339-013-7956-0.

Sawafta F, Clancy B, Carlsen AT, Huber M, Hall AR. Solid-state nanopores and nanopore arrays optimized for optical detection. Nanoscale. Jun. 21, 2014;6(12):6991-6. doi: 10.1039/c4nr00305e. PMID: 24838772.

Gilboa T, Torfstein C, Juhasz M, Grunwald A, Ebenstein Y, Weinhold E, Meller A. Single-Molecule DNA Methylation Quantification Using Electro-optical Sensing in Solid-State Nanopores. ACS Nano. Sep. 27, 2016;10(9):8861-70. doi: 10.1021/acsnano.6b04748. Epub Sep. 2, 2016. PMID: 27580095.

Kim, M., Wanunu, M., Bell, D. and Meller, A. (2006), Rapid Fabrication of Uniformly Sized Nanopores and Nanopore Arrays for Parallel DNA Analysis. Adv. Mater., 18: 3149-3153. https://doi.org/10.1002/adma.200601191.

Kim, M. J., McNally, B., Murata, K., & Meller, A. (2007). Characteristics of solid-state nanometre pores fabricated using a transmission electron microscope. Nanotechnology, 18(20), 205302. https://doi.org/10.1088/0957-4484/18/20/205302.

Lo, C. J., Aref, T., & Bezryadin, A. (2006). Fabrication of symmetric sub-5 nm nanopores using focused ion and electron beams. Nanotechnology, 17(13), 3264-3267. doi:10.1088/0957-4484/17/13/031.

Storm AJ, Chen JH, Ling XS, Zandbergen HW, Dekker C. Fabrication of solid-state nanopores with single-nanometre precision. Nat Mater. Aug. 2003;2(8):537-40. doi: 10.1038/nmat941. PMID: 12858166.

Kwok H, Briggs K, Tabard-Cossa V. Nanopore fabrication by controlled dielectric breakdown. PLoS One. Mar. 21, 2014;9(3):e92880. doi: 10.1371/journal.pone.0092880. PMID: 24658537; PMCID: PMC3962464.

Zrehen A, Gilboa T, Meller A. Real-time visualization and sub-diffraction limit localization of nanometer-scale pore formation by dielectric breakdown. Nanoscale. Nov. 2, 2017;9(42):16437-16445. doi: 10.1039/c7nr02629c. PMID: 29058736.

M. L. Ngan, K. C. Lee, and K. W. Cheah, "High power density laser etching of silicon", Journal of Applied Physics 83, 1637-1641 (1998) https://doi.org/10.1063/1.366877.

Houle, F.A. Basic mechanisms in laser etching and deposition. Appl. Phys. A 41, 315-330 (1986). https://doi.org/10.1007/BF00616055.

Choy, C.H., Cheah, K.W. Laser-induced etching of silicon. Appl. Phys. A 61, 45-50 (1995). https://doi.org/10.1007/BF01538209.

Briggs, K., Kwok, H. and Tabard-Cossa, V. (2014), Automated Fabrication of 2-nm Solid-State Nanopores for Nucleic Acid Analysis. Small, 10: 2077-2086. https://doi.org/10.1002/smll.201303602.

Itaru Yanagi, Koji Fujisaki, Hirotaka Hamamura, and Ken-ichi Takeda, "Thickness-dependent dielectric breakdown and nanopore creation on sub-10-nm-thick SiN membranes in solution", Journal of Applied Physics 121, 045301 (2017) https://doi.org/10.1063/1.4974286.

Healy K, Ray V, Willis LJ, Peterman N, Bartel J, Drndic M. Fabrication and characterization of nanopores with insulated transverse nanoelectrodes for DNA sensing in salt solution. Electrophoresis. Dec. 2012;33(23):3488-96. doi: 10.1002/elps.201200350. PMID: 23161707; PMCID: PMC3828733.

Xia D, Huynh C, McVey S, Kobler A, Stern L, Yuan Z, Ling XS. Rapid fabrication of solid-state nanopores with high reproducibility over a large area using a helium ion microscope. Nanoscale. Mar. 15, 2018;10(11):5198-5204. doi: 10.1039/c7nr08406d. PMID: 29493685.

Verschueren DV, Yang W, Dekker C. Lithography-based fabrication of nanopore arrays in freestanding SiN and graphene membranes. Nanotechnology. Apr. 6, 2018;29(14):145302. doi: 10.1088/1361-6528/aaabce. PMID: 29384130; PMCID: PMC5997186.

Yanagi I, Akahori R, Takeda KI. Stable fabrication of a large nanopore by controlled dielectric breakdown in a high-pH solution for the detection of various-sized molecules. Sci Rep. Sep. 11, 2019;9(1):13143. doi: 10.1038/s41598-019-49622-y. PMID: 31511597; PMCID: PMC6739384.

Ying C, Houghtaling J, Eggenberger OM, Guha A, Nirmalraj P, Awasthi S, Tian J, Mayer M. Formation of Single Nanopores with Diameters of 20-50 nm in Silicon Nitride Membranes Using Laser-Assisted Controlled Breakdown. ACS Nano. Nov. 27, 2018;12(11):11458-11470. doi: 10.1021/acsnano.8b06489. Epub Oct. 24, 2018. PMID: 30335956.

Yamazaki H, Hu R, Zhao Q, Wanunu M. Photothermally Assisted Thinning of Silicon Nitride Membranes for Ultrathin Asymmetric Nanopores. ACS Nano. Dec. 26, 2018;12(12):12472-12481. doi: 10.1021/acsnano.8b06805. Epub Nov. 30, 2018. PMID: 30457833.

Yanagi I, Hamamura H, Akahori R, Takeda KI. Two-step breakdown of a SiN membrane for nanopore fabrication: Formation of thin portion and penetration. Sci Rep. Jul. 4, 2018;8(1):10129. doi: 10.1038/s41598-018-28524-5. PMID: 29973672; PMCID: PMC6031669.

Gilboa, T. et al. (2019). Automated, ultra-fast laser-drilling of nanometer scale pores and nanopore arrays in aqueous solutions. (Manuscript). Published paper available online in in Advanced Functional Materials, vol. 30 (18), May 4, 2020; https://doi.org/10.1002/adfm.201900642.

PCT International Search Report for International Application No. PCT/IL2020/050356, mailed Jul. 21, 2020, 4pp.

PCT Written Opinion for International Application No. PCT/IL2020/050356, mailed Jul. 21, 2020, 9pp.

* cited by examiner 300 mV 450 mV 600 mV

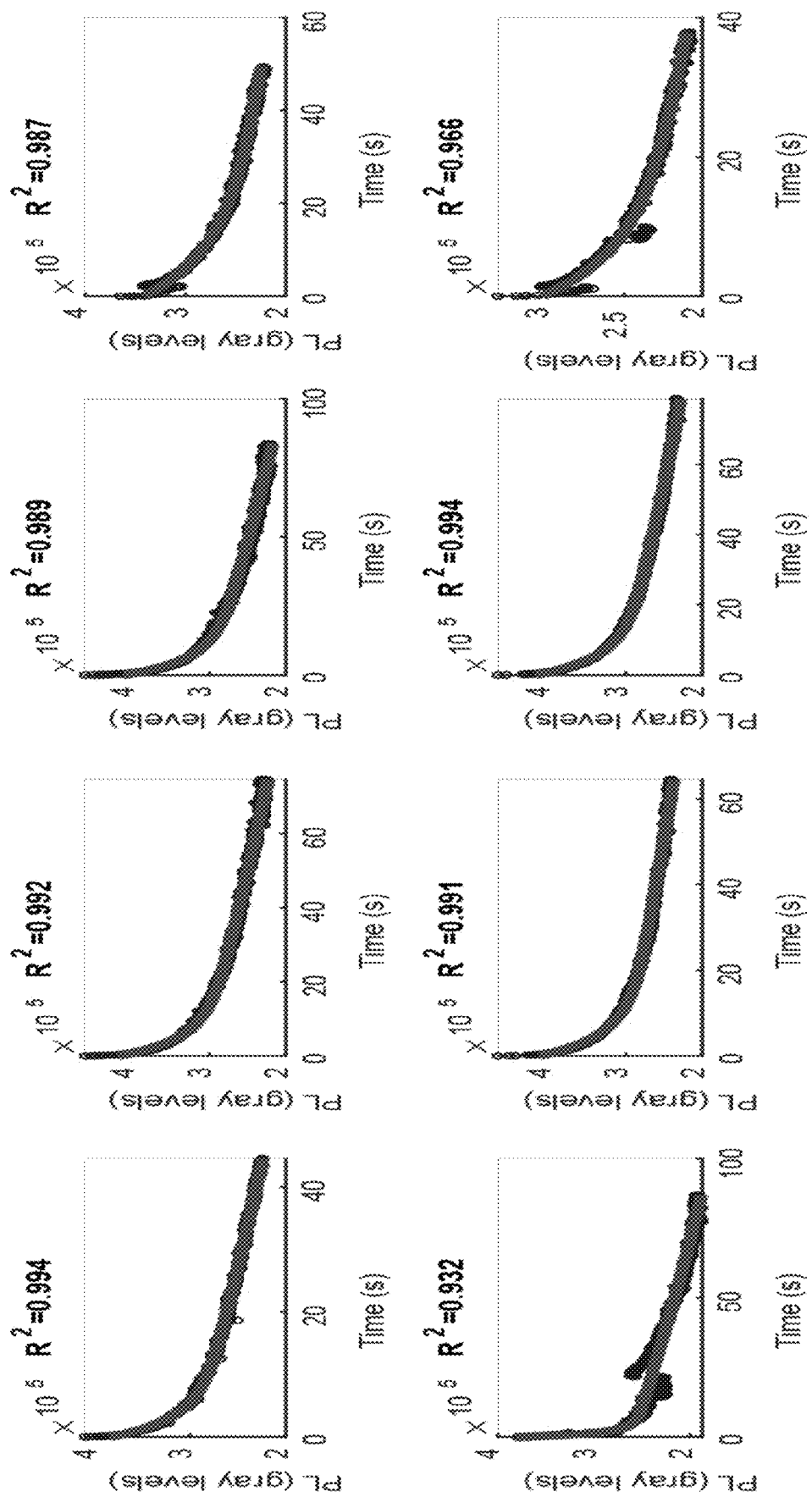
Figure 28 continued_1

Figure 28 continued_2
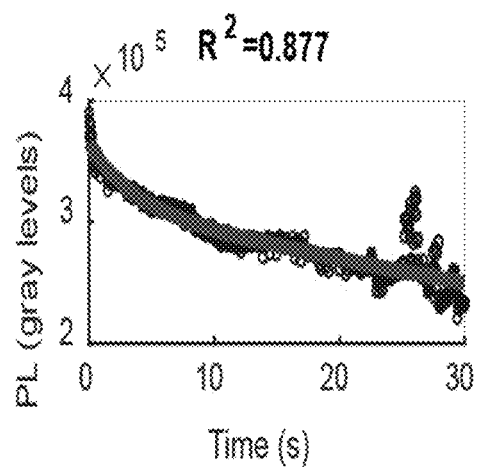
Figure 29A
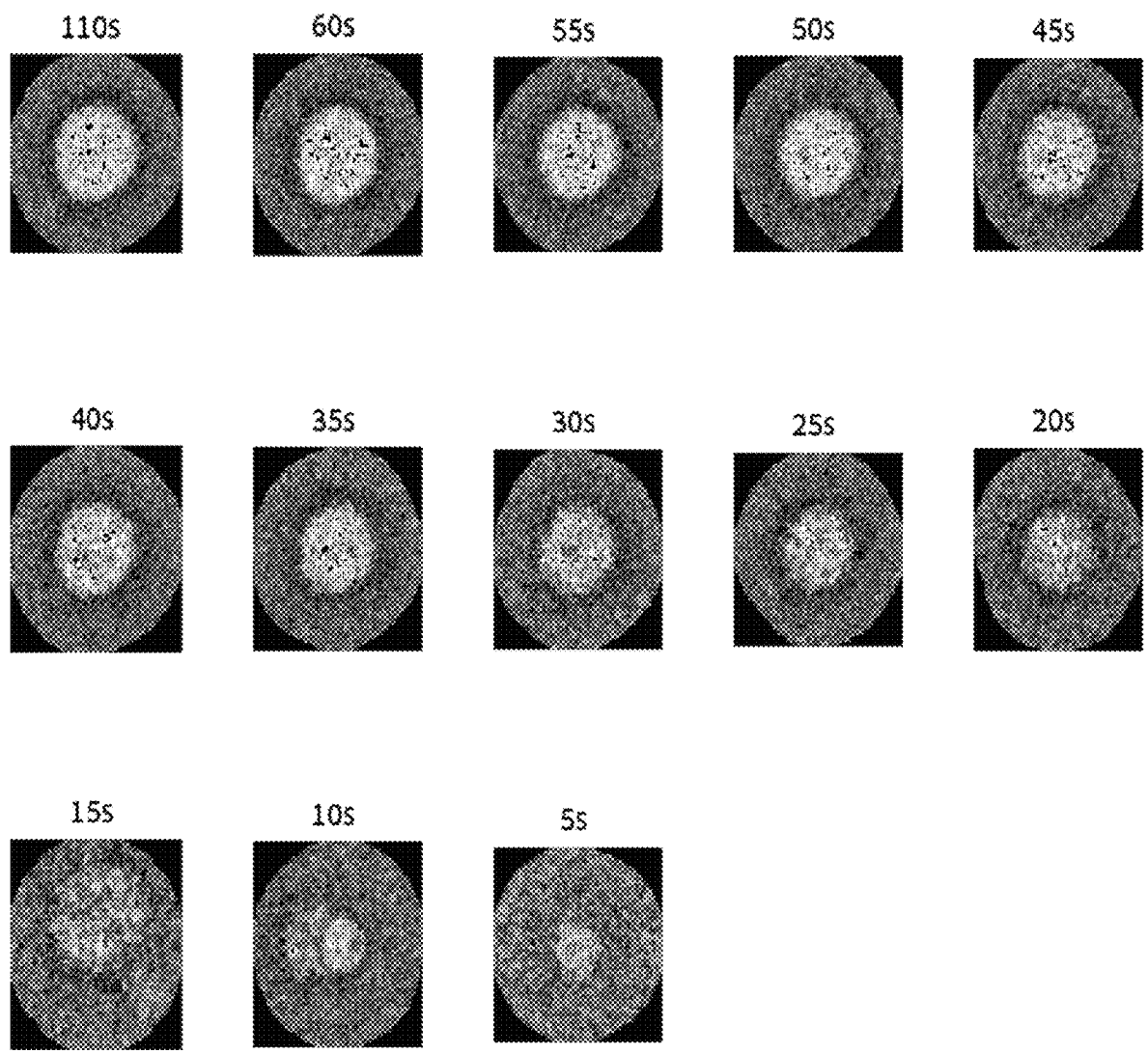

NANOPORE FABRICATION

CROSS REFERENCE TO RELATED APPLICATIONS

This application is a continuation-in-part (CIP) of PCT Application No. PCT/IL2020/050356 having International filing date of Mar. 25, 2020, entitled "NANOPORE FABRICATION", which claims the benefit of priority of U.S. Provisional Patent Application No. 62/823,065, filed on Mar. 25, 2019.

This application also claims the benefit of priority of U.S. Provisional Patent Application No. 63/217,368, filed on Jul. 1, 2021, entitled "NANOPORE FABRICATION". The contents of which are hereby incorporated by reference in their entirety.

FIELD OF INVENTION

The present invention is in the field of nanopore fabrication.

BACKGROUND OF THE INVENTION

The development of synthetic solid-state nanopores (ssNPs) as a substitute for biological channels remains a major focus in nanotechnology given their greater flexibility in terms of size, shape, surface properties, and cross-device compatibility. While traditionally the principal mode of single-molecule detection was based on ionic resistive pulsing measurements, a rapidly growing trend in the nanopore community has been towards "electro-optical" sensing. The simultaneous measurement of the electrical (ion current) and fluorescence signal (photon emission) extends the scope of biomolecular targets for nanopores and opens up new applications since both multiple fluorophore colors and varying photon intensities can be acquired to obtain specific information on the molecule of interest. Specifically, by selective fluorescent labelling of the analyte of interest, researchers have shown that ssNPs can be applied to DNA sequencing, DNA barcoding, epigenetic modification analysis (for example, DNA methylation quantification) and polypeptide discrimination. Although superior to strictly electrical sensing with respect to the amount of encodable information, electro-optical sensing brings its own set of fabrication challenges. Nanopores must be prepared in a way such that their position can be readily identified in situ. Furthermore, the peripheral structure heavily impacts the background noise and fluorescent signal of a translocating molecule.

In the first decade of nanopore sensing, the controlled focusing of an ion or electron beam, as by transmission electron microscopy (TEM), was the only practical method for forming ssNPs with nanometric dimensions. As these methods utilized high vacuum during pore drilling, it followed that they were inherently slow, expensive, and importantly, produced un-hydrated surfaces that must be further treated to permit water passage and subsequent resistive pulse sensing. More recently, controlled dielectric breakdown (CBD) emerged as a powerful, low-cost alternative to TEM because it could create nanopores in freestanding silicon nitride ($SiN_x$) directly in solution and could be almost fully automated. CBD, which uses an applied voltage to induce randomly accumulating material defects, is nonetheless comparatively less flexible and efficient at localizing nanopore formation. Recent attempts to do so relied on the principle that nanopores preferentially form at the hotspot of an infrared (IR) laser or at the thinnest membrane cross-section. Thus, in the latter case, milling or lithographic steps were implemented upstream of CBD as a preparatory step to direct nanopore formation. Using an IR laser, on the other hand, was complicated by the need to simultaneously control the applied voltage and laser power, as the IR laser only enhanced the local DC field necessary for dielectric breakdown and did not independently form nanopores. Fast, highly-reproducible, in situ methods of fabricating nanopores and nanopore arrays are greatly needed.

SUMMARY OF THE INVENTION

The present invention provides systems comprising a light source, a membrane and a system to direct and focus light from the light source to a spot on the membrane. Methods of light-induced thinning and etching a membrane and generating a nanopore in a membrane are also provided. Membranes comprising a nanopore with a Gaussian curve shaped cross-section are provided as well.

According to a first aspect, there is provided a method of thinning a membrane comprising a first layer comprising an index of refraction of greater than 2.0, the method comprising shining focused light on a spot on the first layer, thereby thinning the membrane.

According to another aspect, there is provided a method of thinning a membrane, the method comprising shining pulsed laser light on a spot on the membrane, thereby thinning the membrane.

According to some embodiments, the focused light is laser light and the laser light is at a wavelength of between 300 and 600 nm.

According to some embodiments, the pulsed laser light is at a wavelength of between 300 and 600 nm.

According to some embodiments, the focused light is within the purple, blue or green spectrum.

According to some embodiments, the light comprises an intensity of at least 100 µW.

The method of the invention, wherein the light comprises an intensity of between 1 and 45 mW.

According to some embodiments, the laser light is continuous-wave laser light or pulsed laser light.

According to some embodiments, the membrane comprises a first layer comprising an index of refraction of greater than 2.0.

According to some embodiments, the index of refraction is greater than 2.20.

According to some embodiments, the first layer comprises silicon nitride (SiNx).

According to some embodiments, the first layer is a SiNx layer comprising an average silicon to nitrogen ratio of greater than 0.75.

According to some embodiments, the average silicon to nitrogen ratio is greater than 0.8.

According to some embodiments, the membrane is a freely standing membrane, covered by an aqueous solution on both sides.

According to some embodiments, the membrane comprises a second layer refractory to thinning by the focused light when not layered on the first layer, wherein the second layer is a dielectric layer or a layer of metal oxide, and wherein the second layer is layered onto the first layer.

According to some embodiments, the second layer is a layer of metal oxide and wherein the metal oxide is titanium oxide (TiO2), aluminum oxide (AlO2) or hafnium oxide (HfO2).

According to some embodiments, the membrane does not comprise a thickness of less than 20 nm.

According to some embodiments, the membrane comprises a thickness of less than 20 nm.

According to some embodiments, the membrane is immersed in ultrapure water or salt buffer comprising an alkaline pH.

According to some embodiments, the membrane is at room temperature and pressure.

According to some embodiments, the method further comprises measuring photoluminescent (PL) intensity from the spot on the membrane.

According to some embodiments, the PL intensity is inversely proportional to the thickness of the spot on the membrane, and the thinning is halted at a desired thickness based on a measured PL intensity.

According to some embodiments, the thinning comprises forming a pore through the membrane.

According to some embodiments, the pore is a nanopore.

According to some embodiments, the membrane is covered in an aqueous solution and the method further comprising measuring ionic current through the membrane; optionally, wherein an increase in ionic current through the membrane indicates the pore has been formed in the membrane.

According to some embodiments, the spot in the membrane comprises a thickness of at least 40 nm before the shining and the pore can be produced though the spot in the membrane in less than 20 seconds.

According to some embodiments, the thinning comprises widening a pore through the membrane.

According to some embodiments, the membrane is covered in an aqueous solution and an increase in ionic current through the membrane is proportional to a widening of the pore.

According to some embodiments, the method is for producing a pore of a given diameter, wherein the focused light is automatically shut off at a predetermined current.

According to another aspect, there is provided a system comprising:
 a. a light source;
 b. a membrane comprising a first layer comprising an index of refraction of greater than 2.0;
 c. an apparatus to direct and focus light from the light source to a spot on the layer.

According to some embodiments, the membrane is in an optically accessible flow cell.

According to some embodiments, the membrane is a freely standing membrane, covered by an aqueous solution on both sides.

According to some embodiments, the index of refraction is greater than 2.20.

According to some embodiments, the system further comprises a photodetector, wherein the photodetector:
 a. is capable of measuring low light intensities and/or measuring at high temporal resolution;
 b. is an avalanche photodiode, a photo-multiplier tube or a CMOS camera; or
 c. is configured to detect emissions from the spot on the membrane.

According to some embodiments, the light source is at least one of:
 a. a solid-state or gas lasers configured to emit within the purple, blue or green spectrum;
 b. a solid-state laser configured to emit at between 300-600 nanometers (nm);
 c. a continuous-wave laser or a pulsed laser;
 d. configured to produce light at an intensity of at least 100 micro-watts ($\mu W$) at the spot on the membrane; and
 e. configured to produce light at an intensity of at least 1 milliwatts (mW) at the spot on the membrane.

According to some embodiments, the system further comprises an imaging sensor, optionally, wherein the imaging sensor is selected from an electron multiplying CCD camera, a CMOS camera and a sCMOS camera.

According to some embodiments, the first layer comprises SiNx and comprises a silicon to nitrogen ratio of greater than 0.75.

According to some embodiments, the silicon to nitrogen ratio is greater than 0.80.

According to some embodiments, the membrane does not comprise a thickness of less than 20 nm, comprises a thickness of less than 20 nm, is at room temperature and pressure, or a combination thereof.

According to some embodiments, the membrane is immersed in ultrapure water or salt buffer at an alkaline pH.

According to some embodiments, the system further comprises two electrodes and an apparatus configured to pass an electric current between the two electrodes, wherein one electrode is positioned on one side of the membrane and a second electrode is positioned on another side of the membrane, optionally, further comprising a current detector configured to measure current between the two electrodes.

According to some embodiments, the membrane further comprises a second layer layered on the first layer, wherein the second layer is a dielectric layer or a layer of metal oxide, optionally wherein the metal oxide is TiO2, AlO2, or HfO2.

According to another aspect, there is provided a thinned membrane produced by a method of the invention.

According to another aspect, there is provided a membrane comprising a nanopore, wherein the membrane comprises a first layer comprising an index of refraction of greater than 2.0 and wherein the nanopore comprises a varying diameter and a Gaussian curve shaped cross-section.

According to some embodiments, the index of refraction is greater than 2.20.

According to some embodiments, the nanopore increases in diameter from one side of the membrane to the other, and wherein the increasing diameter follows a Gaussian curve.

According to some embodiments, the membrane produces a lower optical background at the nanopore than a nanopore in the membrane without a Gaussian curve shaped cross-section or not produced by a method of the invention.

According to some embodiments, the first layer comprises SiNx and wherein the SiNx comprises a silicon to nitrogen ratio of greater than 0.75.

According to some embodiments, the silicon to nitrogen ratio is greater than 0.8.

According to some embodiments, the membrane further comprises a second layer layered on the first layer, wherein the second layer is a dielectric layer or a layer of metal oxide, optionally wherein the metal oxide is TiO2, AlO2 or HfO2.

According to some embodiments, the nanopore comprises a first Gaussian curve shaped cross-section increasing in diameter from an interface of the first layer with the second layer to an exposed surface of the first layer and a second Gaussian curve shaped cross-section increasing in diameter from the interface to an exposed surface of the second layer.

According to some embodiments, the membrane comprises at least two layers with different indexes of refraction.

According to another aspect, there is provided a method of generating a nanopore of a predetermined size in a membrane, the method comprising:

a. shining a laser light on a spot on the membrane while monitoring ion current from a first side of the membrane to a second side of the membrane;
b. stopping the laser light when the ion current begins increasing thereby generating a pore through the membrane;
c. shining a laser light on the pore for a first duration and at a first intensity;
d. stopping the laser light and measuring at least one of electrical resistance and current through the pore;
e. shining a laser light on the pore for a second duration and at a second intensity wherein the second duration and second intensity are based on the measured at least one of electrical resistance and current;
f. repeating steps d and e until the measured electrical resistance and/or current indicates the pore is at the predetermined size;

thereby generating a nanopore of a predetermined size.

According to another aspect, there is provided a method of generating a nanopore of a predetermined size in a membrane, the method comprising:

a. shining a continuous wave focused laser light on a spot on the membrane while monitoring ion current from a first side of the membrane to a second side of the membrane;
b. stopping the continuous wave focused laser light when the ion current begins increasing thereby generating a pore through the membrane; and
c. shining pulsed laser light on the pore until the pore reaches the predetermined size;

thereby generating a nanopore of a predetermined size.

According to some embodiments, the method comprises measuring electrical resistance and/or current through the pore between pulses of the pulsed laser light.

According to some embodiments, the method comprises stopping shining the pulsed laser light when the measured electrical resistance and/or current indicates the pore is at the predetermined size.

According to some embodiments, the shining pulsed laser light comprises:

i. shining a laser light on the pore for a first duration and at a first intensity;
ii. stopping the laser light and measuring electrical resistance and/or current through the pore;
iii. shining a laser light on the pore for a second duration and at a second intensity wherein the second duration and second intensity are based on the measured electrical resistance and/or current;
iv. repeating steps d and e until the measured electrical resistance and/or current indicates the pore is at the predetermined size.

According to some embodiments, the laser light, the pulsed laser light or both are at a wavelength of between 300 and 600 nm.

According to some embodiments, the laser light is at a wavelength of about 405 nm.

According to some embodiments, the light comprises an intensity of between 1 and 45 mW.

According to some embodiments, the membrane comprises a first layer comprising an index of refraction of greater than 2.0.

According to some embodiments, the index of refraction is greater than 2.20.

According to some embodiments, the first layer comprises silicon nitride (SiNx).

According to some embodiments, the first layer is a SiNx layer comprising an average silicon to nitrogen ratio of greater than 0.75.

According to some embodiments, the average silicon to nitrogen ratio is greater than 0.8.

According to some embodiments, the membrane is a freely standing membrane, covered by an aqueous solution on both sides.

According to some embodiments, the membrane comprises a second layer refractory to thinning by the focused laser light when not layered on the first layer, wherein the second layer is a dielectric layer or a layer of metal oxide, and wherein the second layer is layered onto the first layer.

According to some embodiments, the second layer is a layer of metal oxide and wherein the metal oxide is titanium oxide (TiO2), aluminum oxide (AlO2) or hafnium oxide (HfO2).

According to some embodiments, the membrane is immersed in ultrapure water or salt buffer comprising an alkaline pH.

According to some embodiments, the method comprises stopping the laser light when the change in ion current increase is above a predetermined threshold.

According to some embodiments, the threshold is 4 nA/s.

According to some embodiments, the measuring electrical resistance through the pore is performed while the laser light is not shining.

According to some embodiments, the measuring is performed at a time point after the laser light is turned off sufficient to allow ionic current through the pore to stabilize.

According to some embodiments, the first duration is about 100 milliseconds.

According to some embodiments, the second intensity, the second duration or both are increased as compared to the first intensity if the measured electrical current indicates an effectiveness ratio above a predetermined threshold and wherein the effectiveness ratio is determined by $$\frac{\mu^{N-1}}{I_N}$$

wherein $\mu^{N-1}$ is the mean current of previous measurements and $I_N$ is the measured electrical current.

According to some embodiments, the mean current of previous measurements is of all previous measurements since a last measurement that produced an effectiveness ratio at or below the predetermined threshold.

According to some embodiments, the effectiveness ratio predetermined threshold is about 0.8.

According to some embodiments, the duration is increased geometrically based on the number of consecutive measurements that produced an effectiveness ratio above the predetermined threshold.

According to some embodiments, the intensity is increased linearly based on the number of consecutive measurements that produced an effectiveness ratio above the predetermined threshold.

According to some embodiments, the second intensity and the second duration are the same as the first intensity and the first duration if the effectiveness ratio is at or below the predetermined threshold, but a significance parameter is at or below a predetermined threshold, wherein the significance parameter is $I_N - \mu^{N-1}$.

According to some embodiments, the significance parameter predetermined threshold is 1 nA.

According to some embodiments, the second intensity, the second duration or both are decreased as compared to the first intensity if the measured electrical current indicates the effectiveness ratio is at or below a predetermined threshold and the significance parameter is above a predetermined threshold.

According to some embodiments, the decreasing comprises returning the intensity and duration to their starting levels.

According to some embodiments, following a measured current below a predetermined threshold a first amount of time is allowed to pass before the measuring after the laser is stopped and wherein following a measured current above a predetermined threshold a second amount of time is allowed to pass before the measuring after the laser is stopped and wherein the second amount of time is longer than the first amount of time.

According to some embodiments, the second amount of time is twice the first amount of time.

According to some embodiments, the predetermined current threshold is a predetermined percentage of a current through the nanopore at the predetermined size.

According to some embodiments, the predetermined percentage is 50%.

According to some embodiments, method further comprises a focusing step before step (a), wherein the focusing step comprising using white light imaging of the membrane to focus the laser light at the spot.

According to some embodiments, the method further comprises a focusing step before step (a), wherein the focusing step comprising shining the laser light at a reduced intensity on the membrane to produce a photoluminescent spot and selecting a focus at which the photoluminescent spot is at a minimum size, maximum intensity or both.

According to some embodiments, the laser light is continuous wave focused laser light.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1A:
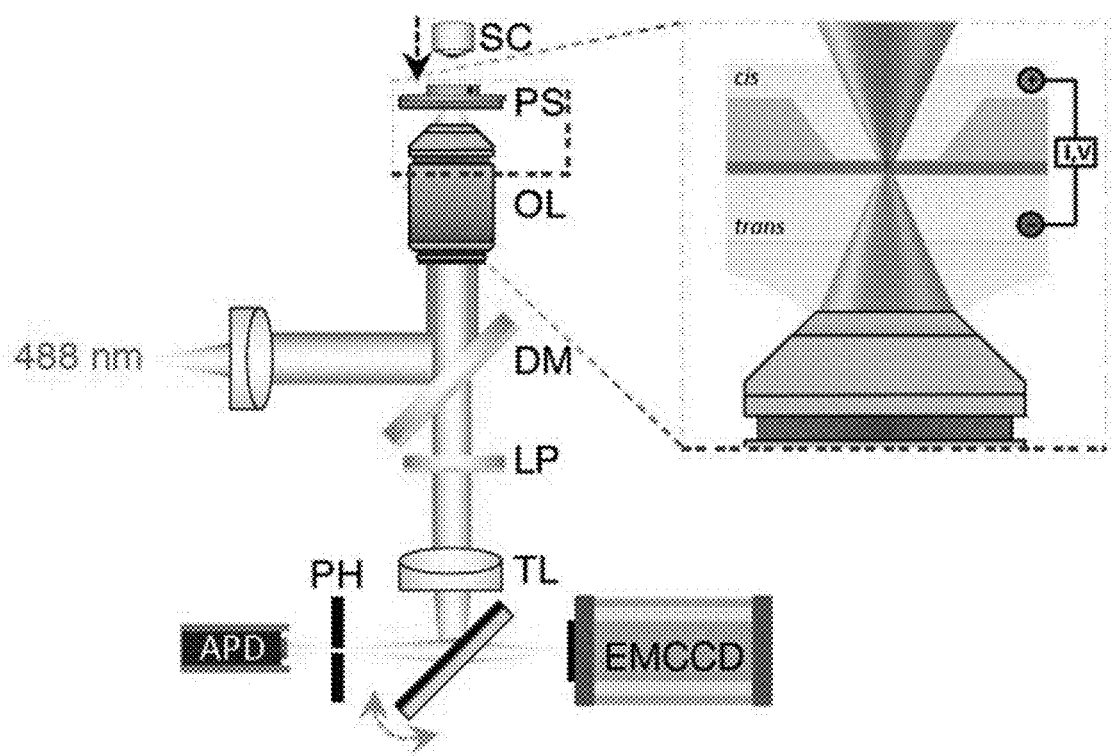
FIGS. 1A-D: Laser thinning of freestanding $SiN_x$. (1A) Schematic of the confocal setup. SC—$SiN_x$ chip; PS—piezo stage OL—objective lens; DM—dichroic mirror; LP—low pass filter; TL—tube lens PH—pinhole. The emission pathway is switchable between the APD and EMCCD. (1B) Focusing of a ~45 mW 488 nm laser on the membrane results in photoluminescence emission, which is recorded by the APD in the >550 nm range. (1C) Photoluminescence emission during laser-exposure, measured in counters per second. The laser is activated at t=0 seconds. (1D) Images of the 42×42 µm² membrane under white-light illumination before etching (i). After 300 seconds of laser exposure, a thin region is visible as a contrasted spot (ii).

(5F-H) Translocations of 5054 bp DNA at different applied voltages: 300 mV (red), 450 mV (orange) and 600 mV (yellow). (5F) Scatter plot of normalized translocation event blockage versus dwell time. (5G) Translocation dwell-time histograms showing voltage-dependent time constants of 500±25, 175±3, and 135±4 µs from lowest to highest voltage. (5H) Sample concatenated translocation events at each voltage. (5I) Scatter plot of normalized translocation event blockage versus dwell time of translocations of 5054 bp at 300 mV. (5J) Normalized translocation blockage histogram fitted by two Gaussians: $\langle I_B \rangle =0.57$ (green curve) and $\langle I_B \rangle =0.7$ (red curve) (5K) Sample concatenated translocation events. (5L) Scatter plot of di-ubiquitin (K63-linked di-Ub) translocation events at pH 7. The trans chamber was biased to 300 mV to drive translocation of 0.007 µg/µl di-Ub from cis to trans. (5M) A concatenated ionic current trace showing sample di-Ub translocation events. (5N) Translocations of di-ubiquitin (K63-linked Di-Ub) at 300 mV. (left) Translocation dwell-time histogram showing a decay time constant of 139±10 µs. (right) Normalized translocation blockage histogram fitted by a Gaussian: $\langle I_B \rangle =0.77$. N=326 events.

FIGS. 6A-D. Localized laser-etching of freestanding $SiN_x$. (6A) Laser-etched T-shape array of 9 thin regions spaced 1500±50 nm center-to-center. The top and vertical bars were etched with a laser intensity of ~30 mW and 45 mW, respectively, for 4 minutes each. Next to the T is a lithography-fabricated thin region (20±2 nm) for comparison. (6B) Zoom in of just the T. (6C) TEM image of the T, showing a difference in brightness for the top and vertical bars, corresponding with a difference in thickness. (6D) Nanopore formed in one of the thin regions.

FIGS. 7A-E. Nanopore fabrication by laser-etching. (7A) Schematic illustration of the electro-optical apparatus used for laser-assisted nanopore drilling. (7B-D) Laser thinning in three membranes with different indices of refraction: n=2.20, 2.29, 2.42 for 7B, 7C and 7D, respectively. Laser intensity is equal in all cases. Left: photoluminescence (PL) and current traces during the etching time. A sudden incline in the current trace indicates pore formation. For the n=2.20 membrane no pore was formed even after 2500 seconds, where for the n=2.29, 2.42 membranes pores were formed after 140 and 120 seconds respectively. Right: images of the membrane before and after thinning. In all cases a black spot (indicated by a black arrow) appears in the later images, where less light was reflected, indicating a thinner region. The formation of the thin regions corresponds to the PL traces (left) which decrease in all cases regardless of pore formation. These experiments were reproduced more than 100 times each. (7E) Chips with refractive index of 2.3 and initial thickness of 38-42 nm were immersed in 1M KCl buffer with pH of 7 or 10 heated to 90° C. in a temperature-controlled hot water bath. The $SiN_x$ thicknesses of 4 different chips were measured using ellipsometry after 2, 5, 30 and 60 minutes (pH 7—blue triangles, pH10—green tringles). Four control chips were immersed in 1 M KCl, pH 10 buffer at room temperature, and their thickness was measured as well (red triangles). After an hour immersion at 90° C. we observed a change in thickness of about 1 nm only.

FIGS. 8A-D. (8A) Material composition as a function of the refractive index measured using EDS (triangles) and EELS (circles). Red curve represents the theoretical model with reported theoretical values of $n_\infty=3.86$ $n_{3/4}=1.99$. Higher refractive index indicates higher percentage of silicon in the membrane. Fitting each of the measurements with the theoretical model resulted in the following parameter values: $n_\infty=3.9949$ $n_{3/4}=1.9638$ for the EELS and $n_\infty=3.6827$ $n_{3/4}=1.7401$ for the EDS (solid black lines). (8B) Low loss peaks measured using HR-EELS with the monochromated zero loss peak (ZLP) of 0.17 eV (left panel). The measurement was repeated for two different chips (n=2.15—green curve, n=2.42—blue curve). Zoomed in plot of the 0-8 eV region in presented in the right panel and was used to estimate the material bandgap. The energies of the laser wavelengths available in our sensing apparatus is presented using red (640 nm), green (532 nm), and blue (488 nm) vertical lines. (8C) Measured photoluminescence (PL) and ionic current during laser-exposure (red and grey curves, respectively) of different wavelengths. The high refractive index (2.43) chip was easily drilled using a 488 and 532 nm lasers in less than a minute or roughly two minutes, respectively. In contrast, the low refractive index chip (2.15) could not be drilled at these laser intensities even after 10 minutes. Illuminating the chips with the red laser (640 nm) did not result in thinning or drilling in either case. (8D) Average PL values for four different types of chip (n=2.15, 2.2, 2.3, 2.43) of similar thickness (44-46 nm). Lower refractive index corresponds to higher PL (dark grey marks). The results are fitted to exponential curves (dark grey solid line). Light grey triangles present the ratio of the red-band emission over the total emission which increases as the refractive index increases. This is associated with a red-shift of the PL at the higher Si:N ratio. Each measurement was repeated using 4 chips of each type.

Figure 9:
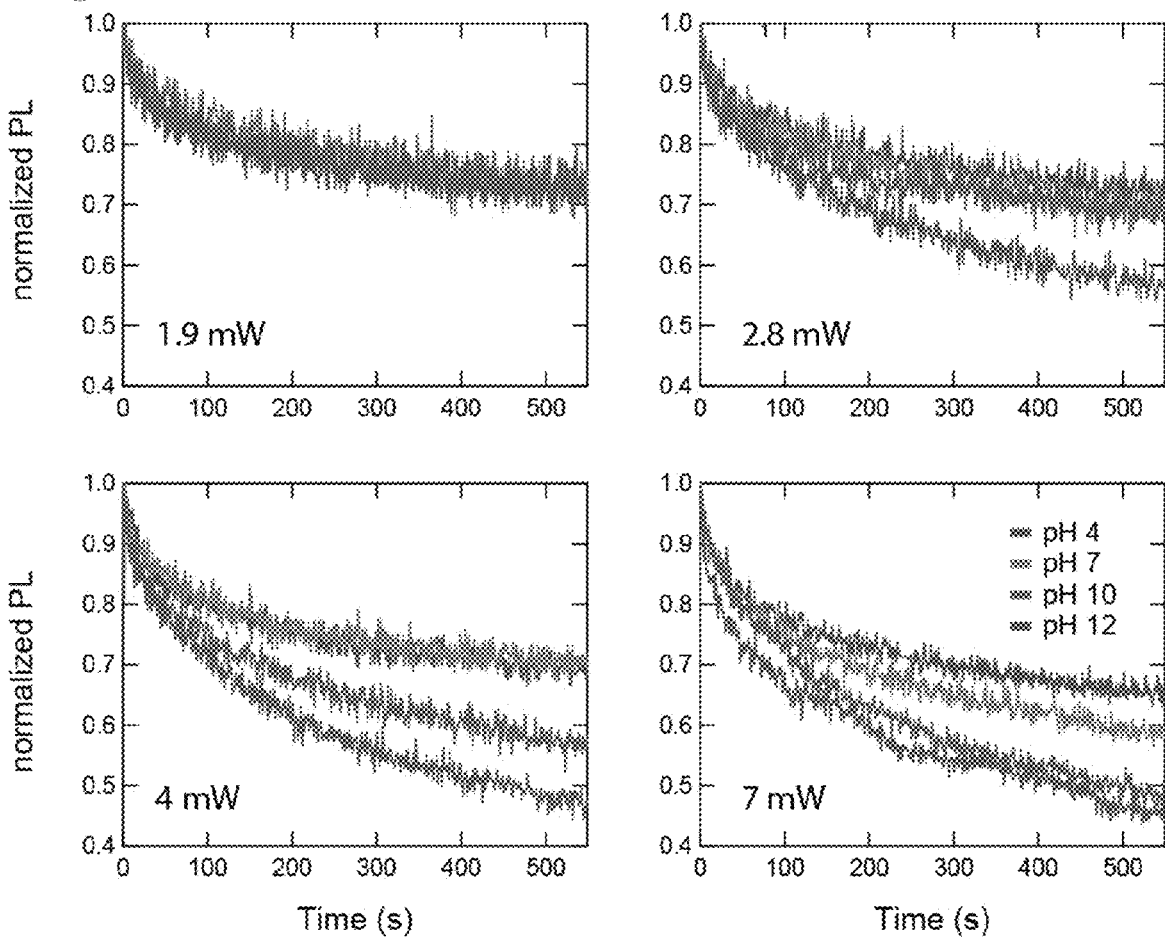

FIG. 9. Normalized PL traces of membrane thinning using different laser intensities (1.9 to 7 mW) and the four pH values (pH 4—red, pH 7—green, pH 10—blue, pH 12—purple). While acidic and neutral buffers (pH 4 and 7) hardly change the PL behavior even when the intensity is increased, the hydroxyl-rich solutions (pH 10 and 12) increase the effectiveness of the etching, producing thinner membranes at high speed.

Figure 10A:
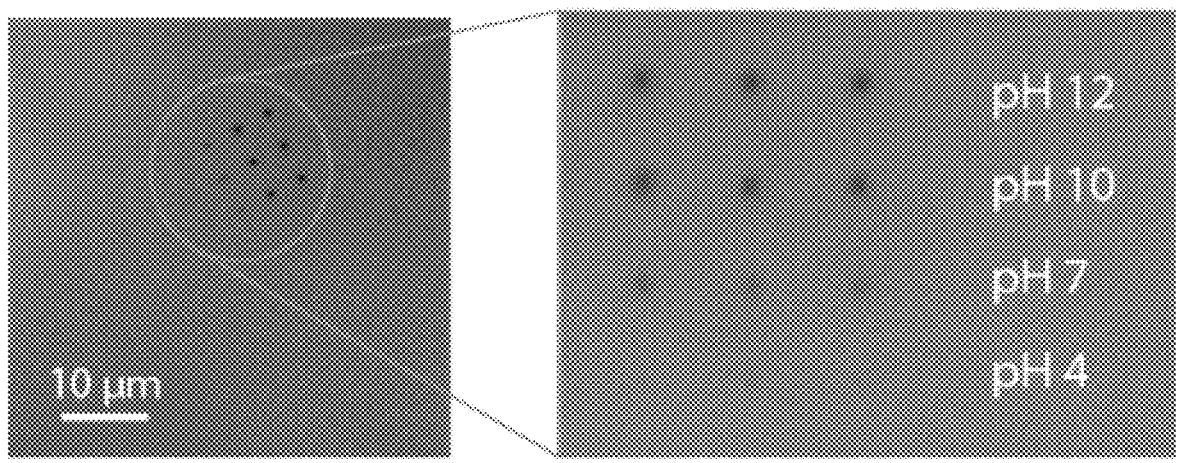
Figure 10B:
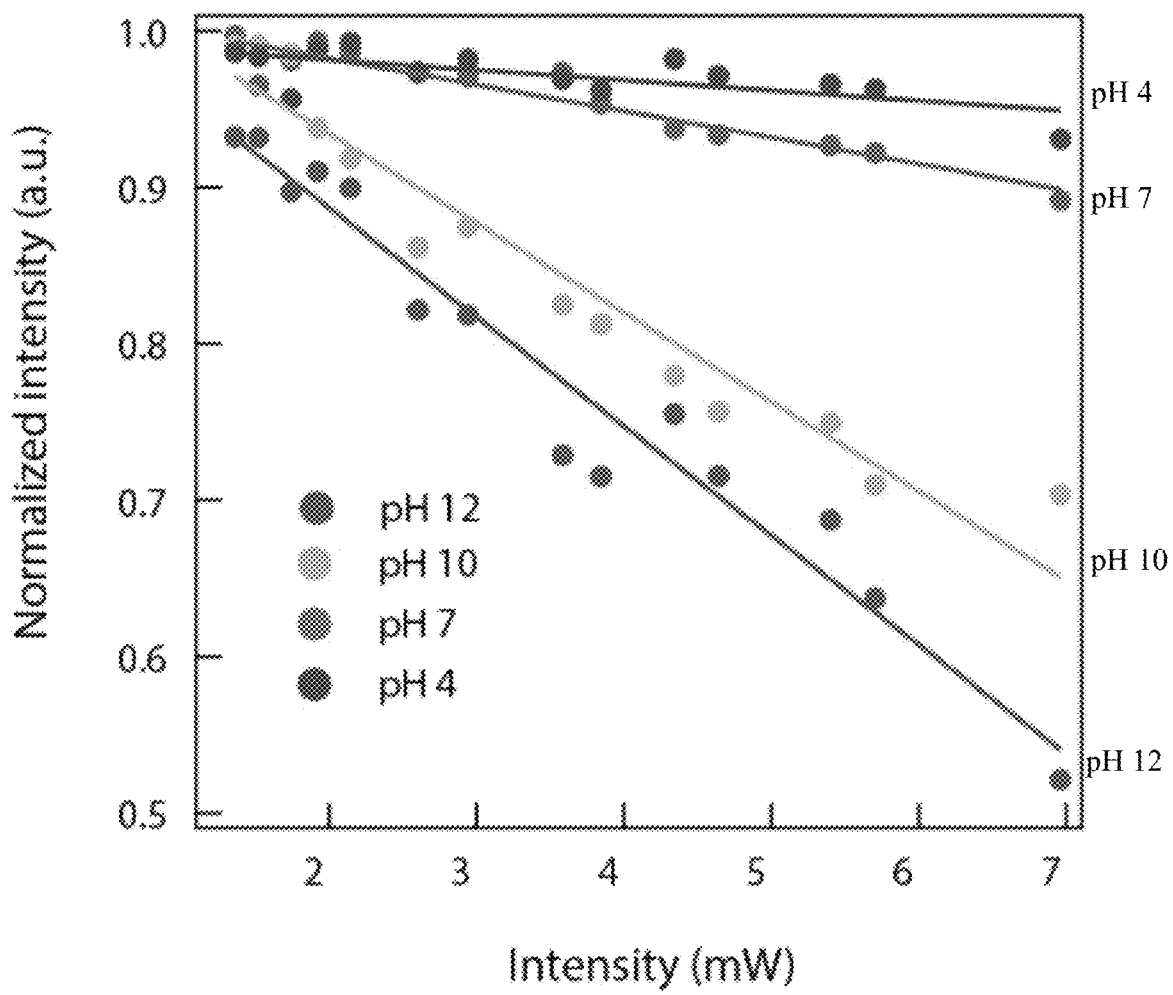

FIGS. 10A-B. Membrane thinning as a function of the solution pH. (10A) Reflected white light image of a chip (n=2.3) before laser exposure (488 nm) and after exposing it for one minute at different pH levels and 1 M KCl (each measurement was repeated 3 times). (10B) The normalized intensity is the change in reflected white light according to (signal-background)/background for each condition (4 different pH levels) after exposing the chip for two minutes as a function of the laser intensity. Solid lines for each pH imply a linear dependence.

FIGS. 11A-D. Characterization of the ultra-fast drilling process. (11A) STEM thickness map of a thin region created using increasing laser exposure durations. Conditions: 488 nm, 34 mW, 1 M KCl, pH10. A longer exposure duration results in a thinner membrane. (11B) STEM thickness map of a thinned region created using increasing laser exposure durations. Conditions: 488 nm, 7 mW, 1M KCl, pH 10. Longer exposure duration results in thinner membrane. (11C) x-line scan in the middle of the thickness map for each exposure duration. (11D) Normalized, integrated thickness for x-line scans taken in the middle of the thickness maps for each exposure duration (circles), and the PL trace as a function of time (grey). Inset—high magnification TEM images for selected thin regions. After laser exposure of 15 s one ~6 nm pore was created in the middle of the Gaussian shaped thin region. Longer exposures resulted in the formation of multiple pores.

Figure 12A:
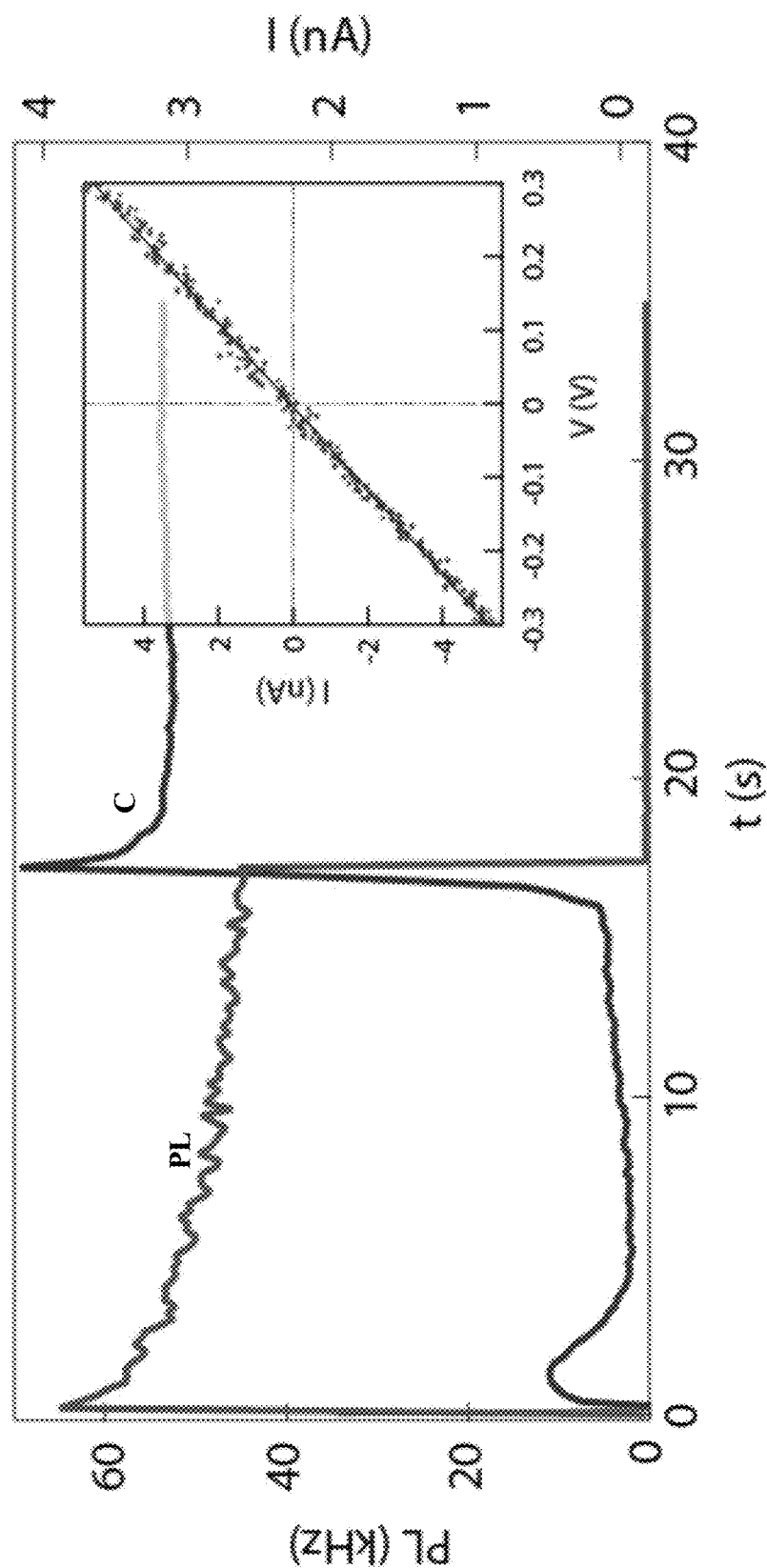
Figure 12B:
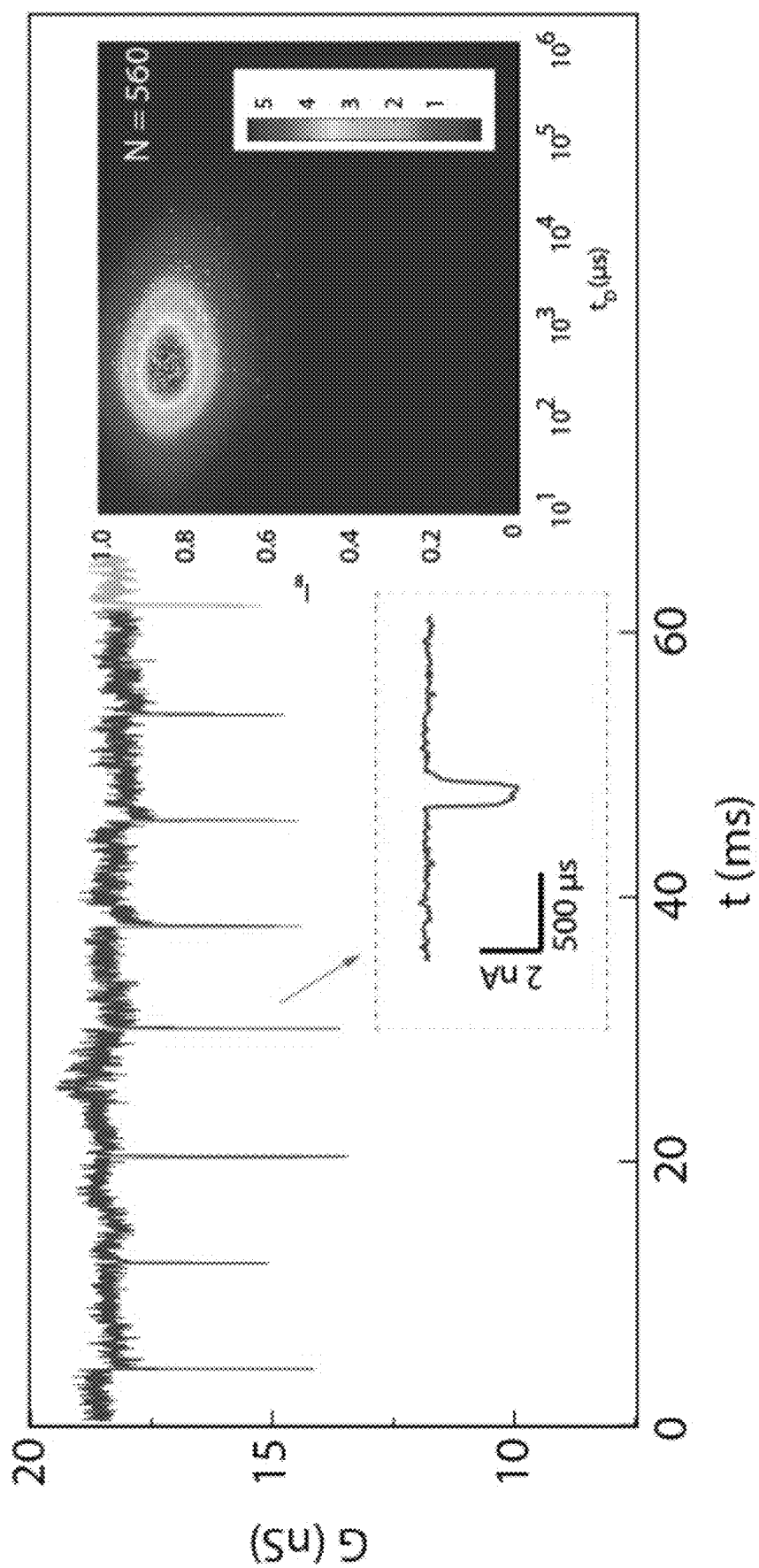

FIGS. 12A-B. DNA translocations in a fast-drilled nanopore. (12A) Photoluminescence (PL) and current traces of a pore drilled in ~15 seconds. The laser was turned on at t=0, as can be indicated by an abrupt PL increase. The PL decays over time as the membrane is thinned until pore formation, signaled by an increase in the electrical current. Conditions: 1 M KCl, pH 10, 300 mV, 488 nm wavelength with intensity of 7 mW. The inset shows the current-voltage (IV) curve for this nanopore after the buffer was changed to pH 7 and the open pore current stabilized. (12B) Concatenated dsDNA (300 bp) translocation events with a zoomed in plot of an event, and the scatter plot of the blocked current ($I_B$=$I_{blocked}$/$I_{open}$) vs. the dwell time $t_D$ of all the events (N=560).

Figure 13A:
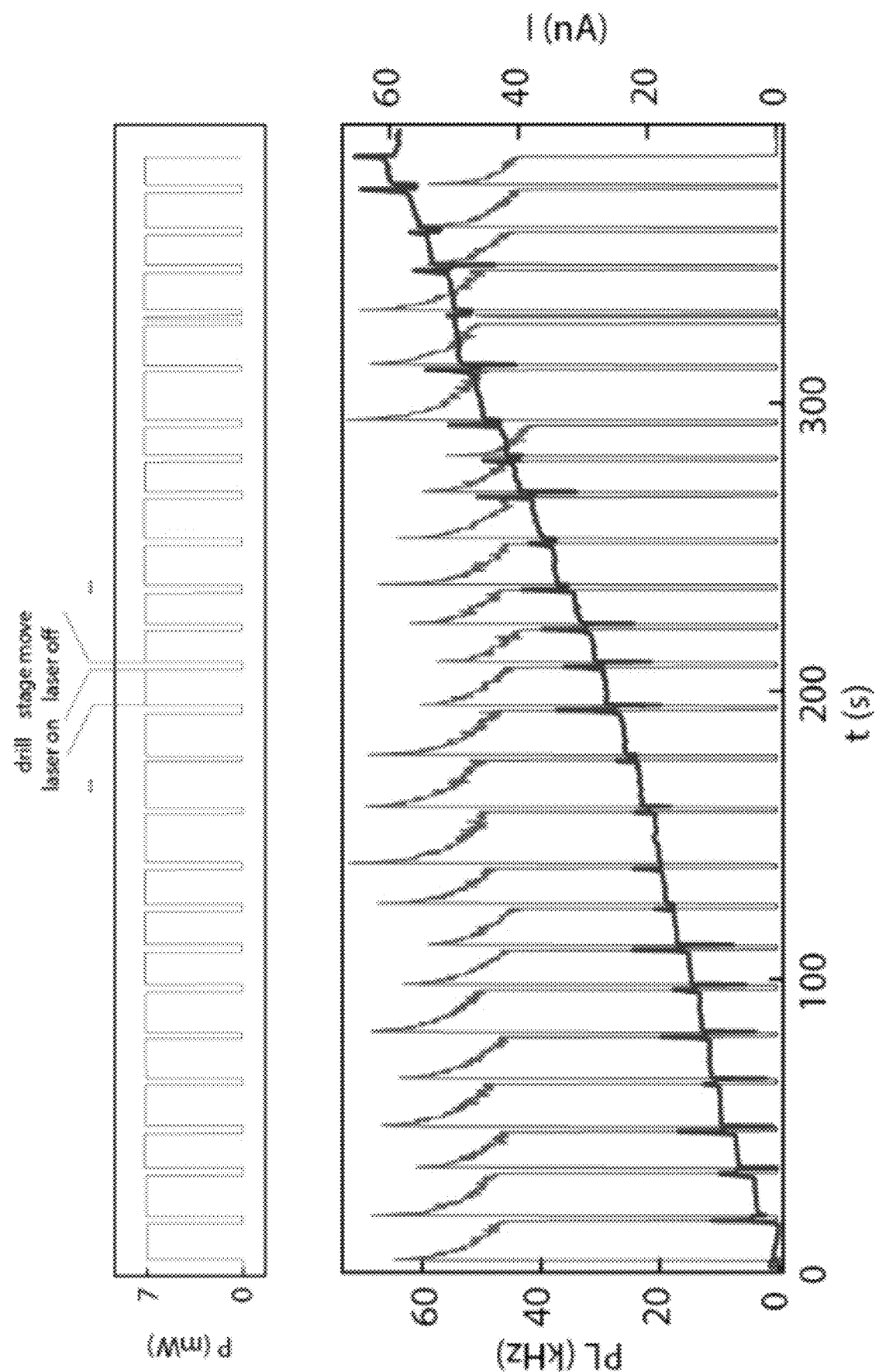
Figure 13B:
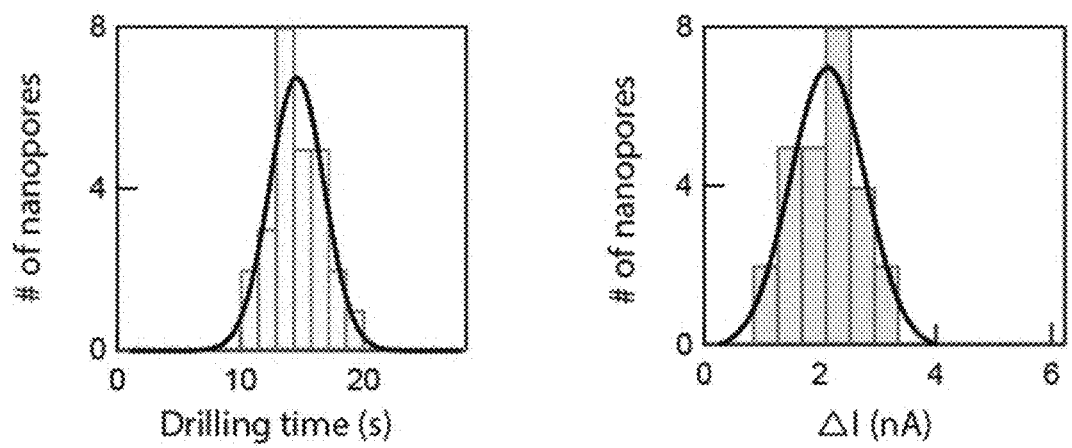
Figure 13C:
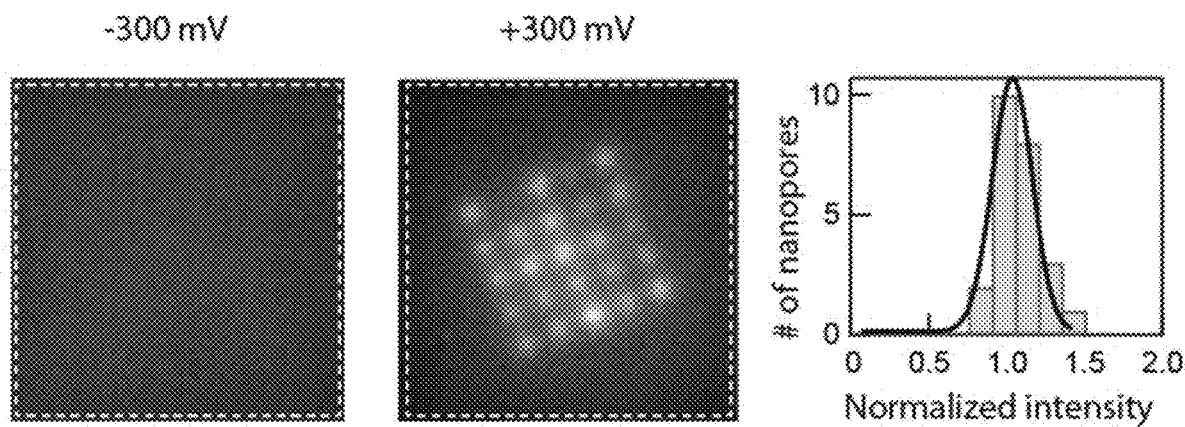

FIGS. 13A-C. Fast drilling of nanopores array using a focused laser beam. (13A) Top: laser intensity time trace during nanopore array drilling. The laser power is switched automatically on and off for each drilling event, followed by controlled movement of the piezo stage to the next coordinate. Bottom: Photoluminescence (PL, red) and current (blue) traces of an array of 25 pores drilled in ~6 minutes. When the current rapidly increases, the laser is automatically turned off and the PL drops. (13B) Histograms of the drilling time and the change of current for each pore, and Gaussian fitting for each histogram (13.6±3.1 seconds, 1.9±0.9 nA) (13C) Wide-field illumination images of the entire membrane using 488 nm laser. Calcium ($Ca^{+2}$) activated fluorophores are used for verifying the creation and position of the nanopore array. At 300 mV $Ca^{+2}$ passes through the pore and binds to Fluo-4, resulting in a fluorescence spot at the thin region (middle panel). The spot disappears when the bias is reversed to −300 mV (left panel). The membrane position is outlined by a white dashed line. The histogram in the right panel describes the normalized intensity distribution of the 25 pores. Grey curve is a Gaussian fit (0.97±0.18).

Figure 14A:
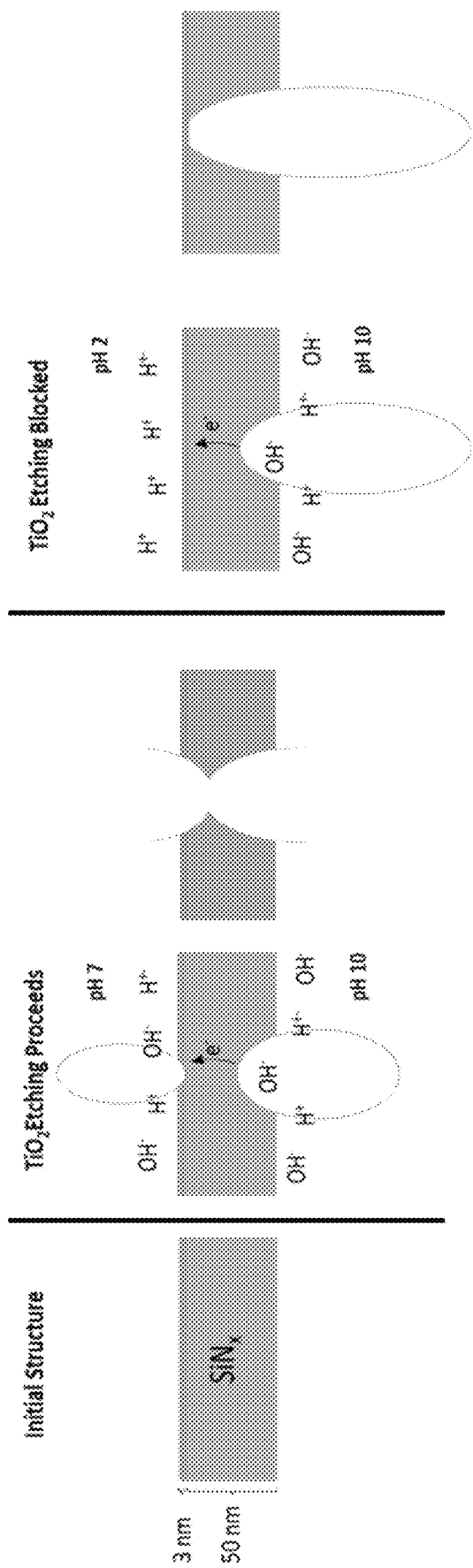
Figure 14B:
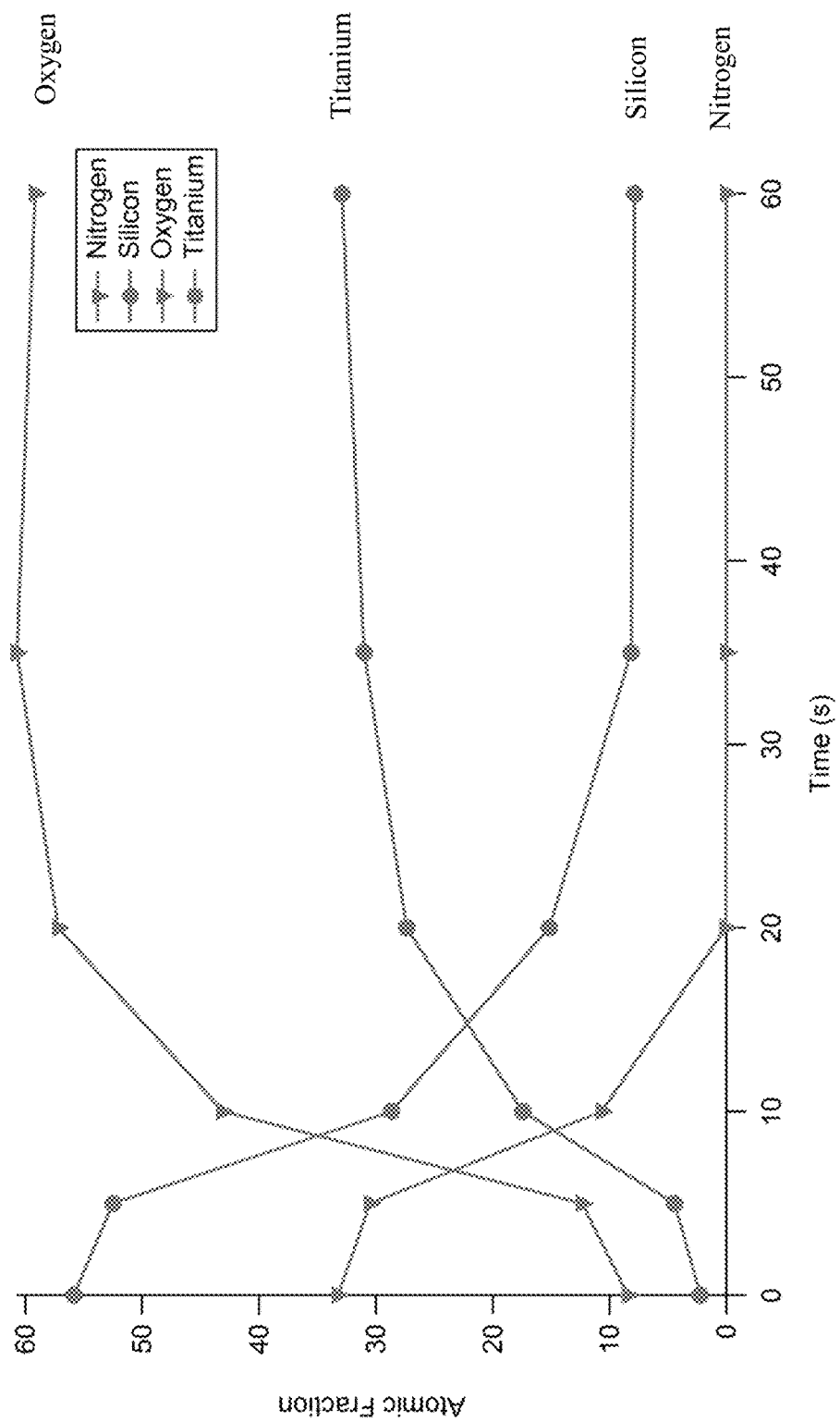

FIGS. 14A-B. (14A) Cartoon of drilling in a membrane comprising $SiN_x$ and $TiO_2$. The bottom layer is the $SiN_x$ and the top layer is the $TiO_2$. Laser light shown on the silicon layer catalyzes drilling in the titanium layer which had previously been refractory to drilling. Acidic pH on the titanium side inhibits this catalyzation, whereas neutral or alkaline pH is permissive. (14B) Line graph of the atomic fraction of each component of the membrane at the site of drilling as a function of time.

Figure 15A:
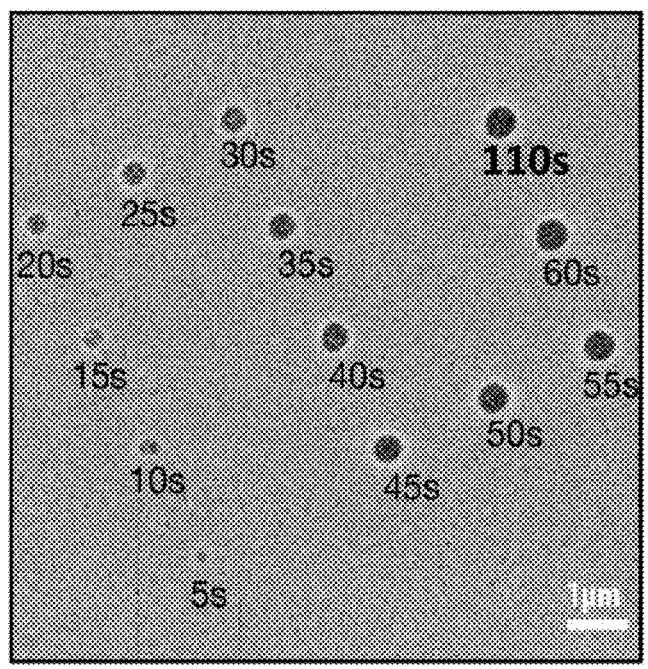
Figure 15B:
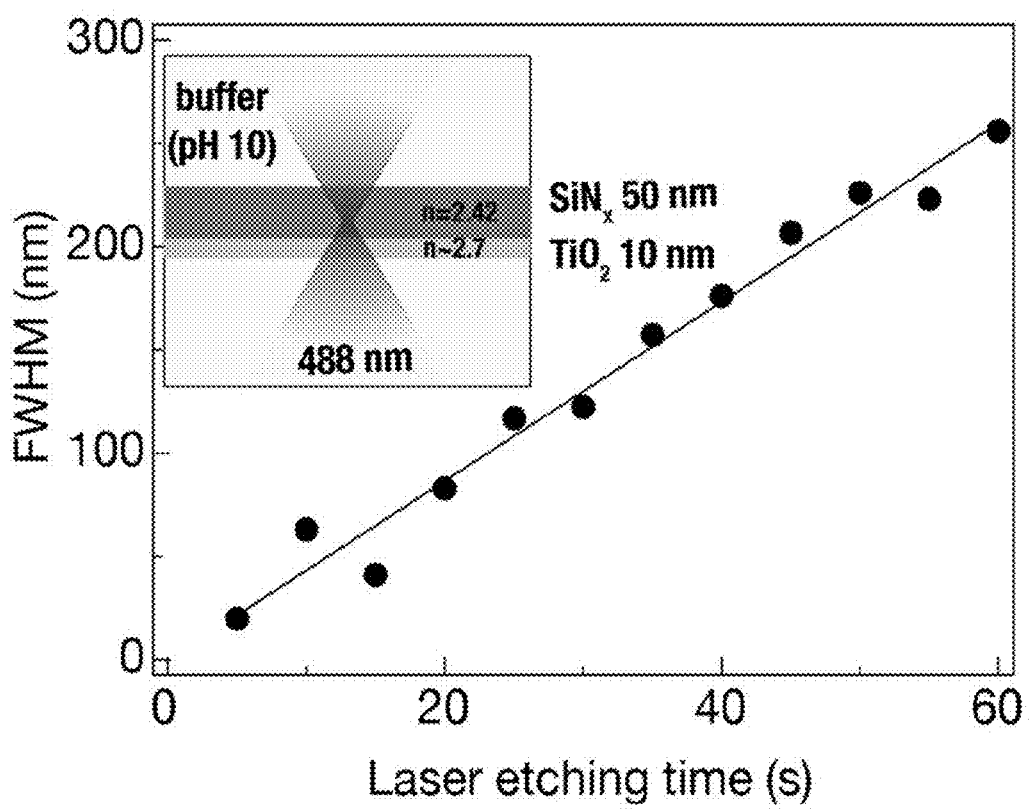
Figure 15C:
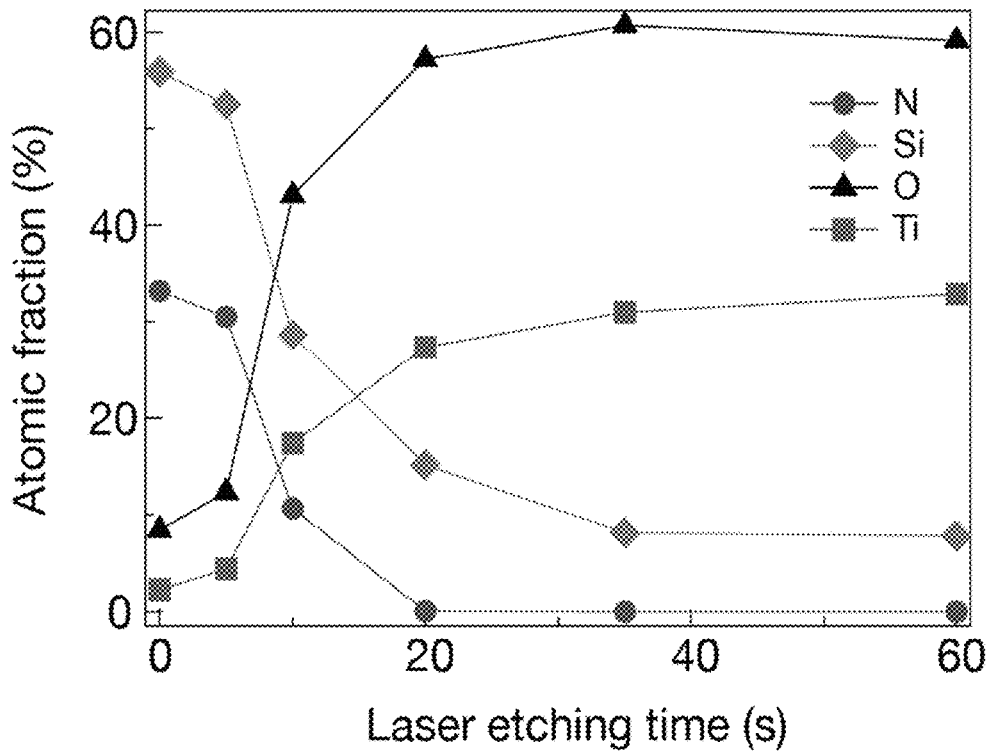

FIGS. 15A-C: Characterization of the laser-drilling (LD) kinetics using transmission electron microscopy (TEM). (15A) A series of etch marks applied by the 488 nm laser at varying doses, imaged with TEM. The dose increases in 5-second increments from 5 s to 60 s, with an additional over-etching dose of 110 s. (15B) An analysis of the FWHM obtained at different doses. The laser forms nano-wells with a diameter that is linearly dependent on the laser dose. Inset: A schematic of the specimen used in this study. The 50 nm silicon nitride ($SiN_x$) free-standing membrane was coated with a thin 10 nm layer of $TiO_2$, and the structure was etched by the Gaussian laser beam. (15C) Elemental analysis by Energy Dispersive X-ray Spectroscopy (EDS). The elemental composition of the 5-, 10-, 20-, 35- and 60-second etch marks were measured. The background was used for the 0-second point. The atomic fraction of the $TiO_2$ elements increases, while the $SiN_x$ elements decrease, demonstrating that LD depletes only specific elemental components of the membrane.

FIGS. 16A-D. System design and laser drilling time traces. (16A) Optical setup overview. The 405 nm continuous-wave laser is transmitted into the objective and focused on the membrane, where the reflected light is long-pass-filtered to measure photoluminescence (PL) by the sCMOS camera. The applied voltage, laser power, ND filters, camera and piezo stage are fully controlled by custom LabVIEW software (gray dashed arrows). The laser power is measured before the objective lens (black dashed line). (16B) Schematic of the software designed to run the nanopore laser drilling algorithm (NLDA). After the user sets the chip above the objective and positions the laser, he presses the start button. Then, the autofocus is activated, followed by the NLDA. The inputs (described in methods section) are used to ensure convergence to the set nanopore value. (16C) The NLDA three main steps: thinning, drilling, and polishing. For display purposes only, the photoluminescence (PL) and current (C) traces are smoothed and interpolated, thereby allowing a clear representation during the process (see FIG. 24 for the raw data). During the experiment, the PL decreases, indicating local thinning, while the current rises to the target open pore current level. The pulse intensities and durations are represented by the violet trace. During the thinning step, the laser exposure is continuous. Starting from the drilling step, the laser is set to pulse mode, so the intensity trace is fragmented with increasing intensity and duration. In the polishing phase, the pulses are set to be short and weak since the current is susceptible to rapid increases. (16D) Pore stabilization, demonstrating how the open pore current is maintained over 20 minutes. The NLDA parameters used in this example, inputs: $P_0$=14.4 mW, $P^+$=1%, $$\eta_{TH} = 4\frac{nA}{s},$$

$I_t$=6 nA; parameters: $t_0$=100 ms, d=1 s, $\tau_{IPD}^l$=2 s, $\tau_{IPD}^s$=1 s, $\gamma$=1.2, $\varphi_{TH}$=1 nA, $\rho_{TH}$=0.8, $\psi_{TH}$=1 nA, R=2.

FIGS. 17A-D. Samples of nanopore laser-drilling algorithm (NLDA) experiments. (17A) Drilling time statistics. Histogram of the drilling time (not including stabilization) fitted using a Gaussian function. The mean and STD are indicated. (17B) Final open pore current $I_{result}$ with respect to the set target size by the NLDA $I_t$. Whiskers show one STD and outliers are marked with asterisks. The gray line is linearly fitted to the group mean values (gray points) obtaining slope=1.026±0.062. (17C) Histogram of the deviation of the final current from the target current $\Delta$=$I_{result}$−$I_t$. NLDA achieves an error of <5%. (17D) Three representative NLDA examples taken from the population. Each one was set with a different $I_t$ of 3 nA, 4 nA and 6 nA, and obtained drilling times of 85.4 s, 26.3 s and 52.3 s, respectively, from top to bottom. The stability of the nanopore open pore current up to 5 minutes is presented for each trace.

Figure 17A:
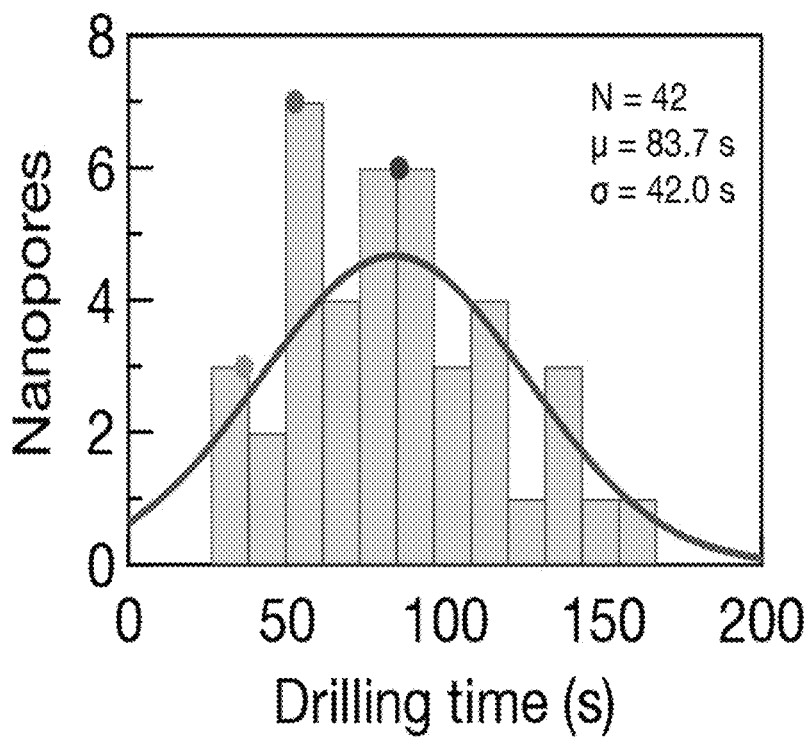
Figure 17B:
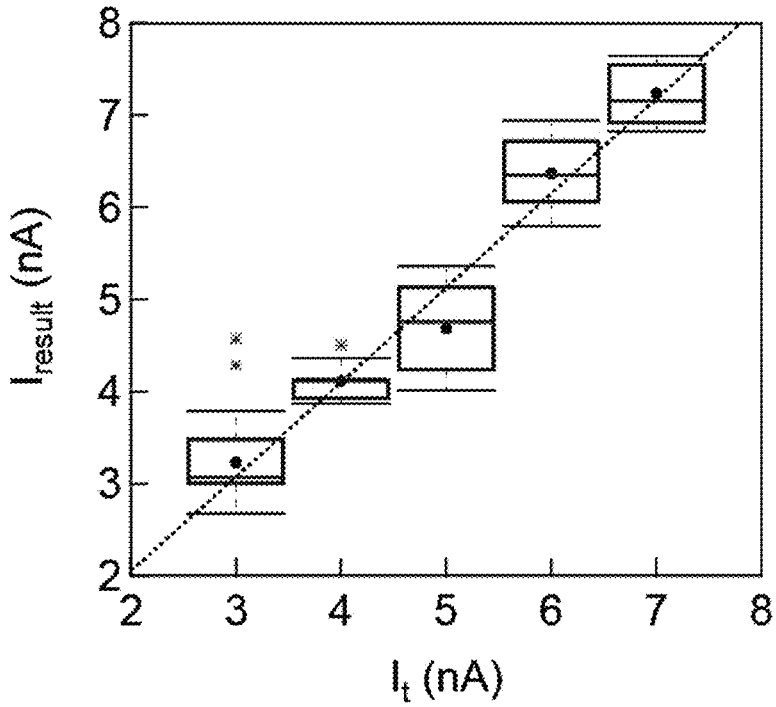
Figure 17C:
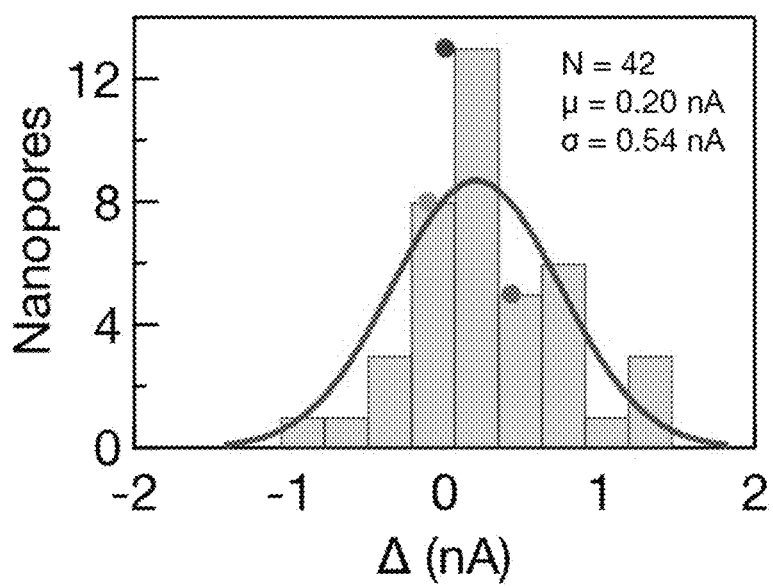
Figure 17D:
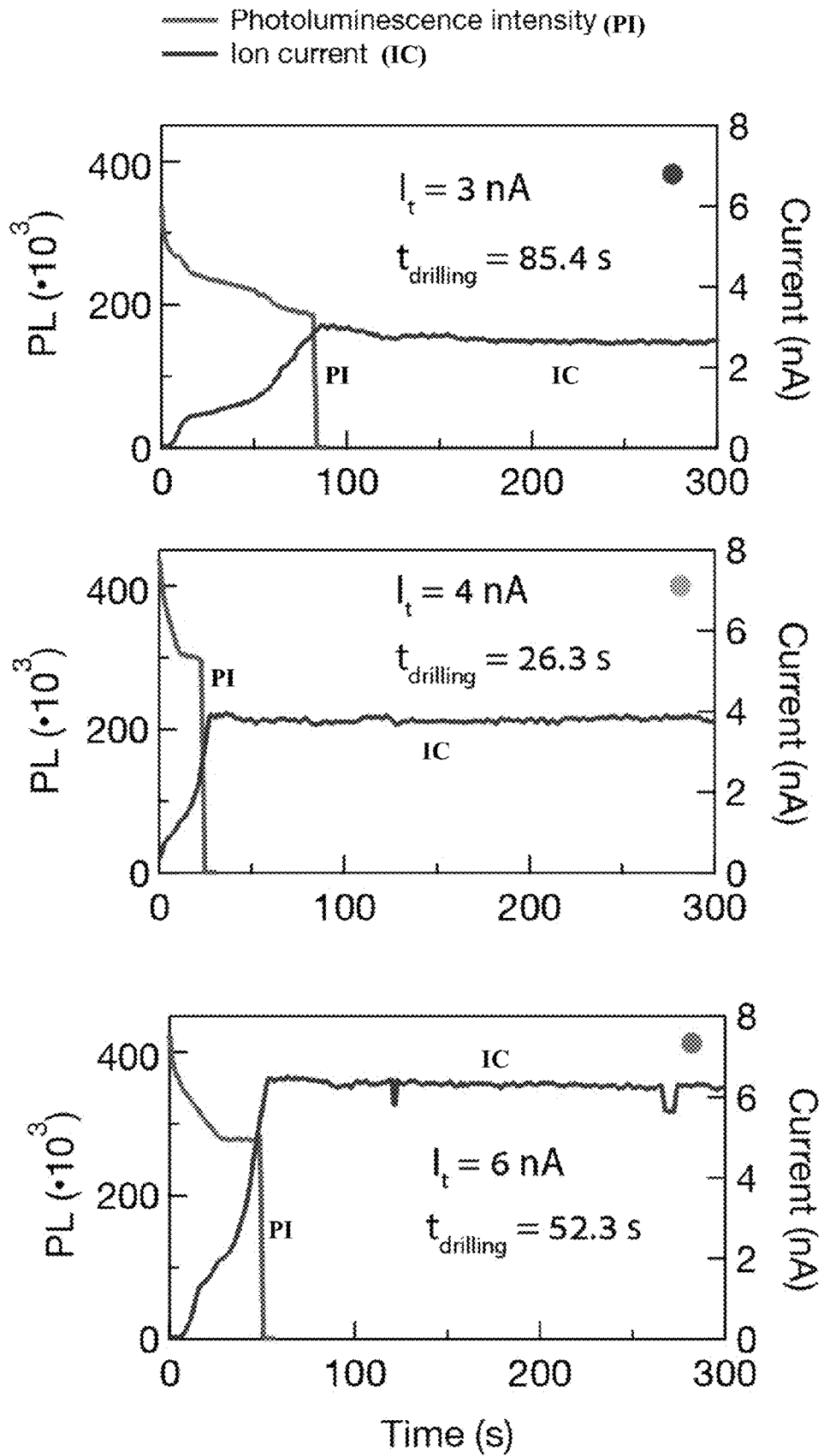
Figure 18A:
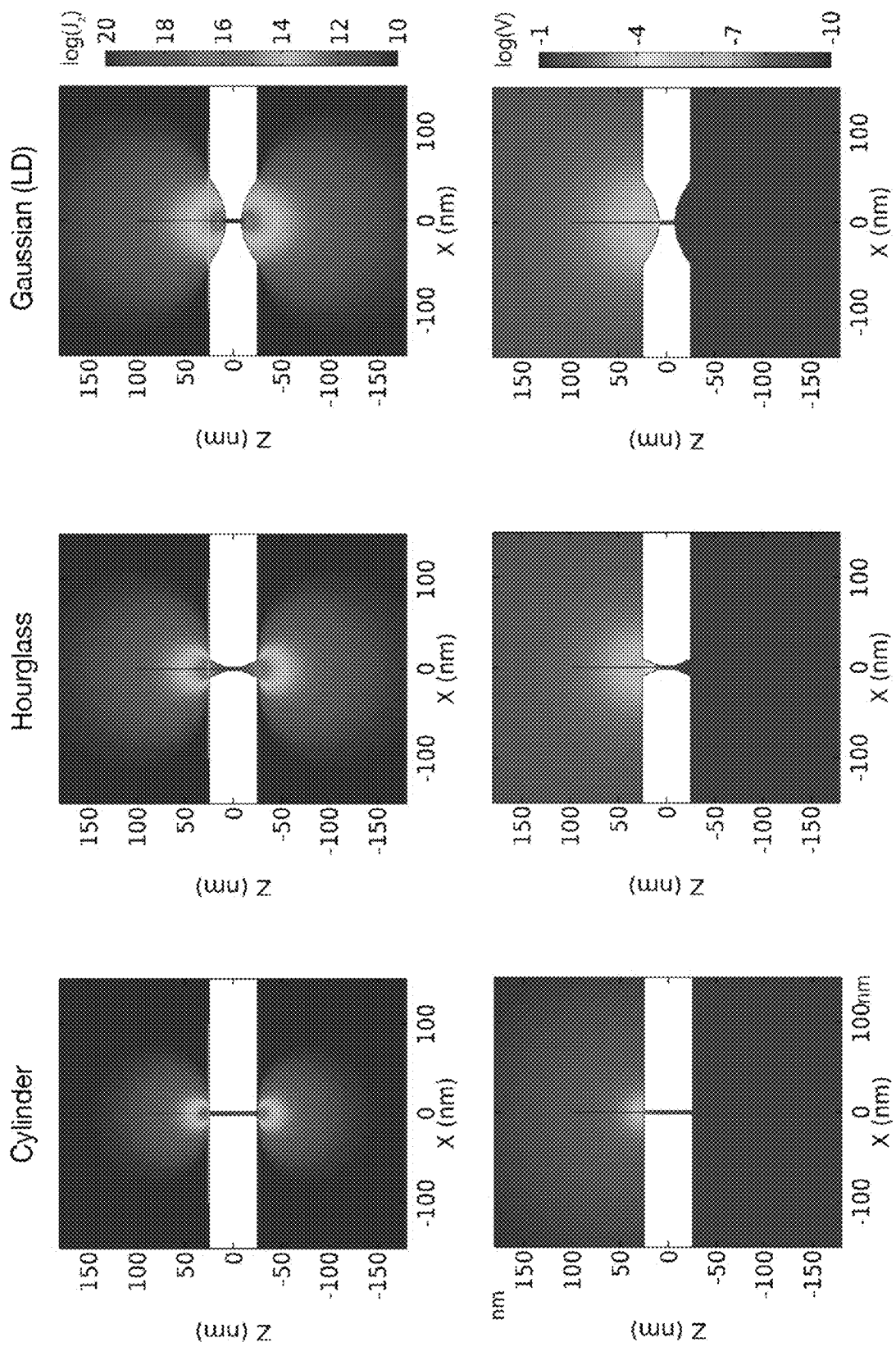
Figure 18B:
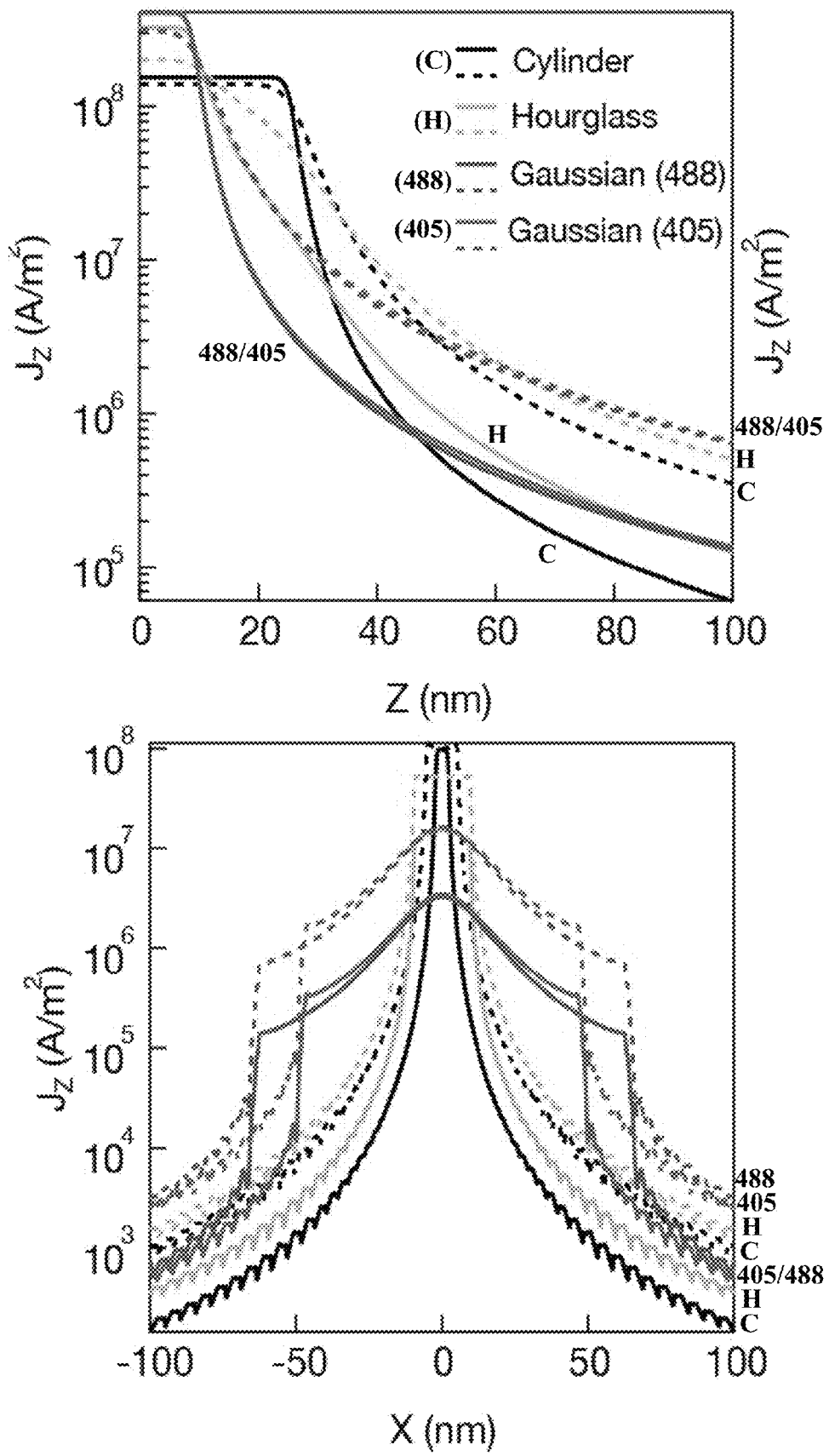
Figure 18C:
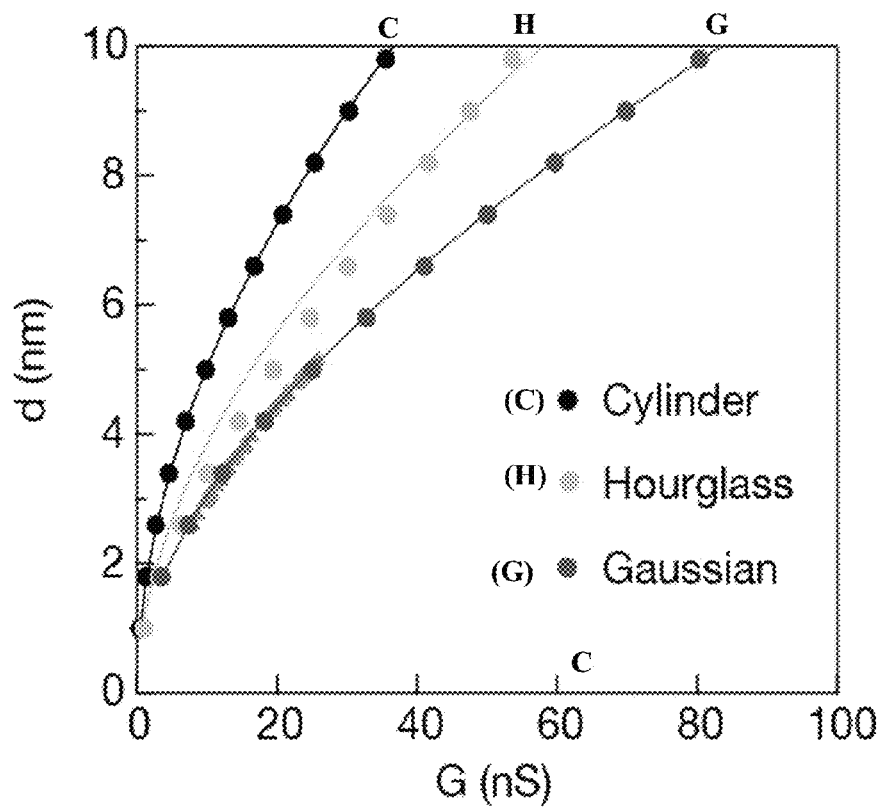

FIGS. 18A-C. Numerical simulations of the spatial distributions of the electrical potential and current density in the vicinity of ssNPs having either a perfect cylinder, hourglass or Gaussian form factors. (18A) Simulated spatial distributions of the current density z-component ($J_z$, top row) and the electric potential (bottom row) distributions using the three form factors, as indicated (d=4.2 nm). The Gaussian form factor's thickness profile assumed a $\lambda$=405 nm Gaussian laser's beam. The X axis is obtained by cylindrical reconstruction. (18B) Top and bottom panels show Z and X cross sections of the $J_z$ calculated along the horizontal and vertical lines in 18A, respectively. Solid and dashed lines correspond to 4.2 nm and 10.6 nm diameter pores, respectively. (18C) Numerical evaluation of the nanopore conductance G at different diameters d from the simulations. Data was globally fitted using equation 1 (solid lines) as described in the text. Grey triangles represent the nanopore diameters obtained in the experiments from FIG. 17 that were computed according to the measured conductance.

Figure 19A:
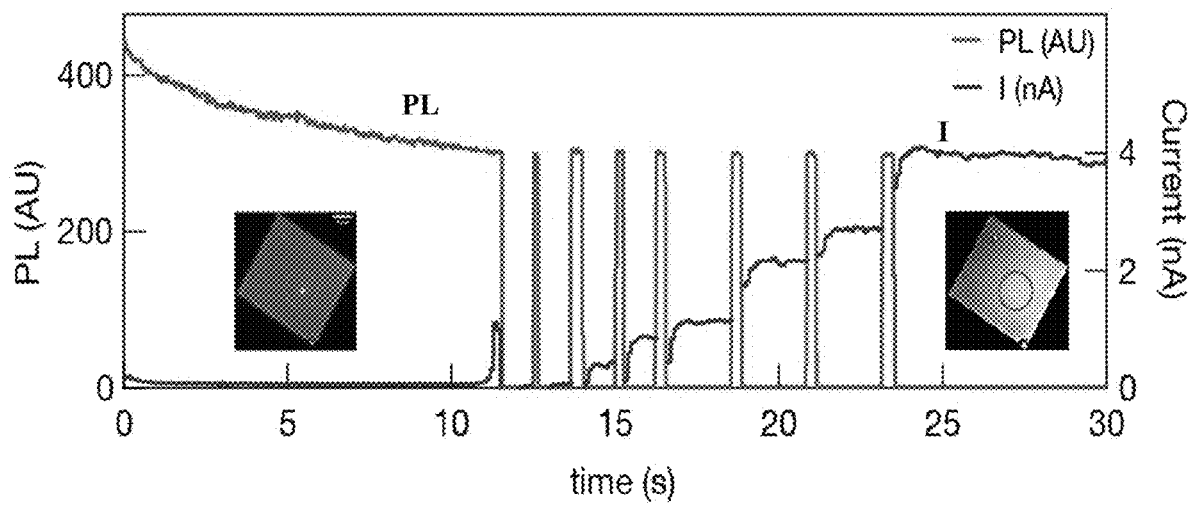
Figure 19B:
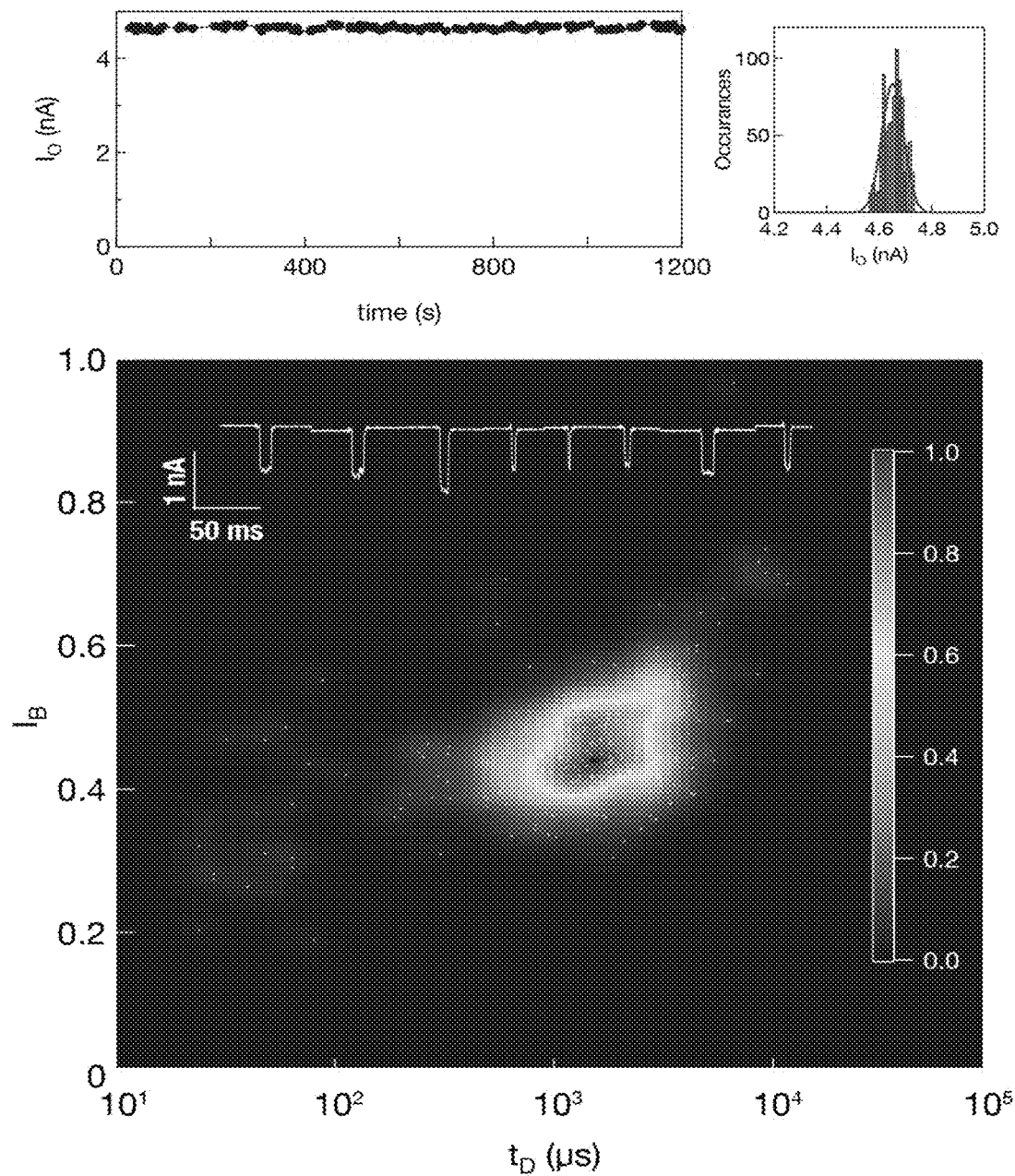

FIG. 19A-B. SDS-denatured carbonic anhydrase II proteins (CA) translocations using a laser-drilled nanopore.

(19A) NLDA process, showing the PL and ion current traces during thinning and drilling. The whole processes last 30 s, where the target open pore current was $I_t$=4 nA. Inset shows bright light before pore formation (PL spot visible, violet circle) and thinned area after drilling (laser off, red circle). (19B) Nanopore stability during translocations of SDS-denatured CA. Top: After addition of the CA analytes and SDS molecules, the open pore current ($I_O$) increased to 4.65 nA and remained stable during at least 20 minutes of recording the CA translocations. Right panel shows $I_O$ values in between the events and its histogram fitted to a Gaussian function 4.65±0.05 nA (mean±STD). Bottom: a scatter plot of the fractional blocked current and dwell time $t_D$ for the 437 translocation events collected in about 20 minutes. The scatter plot is superimposed on a heat map representing the 2D histogram density. Inset shows typical translocation events.

Figure 20B:
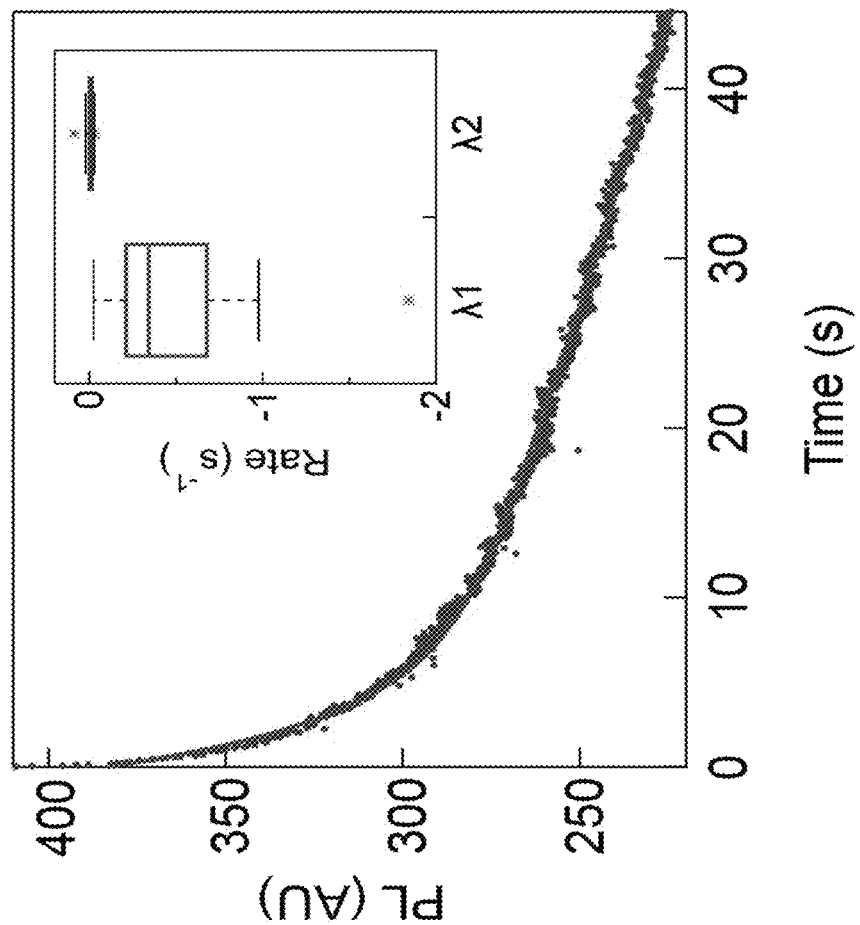
Figure 20A:
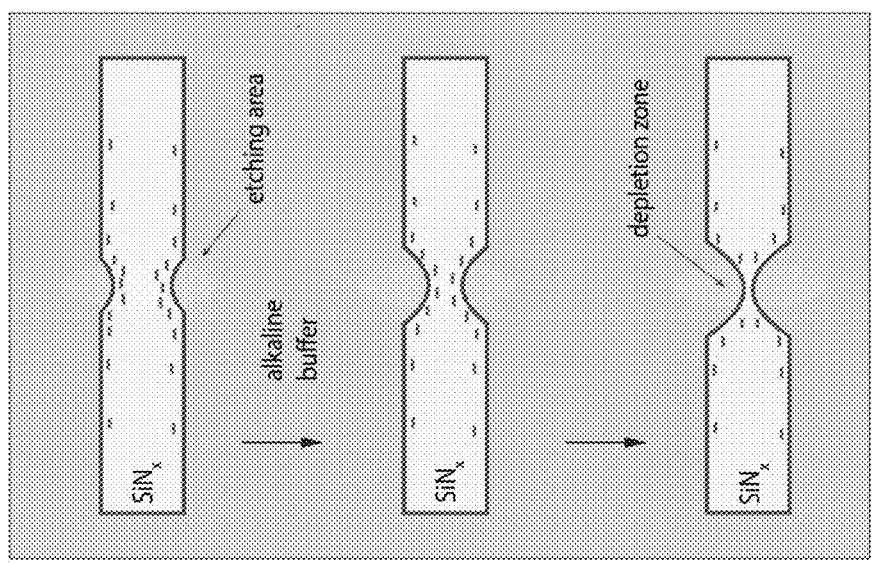

FIGS. 20A-B. (20A) A schematic (not to scale) model for the photochemical SiNx membrane thinning leading to pore formation. A charge depletion zone is generated by the thinning process. (20B) A characteristic photoluminescence intensity trace during membrane thinning showing a fast decay followed by a slow decay. The processes are approximated by a sum of two decaying exponentials with rate constants $\lambda_1$ and $\lambda_2$. Analysis of 15 membrane thinning traces consistently yield two decaying rates differing by two orders of magnitude (inset, boxplot is defined as in FIG. 17).

Figure 21A:
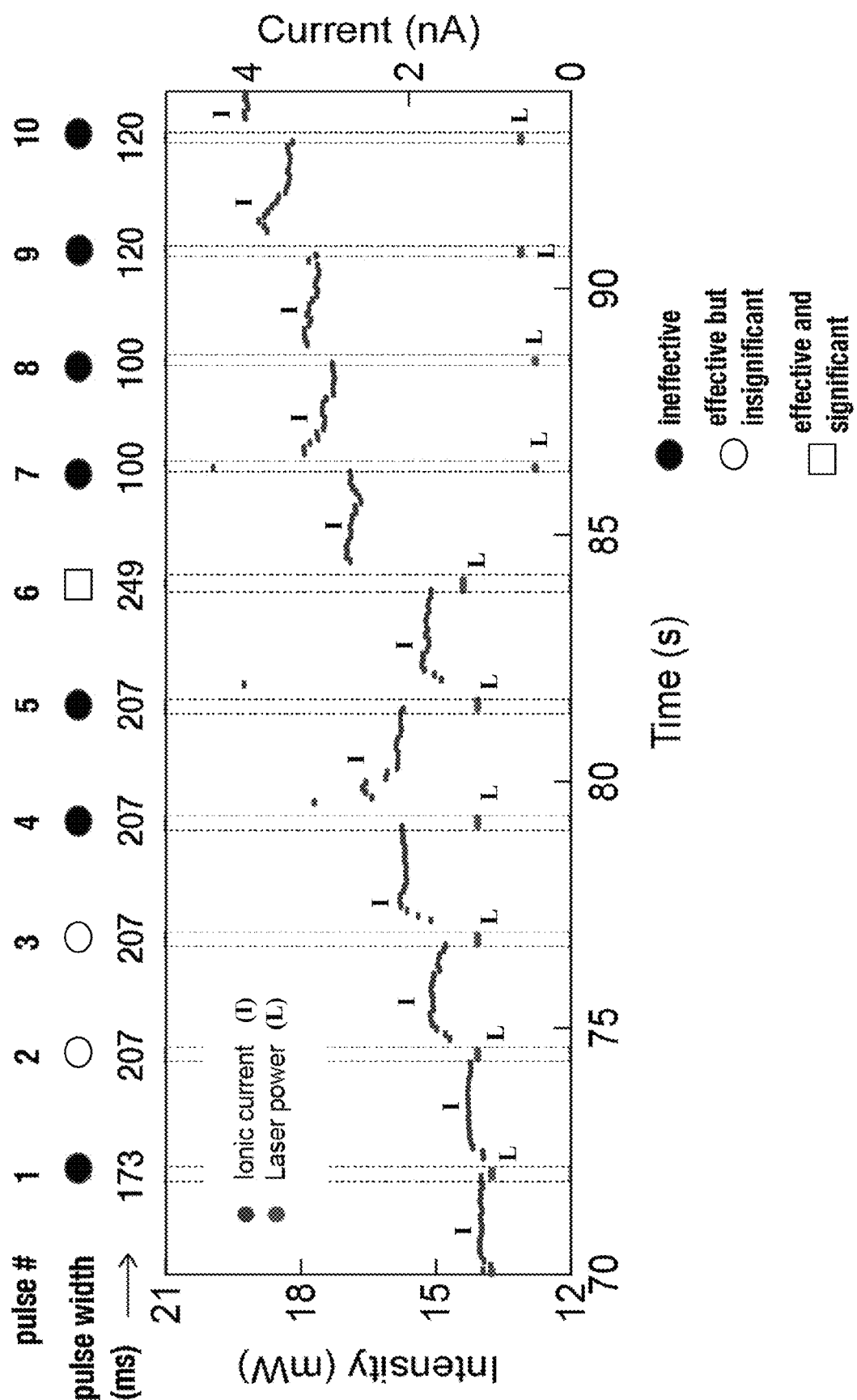
Figure 21B:
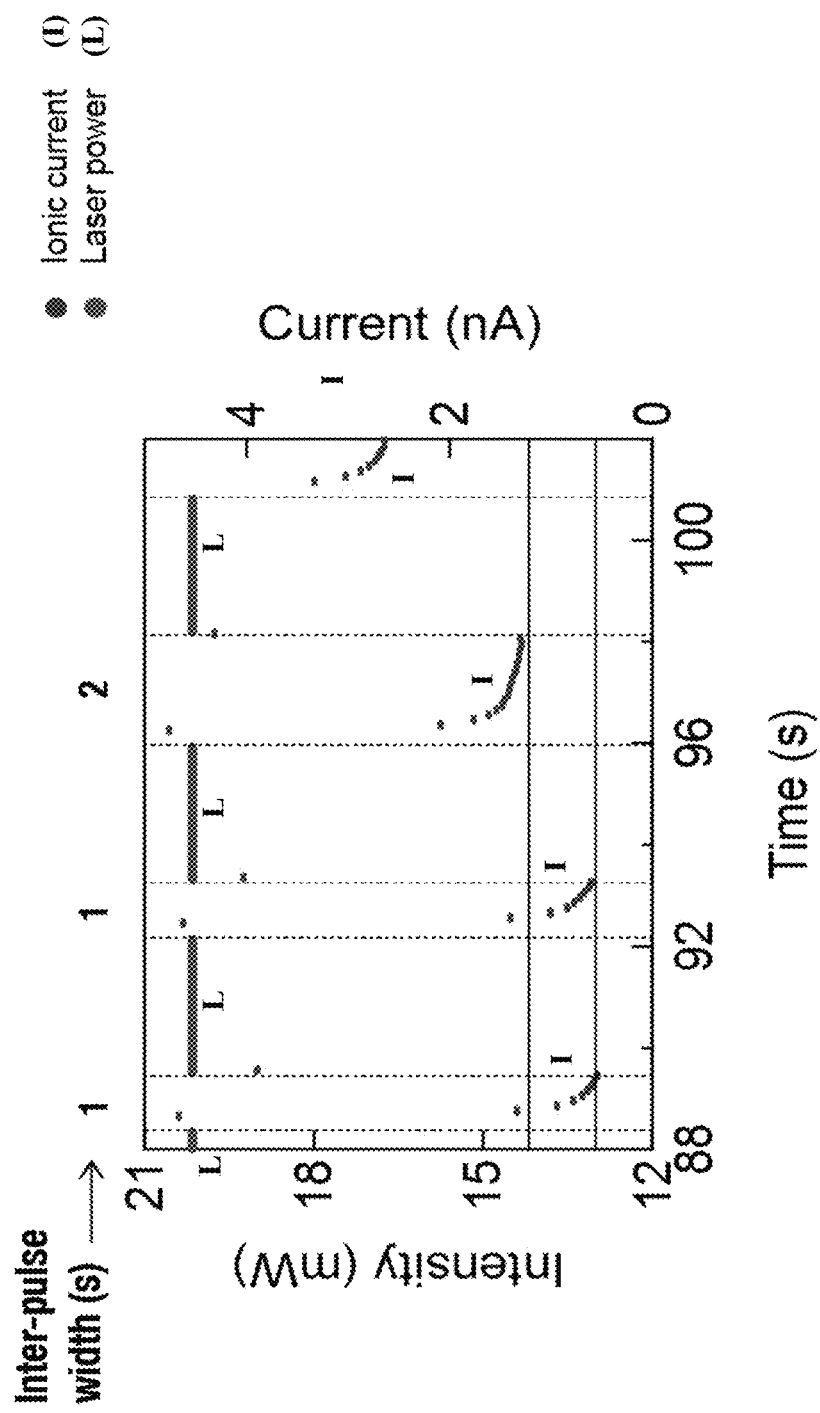

FIGS. 21A-B. NLDA pulse control scenarios. (21A) Example for pulse intensity (P) and duration ($t_{pulse}$) modulation. The 10 pulses demonstrate the differences between "effective and significant" (white square), "effective but insignificant" (white circle) or "ineffective" (black circle). After each two consecutive ineffective pulses (R=2), the intensity and the pulse duration grow by $P^+$ and γ, respectively. After each effective and significant pulse, the power and duration are reduced to $P_0$=12.8 mW and $t_0$=100 ms, respectively. (21B) Inter-pulse delay duration switching example. The periods between pulses are modified by the $\varphi_{TH}$=1 nA threshold. The $1^{st}$ and $2^{nd}$ inter-pulse duration last for $\tau_{IPD}^s$=1 s, allows relatively fast drilling, where the $3^{rd}$, which is above $\varphi_{TH}$, lasts for $\tau_{IPD}^l$=2 s, enables measuring the current in a precise fine-tuning polishing mode.

Figure 22:
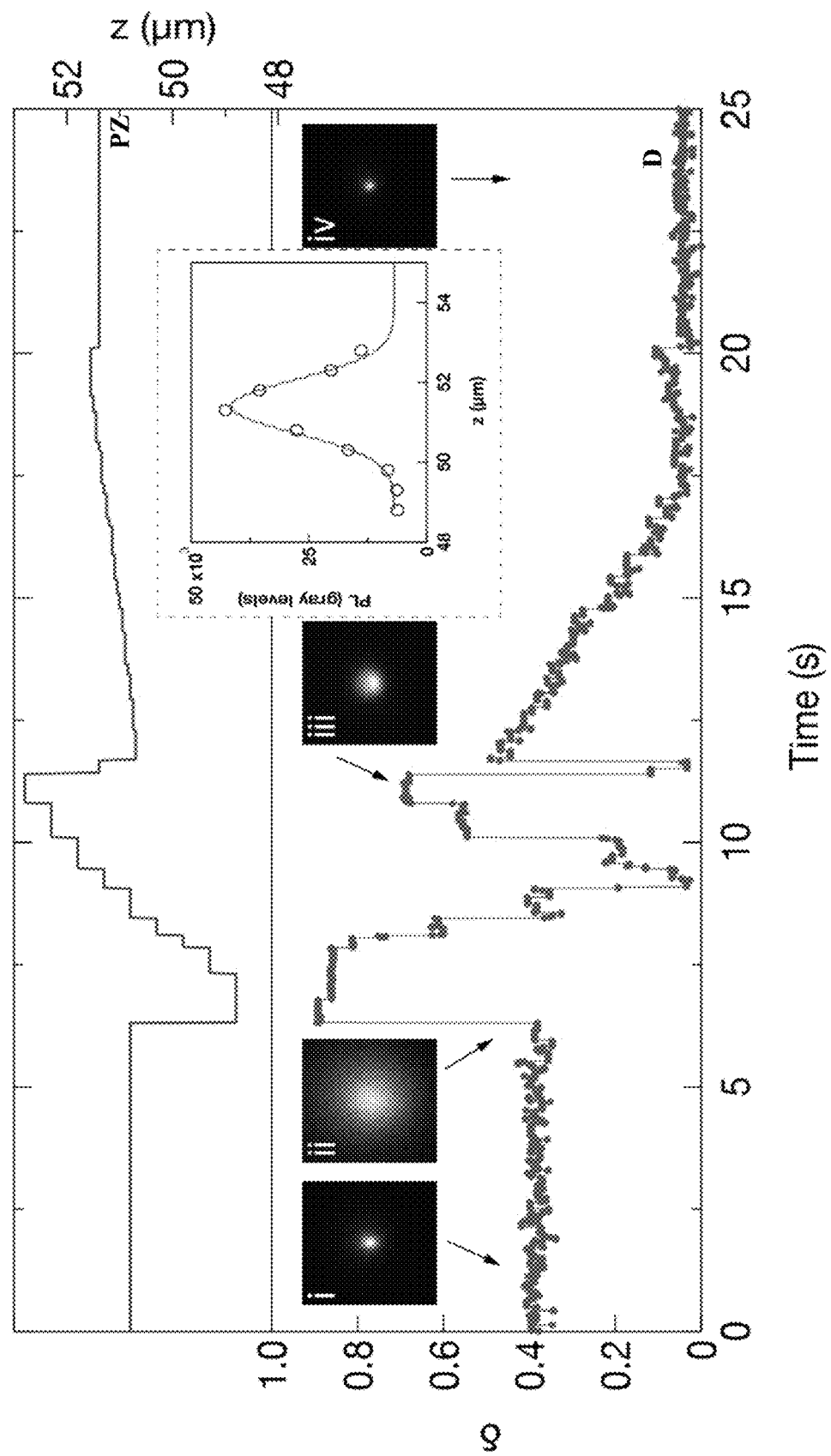

FIG. 22. Laser focusing algorithm. The process attempts to minimize δ, the normalized distance from the focused point (D), which is determined as the z-axial position with the highest photoluminescence (PL) signal. Starting from an arbitrary position along the z-axis (the PL point spread function is imaged in i), by moving the piezo stage (PZ) the algorithm defocuses intentionally (ii) and then scans the z-axis (iii was imaged during the scan). Then, by a Gaussian fitting (inlet), the maximum PL point (δ=0) is found, and the piezo stage is moved to its position (iv). Two fitting steps of coarse- and fine-tuning take place in the focusing process, as the trace implies, where the overall process takes between 10 to 15 s.

Figure 23:
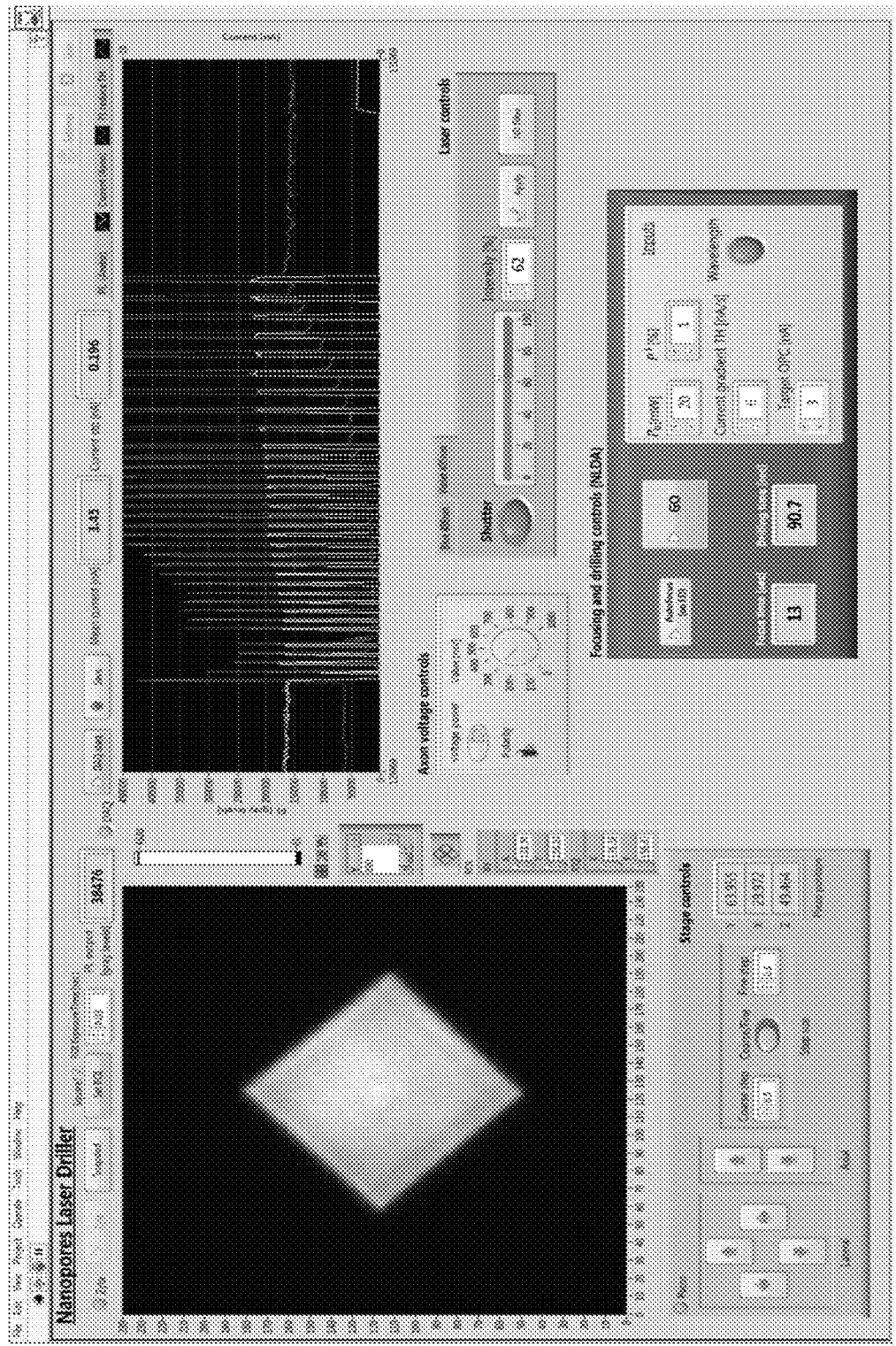

FIG. 23. Nanopore Laser Driller custom LabVIEW software graphical user interface (GUI). The GUI includes: the camera (Andor Zyla) controls, where the membrane and the laser's point spread function (PSF) are imaged; the piezo stage controls to position the PSF on the membrane; the data acquisition (DAQ) display for viewing the photoluminescence (PL) signal together with the current trace; the Axon (Axopatch 200B) voltage controls, for applying a voltage across the nanopore device; the laser controls including shutter, intensity and filters; and the focusing and drilling controls. The last allows one to run the nanopore laser drilling algorithm (NLDA) where its inputs ($P_0$, $P^+$, current gradient threshold $\eta_{TH}$ and Target OPC $I_t$) can be set by the user before running the process. To apply the NLDA, the user simply needs to push the "GO" button.

Figure 24:
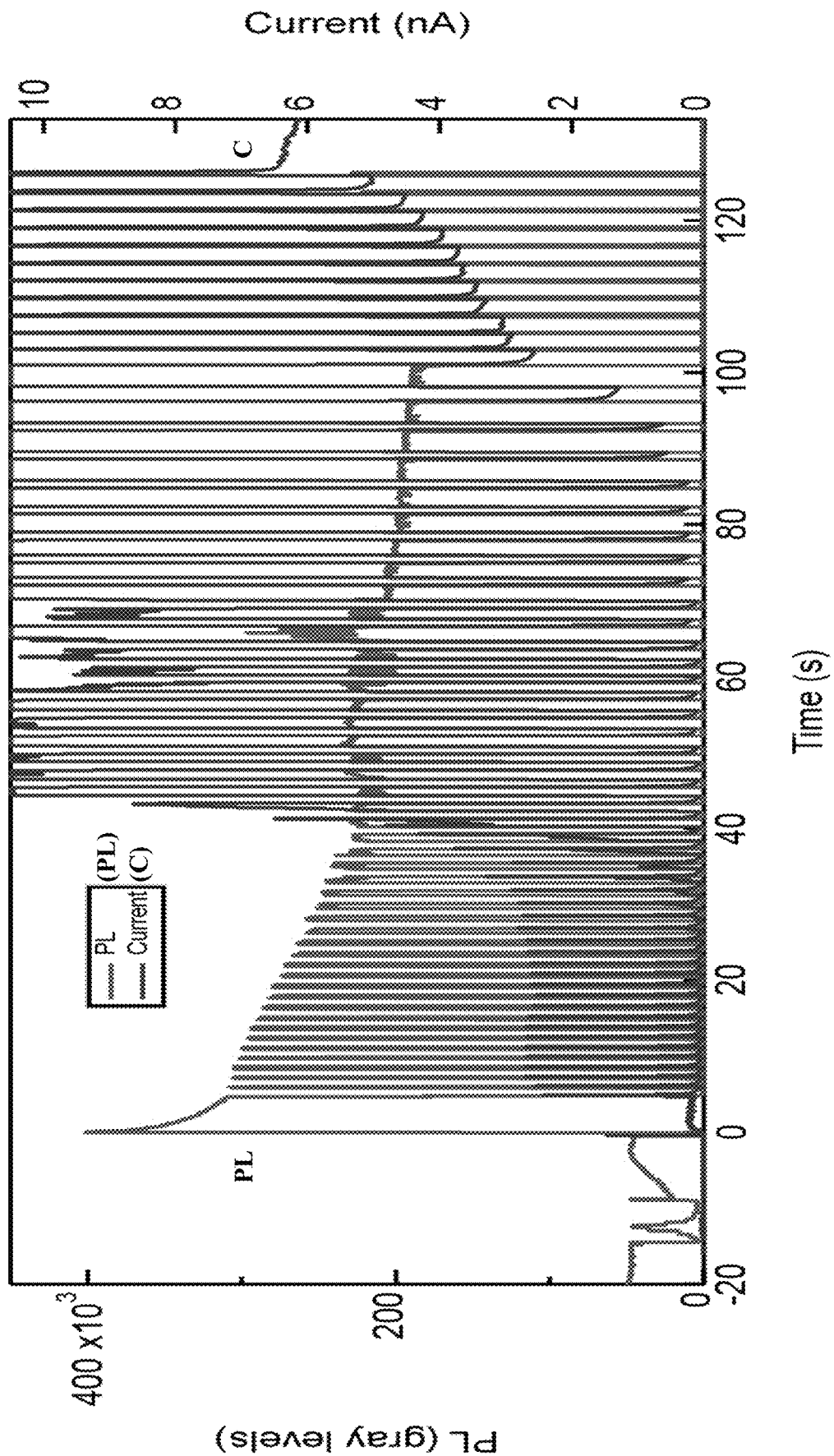

FIG. 24. NLDA raw data recorded for the characteristic trace in FIG. 2. The autofocus trace appears at t<0. The effect of optically-induced current (via electroosmotic flow) is visible producing current overshoots above its maximum range sampled by the A/D card (~10.5 nA). This happens when the laser is ON and the measured photoluminescence (PL) is above the zero level (sCMOS background+dark noise). Thus, the pulsing is essential since the true open pore current is measured when the laser is off.

Figure 4A:
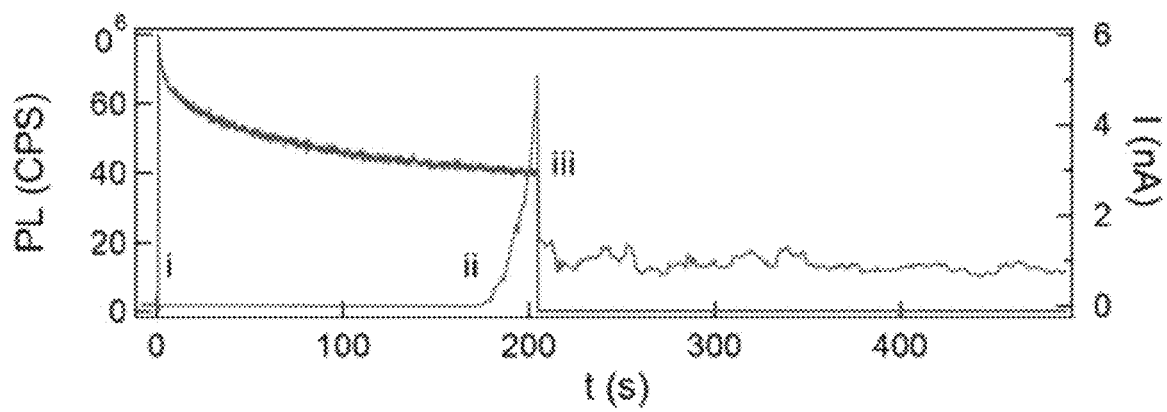
FIGS. 4A-B. Nanopore fabrication by laser-etching. (4A) Measured photoluminescence (PL) and ionic current during laser-exposure (red and grey curves, respectively). The PL sharply increases when the laser is activated (i). Pore formation is signaled by an increase in current (ii). Following ~20 s of pore growth under continued laser-exposure, the laser is deactivated, and the PL returns to zero (iii). Turning off the laser causes a conductivity decrease, resulting in a coincident drop in current which stabilizes over time. (4B) Principle of calcium ($Ca^{2+}$) activators used for verifying the creation of a nanopore (top panels). The entire membrane is illuminated by a 488 nm laser. At −300 mV, $Ca^{2+}$ is driven away from the pore. At +300 mV, $Ca^{2+}$ is driven through the pore where it binds to Fluo-4 resulting in detectable fluorescence at >510 nm. The bottom panels show calcium activators applied to laser-drilled pores. The bias is repeatedly switched between positive and negative to validate the presence of a nanopore.
Figure 25:
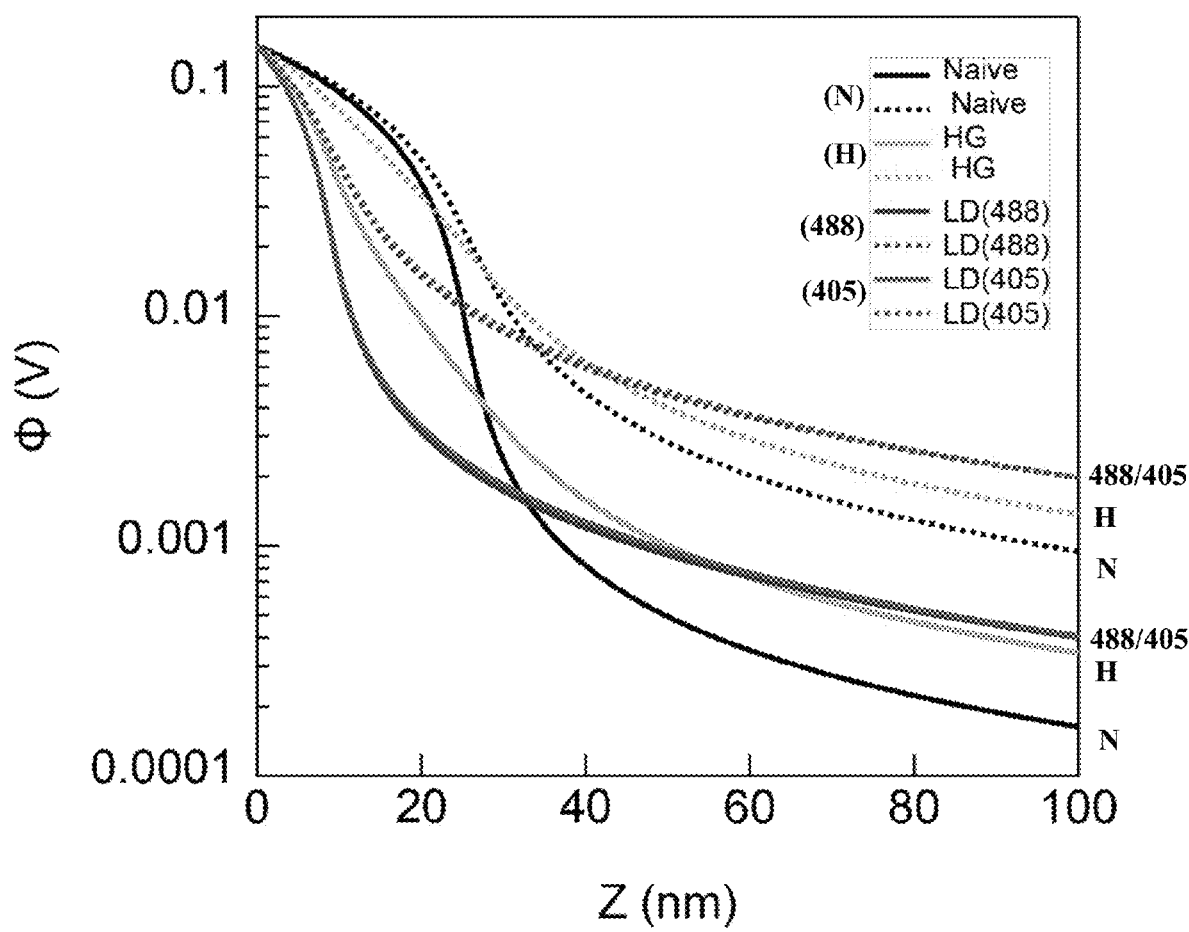

FIG. 25. Numerical simulations results for the electric potential in the line profile described in FIG. 4 (vertical black line, r=0 and z∈[0,100]). The cylindrical (naïve), hourglass (HG) and Gaussian (LD) form factors were evaluated. The solid and dashed lines describe nanopores of d=4.2 nm and d=10.6 nm, respectively. The computations were made for both the λ=405 nm and λ=488 nm lasers' Gaussians.

Figure 26:
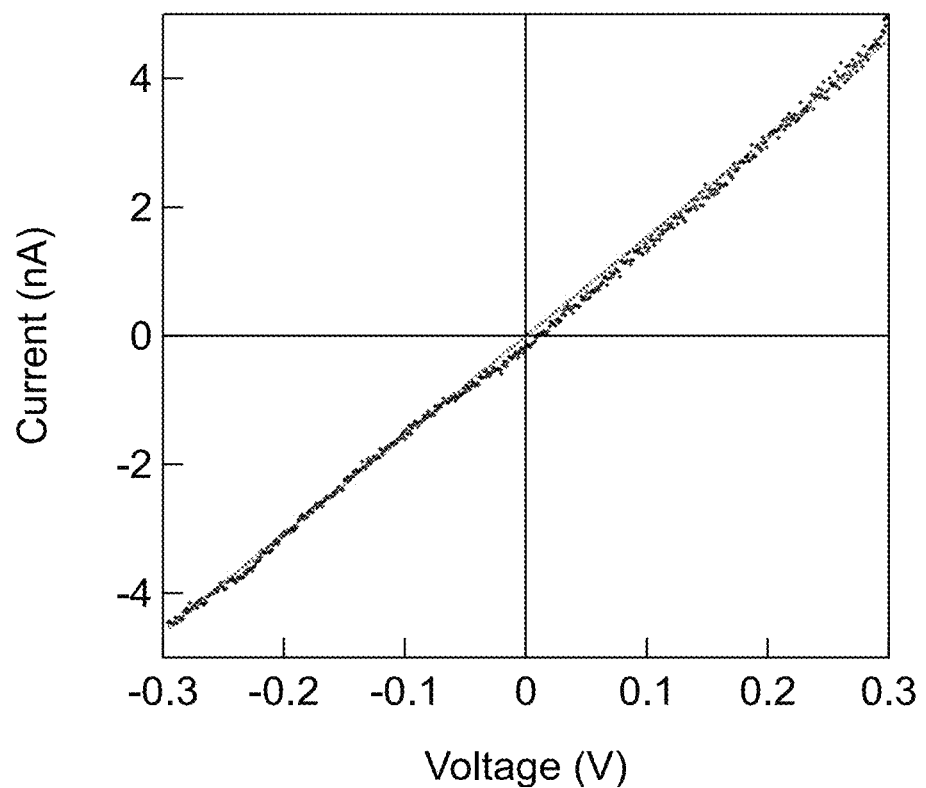

FIG. 26. I-V curve for the pore used in FIG. 19. The curve shows the pore symmetry with a linear fit as expected according to Ohm's law (G=16.36±0.07 nS, Intercept=−0.10±0.01 nA).

Figure 27:
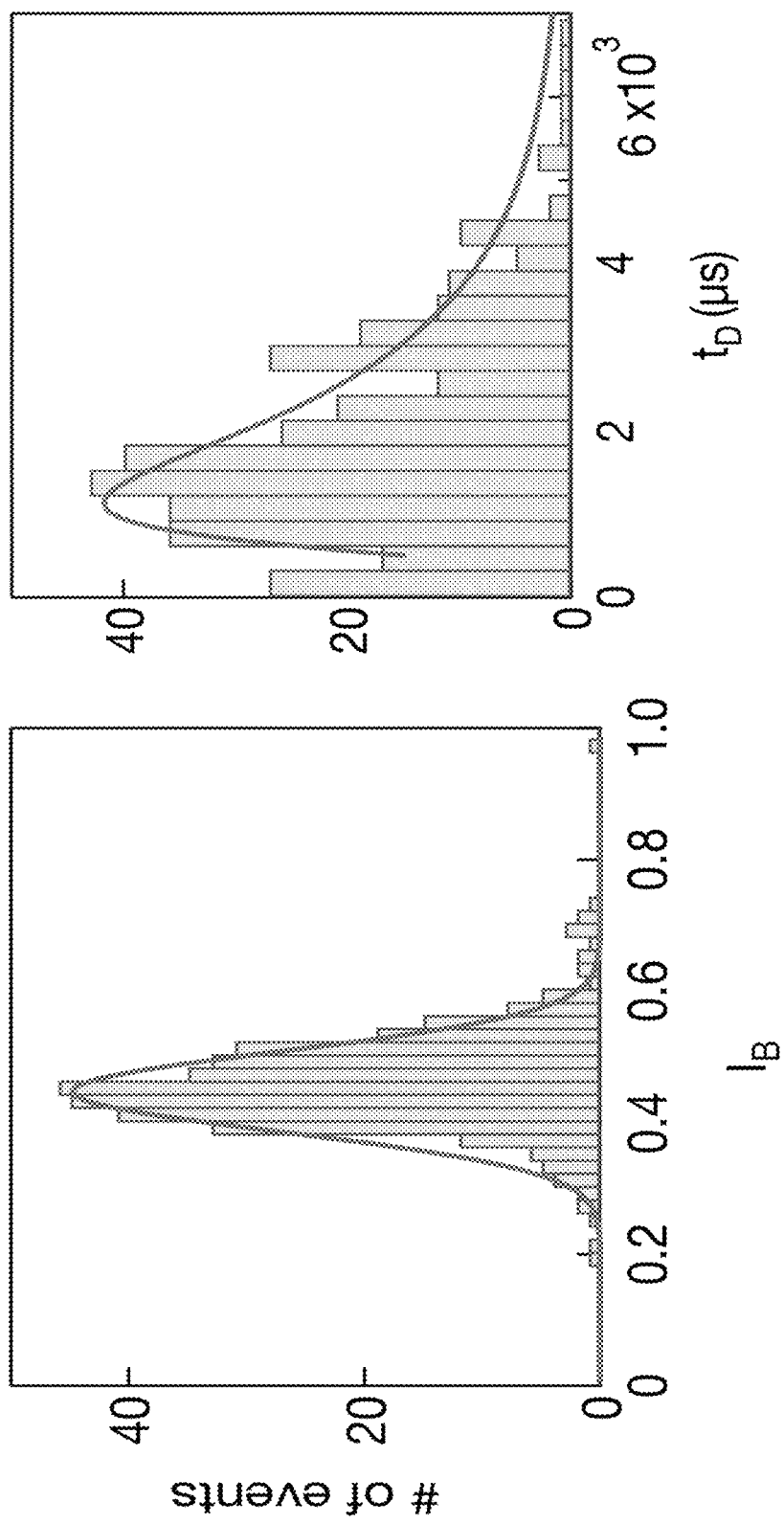

FIG. 27. Event amplitude (left) and dwell time (right) histograms for the SDS-denatured carbonic anhydrase II enzyme translocations experiment in a NLDA nanopore (FIG. 19). Fittings yield mean values of 0.430±0.004 nA and 900±95 μs, respectively.

Figure 28:
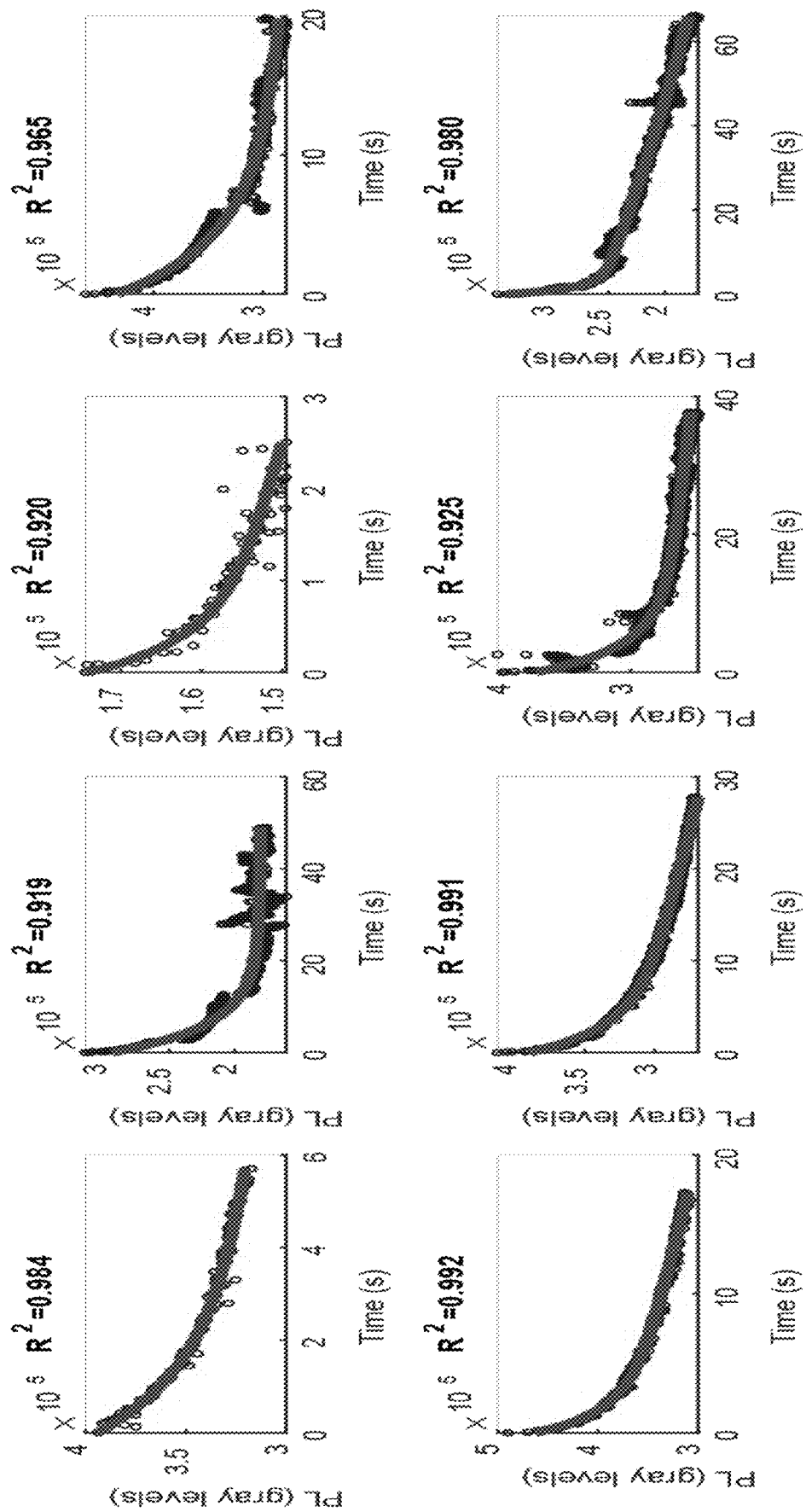
Figure 28:
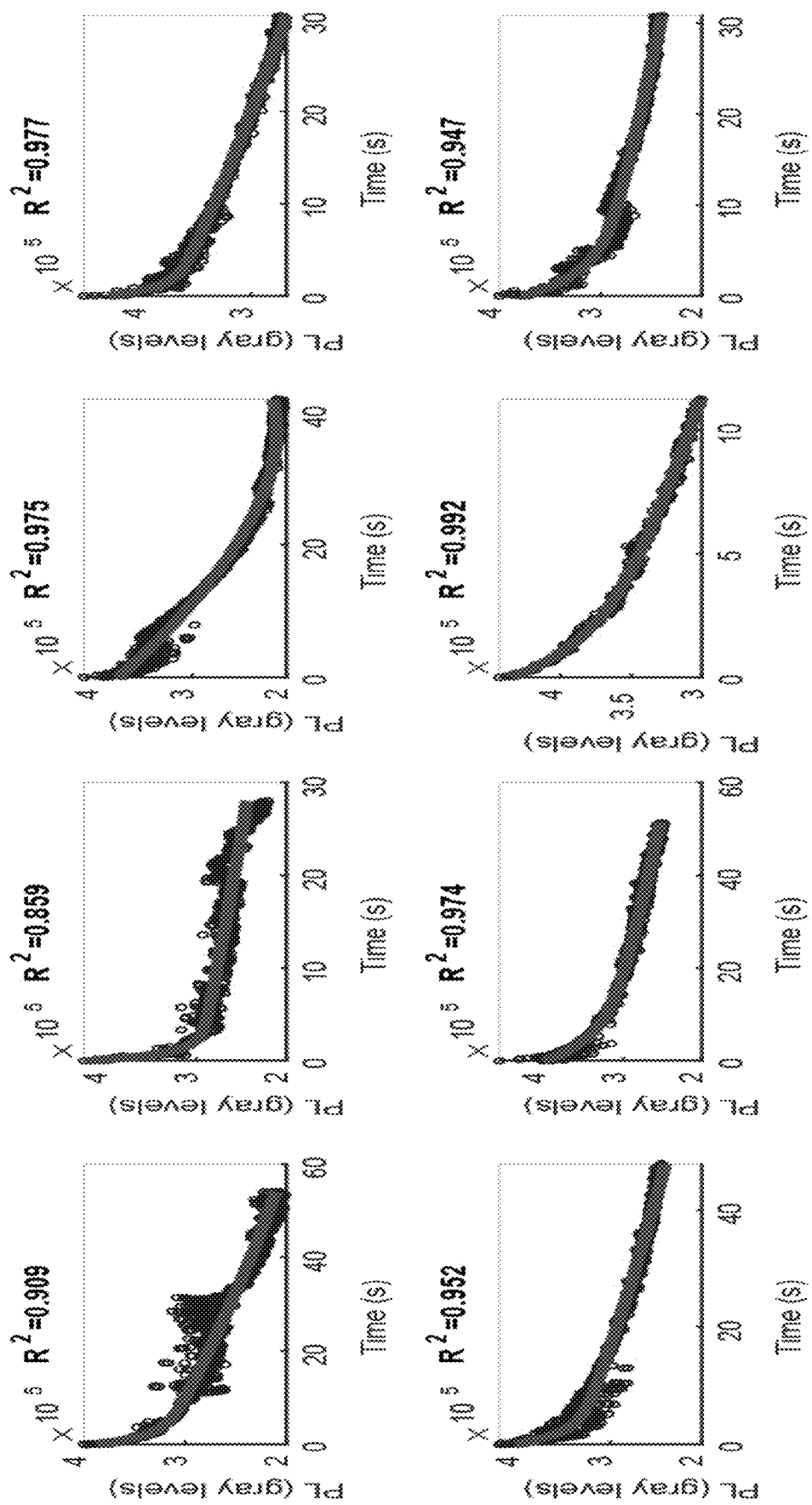

FIG. 28. Typical fitted PL decay traces in the thinning stage of the laser drilling, similar to FIG. 20. Traces are fitted with a two-exponent model. All 25 examples are taken from NLDA experiments. The fitting $R^2$ value for each trace is shown in the titles.

Figure 29B:
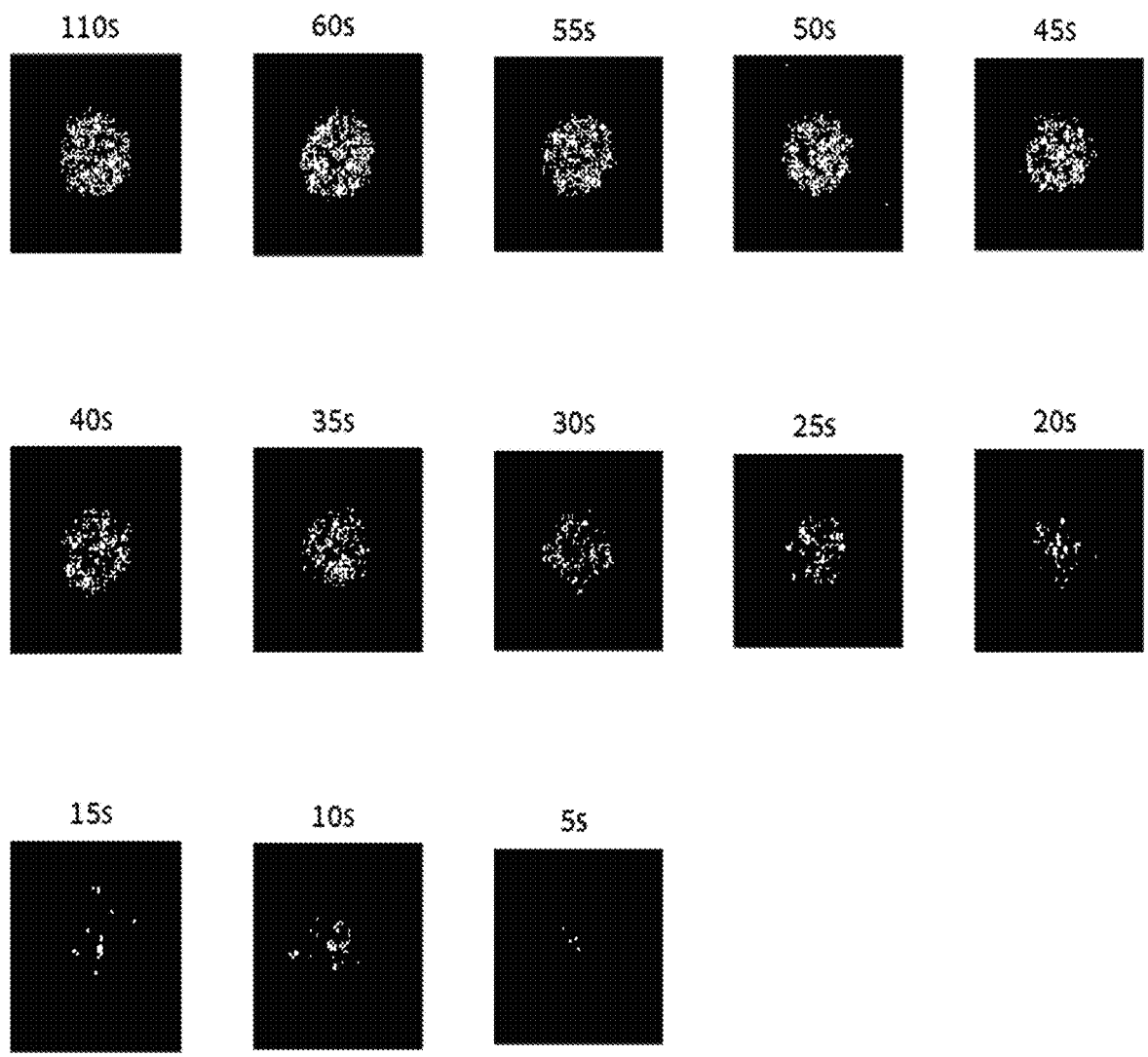

FIGS. 29A-B. Analysis of laser-etched nanowells. (29A) Each of the doses in the original image shown in main FIG. 1a is cropped and isolated. The cropped image inverted gray levels are taken for the next computation, as displayed here. (29B) The images are binarized by a uniform threshold, so only the brighter pixels remain, which are considered as the etched area, and used for the diameter estimation (resulting FIG. 15B).

Figure 30:
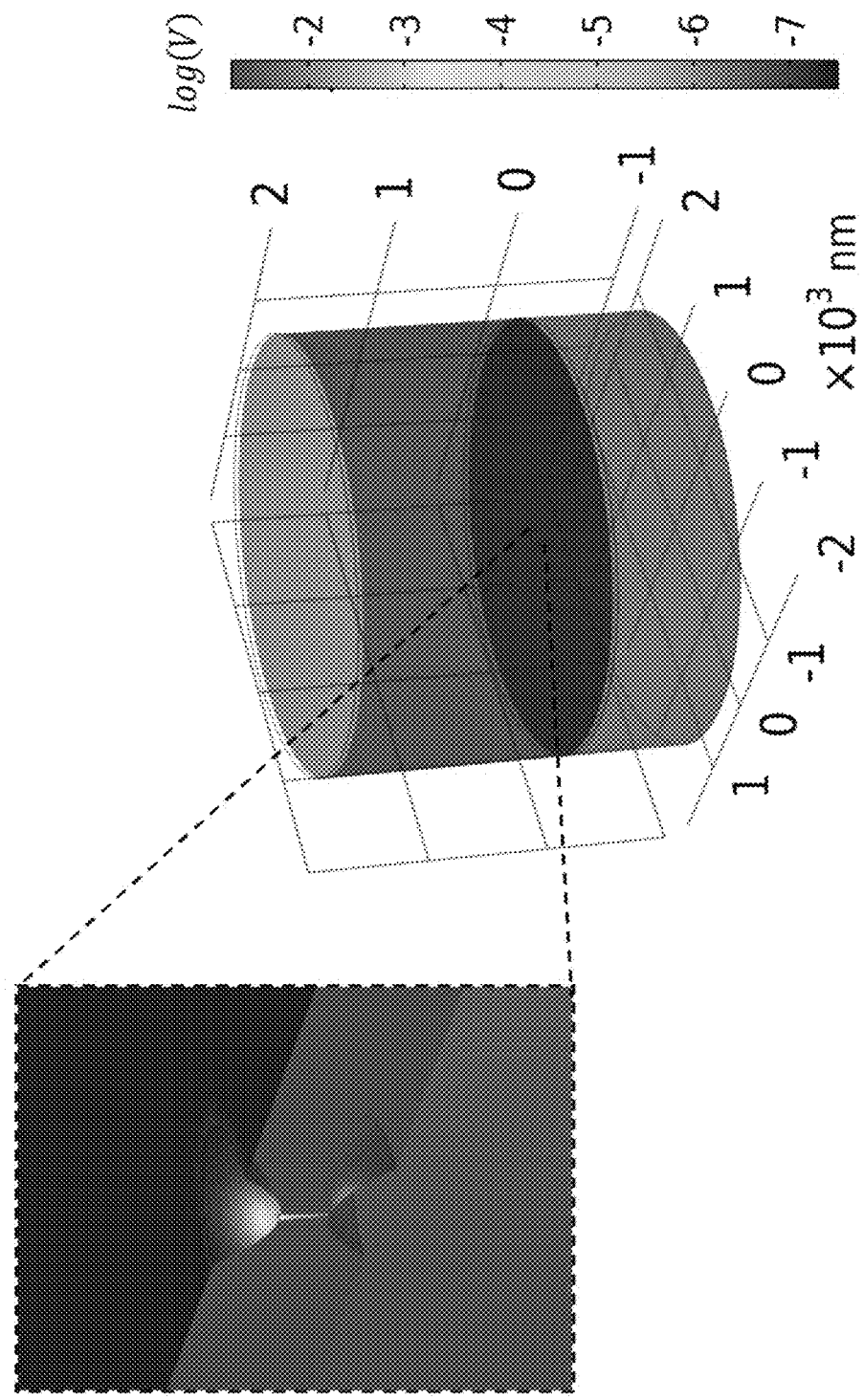

FIG. 30. A representative 3D reconstruction of the simulation with a zoom-in of the Gaussian form factor in the middle of the geometry, The color changes according to the simulated electric potential logarithm.

Figure 31:
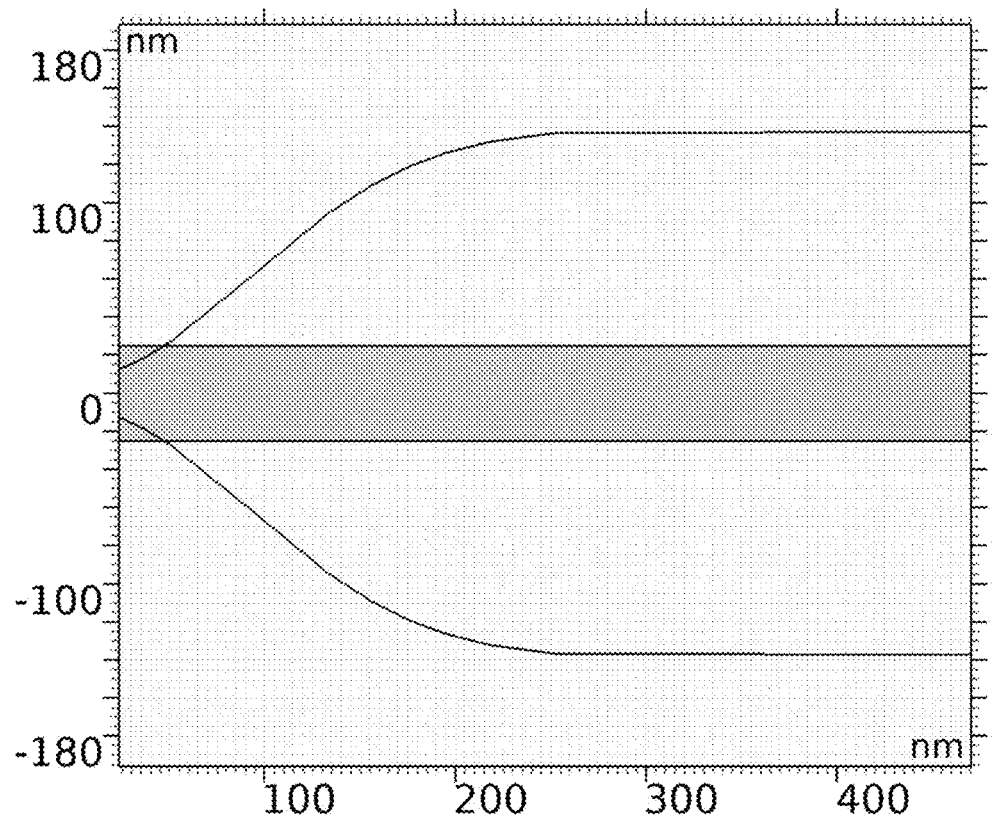

FIG. 31. Back-to-back double Gaussians computed according to equation 4 are intersecting the 50 nm-thick membrane.

Figure 32:
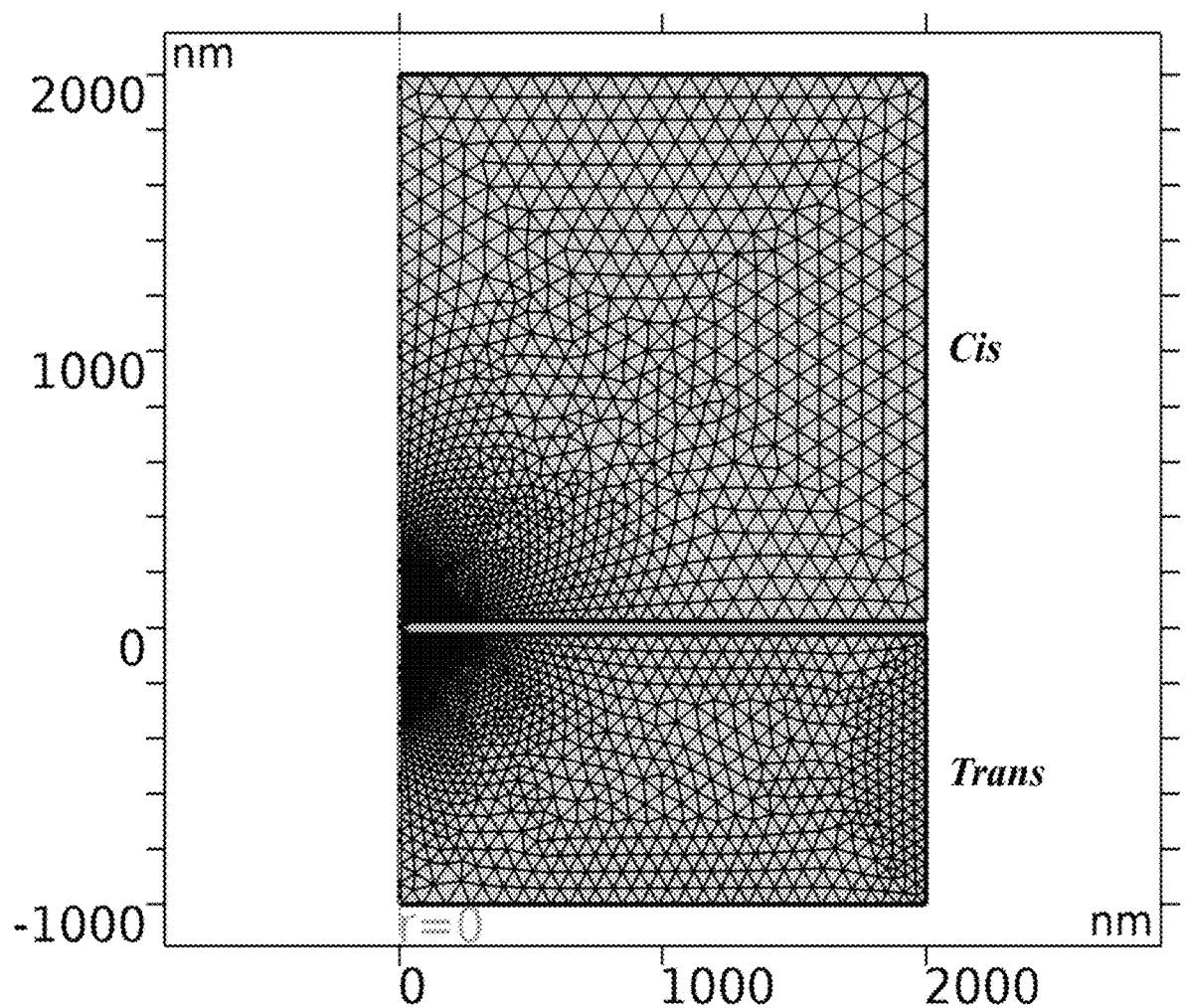

FIG. 32. A typical mesh computed for the simulated geometry. The horizontal rectangle is the membrane and the surrounding area is the solution (top cis and bottom trans reservoirs). The mesh is finer near the nanopore to increase the simulation accuracy and courser far from it to save computation time.

Figure 33:
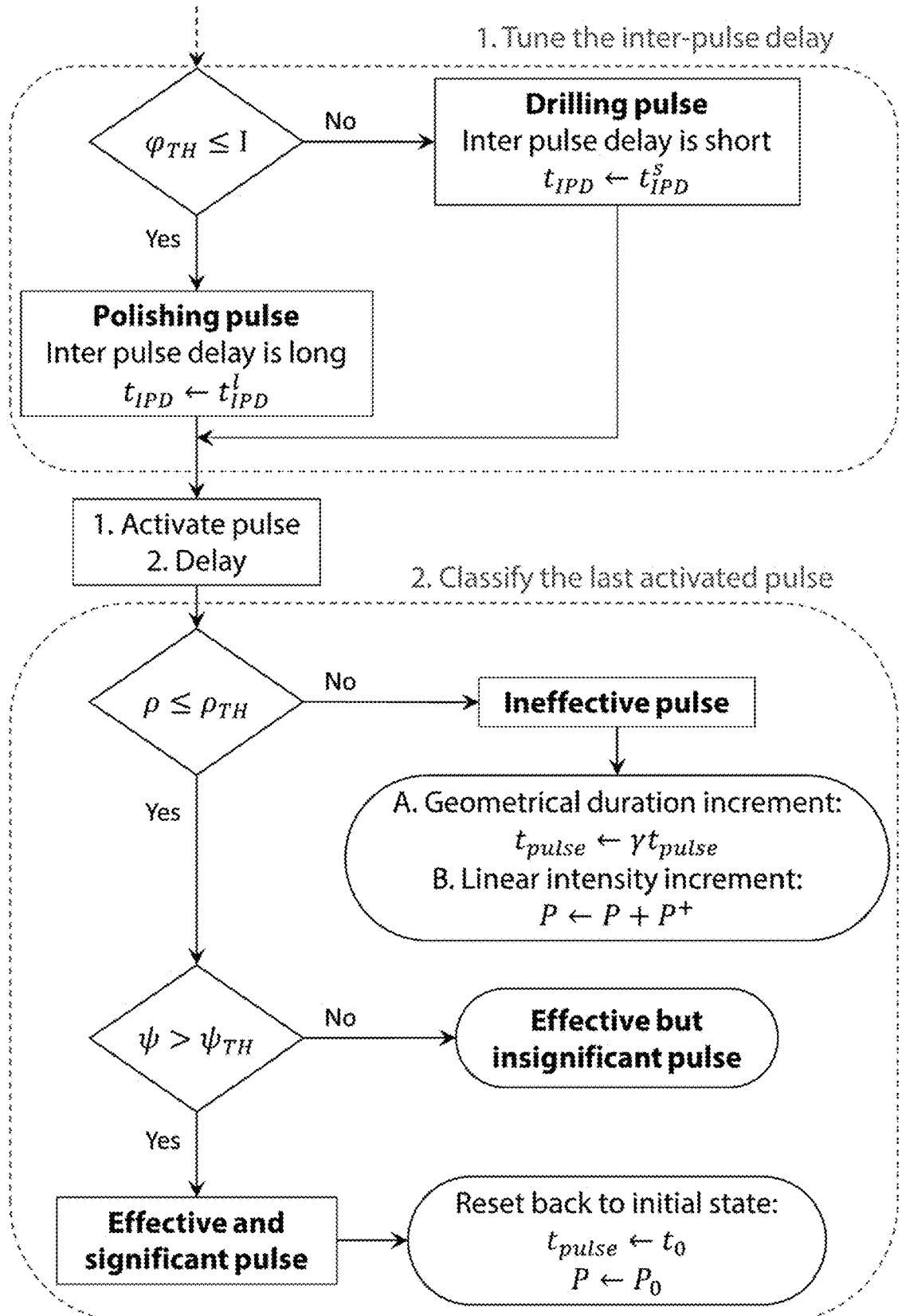

FIG. 33. A flow chart of the steps of a method of the invention.

DETAILED DESCRIPTION OF THE INVENTION

The present invention, in some embodiments, provides systems for light-induced etching a membrane and/or producing a nanopore in a membrane. Methods of thinning and etching a membrane are also provided, as are membranes comprising a nanopore with a Gaussian curve shaped cross-section.

The invention, in some embodiments, further provides methods of generating nanopores of predetermined size, comprising thinning a membrane to produce a pore and then drilling and polishing the produced pore to a predetermined size.

Figure 6A:
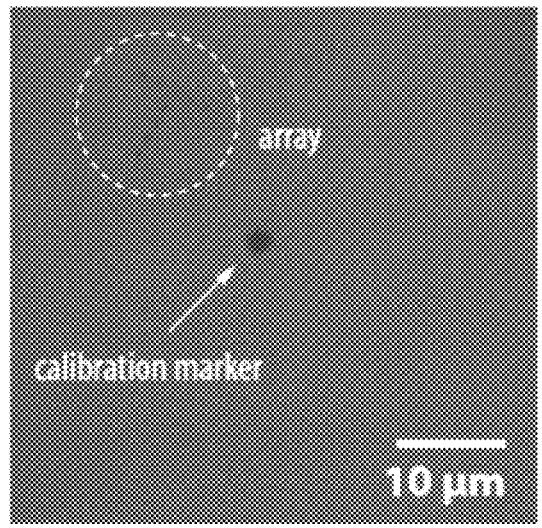
Figure 6B:
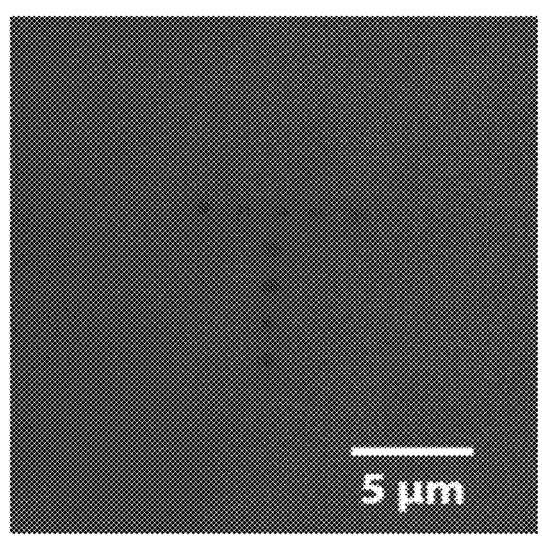
Figure 6C:
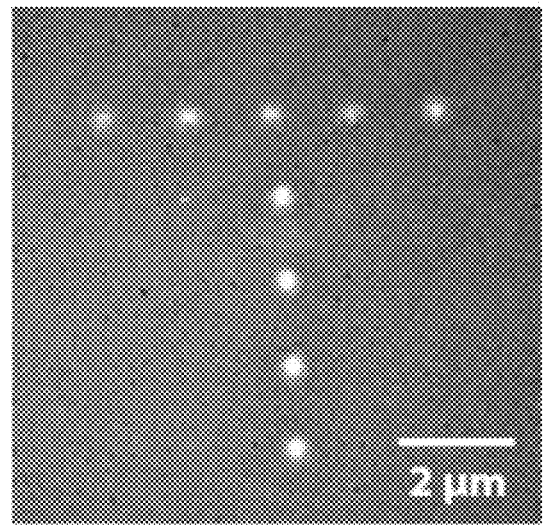
Figure 6D:
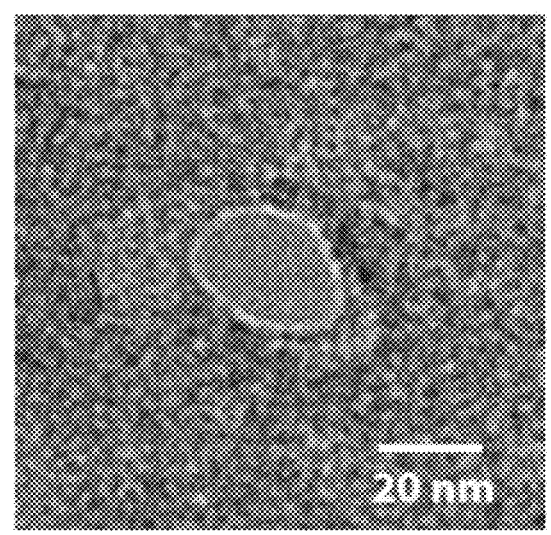

The present invention is based on the unexpected finding that the inventors could perform purely photo-chemical solid-state nanometer-scale pore fabrication with unparalleled in situ control over the nanopore position. Local $SiN_x$ thinning and subsequent pore formation are performed at any arbitrary point along the membrane by simply positioning the membrane at the tightly focused laser spot. To illustrate this, we constructed an evenly spaced, nanoscale-accurate (1500±50 nm center-to-center) T-shape of 9 thin regions in a $SiN_x$ membrane in just 36 minutes (FIG. 6A-C). The T was made next to a lithography-fabricated thin region (20±2 nm) used for thickness calibration and to further prove that the produced contrast is due to thinning (FIG. 6A). The etch time of ~4 minutes per spot was more than enough to produce the visible contrast; under TEM inspection, we found that a ~20 nm nanopore had formed in one of the spots (FIG. 6D). The etch rate is also highly controllable. To show this, we varied the laser intensity in constructing the T: ~30 mW and 45 mW for the top and vertical bars, respectively.

With a blue or green laser and a membrane in water, nanopores can be formed optically in as little as one minute in 45 nm thick $SiN_x$, using a purple laser or increasing pH allowed for significantly faster pore formation. Given that the technique is rapid and highly automatable—it can be monitored by the PL intensity and ionic current—it can be used to construct vast nanopore arrays for massively parallel optical sensing. Notably, as nanopore fabrication proceeds so quickly, it would not be necessary to compromise on the thickness of the supporting membrane, as might be necessary using thickness-limited strategies such as CBD. Furthermore, as a consequence of the inverted-Gaussian etch profile, these nanopores benefit from significantly improved spatial resolution, reduced background PL and improved mechanical robustness.

The inventors further found that both the etching and nanopore drilling kinetics can be accelerated by orders of magnitudes using higher Si to N ratio membranes, measured as a slight increase in their index of refraction. Specifically, a change in the index of refraction of $SiN_x$ membranes from ~2.20 to ~2.40 corresponded to a transition from a practically non-drilling membrane, even after nearly an hour of exposure, to nearly instantaneous nanopore formation. Indeed, when the solution pH was raised to alkaline pH ultra-fast pore formation was observed, even when using a low laser power that could not etch the material at normal pH. Following optimization, drilling yielded single 5 nm pores in 15 seconds from a starting 45 nm thick substrate. Such ultra-fast drilling can be utilized for preparing massive nanopore arrays at any arbitrary position, limited only by light diffraction. As a proof-of-principle, we designed a fully automated feed-back controlled protocol for drilling a 25-nanopore array in about 7 minutes without any user-intervention.

The present invention is also based on the unexpected finding that a sub-wavelength auto-focusing optical design for drilling ssNPs, coupled to an end-to-end multi-step algorithm for controlling the entire drilling process. Importantly, we achieved deterministic ssNP drilling with high accuracy and reproducibility. Specifically, our optimized system can complete the ssNP drilling within 2 minutes from beginning to end, with an error of less than 5% in the open pore conductance corresponding to a sub-nm error in the pore dimensions. We numerically simulated the effect of the Gaussian form-factor of the laser-drilled pores on the electric field distribution and ionic current of the pores. Our results indicate that while the general Ohmic behavior remains similar to TEM-drilled nanopores, the distribution of the electrical field gradient near the pore favors molecule capture due to the wider field distribution in the nanopore vicinity. The open pore current calculated from the simulations were fitted to experimental data to obtain a more realistic approximation of ssNPs conductance dependence on pore diameter, as compared with the widely used theoretical model of ssNP conductance. We validated the functionality of the laser-drilled nanopore by performing translocations of denatured proteins immediately after drilling, such that the entire process of nanopore drilling and single-protein sensing took less than 20 minutes.

Lastly, it was unexpectedly found that pulsed laser light was superior to continuous-wave laser light for thinning and drilling. Shone with the same average power and at the same wavelength, pulsed laser light could thin and drill faster than continuous-wave laser light. Even some membranes that were resistant to etching with a continuous-wave laser could be etched with a pulsed laser.

Systems of the Invention

By a first aspect, there is provided a system comprising, a light source, a membrane, and a system to direct and focus light from the light source to a spot on the membrane.

By another aspect, there is provided a system comprising a light source, an area configured to receive a free-standing membrane, and a system to direct and focus light from the light source to a spot on a received free-standing membrane.

In some embodiments, the light source produces coherent light. In some embodiments, the light source produces collimated light. In some embodiments, the light source produces coherent and collimated light. In some embodiments, the light source produces a coherent and collimated light beam. In some embodiments, the light source is a laser or light emitting diode (LED). In some embodiments, the light source is a laser. In some embodiments, the laser is a solid-state laser. In some embodiments, the laser is a gas laser. In some embodiments, the laser is a wave laser. In some embodiments, the laser is a continuous-wave laser. In some embodiments, the laser is a pulsed laser. In some embodiments, a pulsed laser is a pico-second pulsed laser. In some embodiments, the laser is a focused laser. In some embodiments, the laser light is continuous-wave laser light. In some embodiments, the laser light is continuous laser light. In some embodiments, the laser light is pulsed laser light. In some embodiments, the laser light is continuous wave focused laser light.

In some embodiments, the light source is a monochromatic light source. In some embodiments, the light source is configured to produce monochromatic light. In some embodiments, the light source produces purple, blue and/or green light. In some embodiments, the light source produces purple light. In some embodiments, purple light is violet light. In some embodiments, the light source produced blue light. In some embodiments, the light source produced green light. In some embodiments, the light source produced blue and/or green light. In some embodiments, purple light comprises a wavelength between 380 and 420 nm. In some embodiments, purple light comprises a wavelength between 380 and 450 nm. In some embodiments, purple light comprises a wavelength between 400 and 420 nm. In some embodiments, purple light comprises a wavelength between 400 and 450 nm. In some embodiments, blue light comprises a wavelength between 380 and 490 nm. In some embodiments, blue light comprises a wavelength between 420-490 nm. In some embodiments, blue light comprises a wavelength between 450-490 nm. In some embodiments, blue light comprises a wavelength between 380 and 500 nm. In some embodiments, blue light comprises a wavelength between 420-500 nm. In some embodiments, blue light comprises a wavelength between 450-500 nm. In some embodiments, blue light comprises a wavelength between 380 and 520 nm. In some embodiments, blue light comprises a wavelength between 420-520 nm. In some embodiments, blue light comprises a wavelength between 450-520 nm. In some embodiments, green light comprises a wavelength between 500 and 580 nm. In some embodiments, green light comprises a wavelength between 520 and 580 nm. In some embodiments, green light comprises a wavelength between 500 and 560 nm. In some embodiments, green light comprises a wavelength between 520 and 560 nm. In some embodiments, the light source is configured to emit light at a wavelength between 380 and 580 nm. In some embodiments, the light source is configured to emit light at a wavelength between 300 and 580 nm. the light source is configured to emit light at a wavelength between 380 and 600 nm. In some embodiments, the light source is configured to emit light at a wavelength between 300 and 600 nm. In some embodiments, the laser light is at a wavelength of between 300 and 600 nm.

In some embodiments, the power of the light source is at most 100, 95, 90, 85, 80, 75, 70, 65, 60, 55, 50, 45, 40, 35, 30, 25, 20, 25, 20, 15, 10, 5, 1, 0.5, 0.1, 0.05, 0.01, 0.005, or 0.001 milliwatts (mW). Each possibility represents a separate embodiment of the invention. In some embodiments, the power of the light source is at least 1, 10, 100, 200, 300, 400, 500, 600, 700, 800, 900, or 1000 micro-watts (μW). Each possibility represents a separate embodiment of the invention. In some embodiments, the power of the light source is at least 1 μW. In some embodiments, the power of the light source is at least 10 μW. In some embodiments, the power of the light source is at least 100 μW. In some embodiments, the power of the light source is at least 1 mW. In some embodiments, the power of the light source is between 1 μW and 50 mW, 1 μW and 45 mW, 1 μW and 40 mW, 1 μW and 35 mW, 1 μW and 30 mW, 1 μW and 25 mW, 1 μW and 20 mW, 1 μW and 15 mW, 1 μW and 1 mW, 1 μW and 5 mW, 1 μW and 1 mW, 10 μW and 50 mW, 10 μW and 45 mW, 10 μW and 40 mW, 10 μW and 35 mW, 10 μW and 30 mW, 10 μW and 25 mW, 10 μW and 20 mW, 10 μW and 15 mW, 10 μW and 10 mW, 10 μW and 5 mW, 10 μW and 1 mW, 100 μW and 50 mW, 100 μW and 45 mW, 100 μW and 40 mW, 100 μW and 35 mW, 100 μW and 30 mW, 100 μW and 25 mW, 100 μW and 20 mW, 100 μW and 15 mW, 100 μW and 10 mW, 100 μW and 5 mW, 100 μW and 1 mW, 200 μW and 50 mW, 200 μW and 45 mW, 200 μW and 40 mW, 200 μW and 35 mW, 200 μW and 30 mW, 200 μW and 25 mW, 200 μW and 20 mW, 200 μW and 15 mW, 200 μW and 10 mW, 200 μW and 5 mW, 200 μW and 1 mW, 300 μW and 50 mW, 300 μW and 45 mW, 300 μW and 40 mW, 300 μW and 35 mW, 300 μW and 30 mW, 300 μW and 25 mW, 300 μW and 20 mW, 300 μW and 15 mW, 300 μW and 10 mW, 300 μW and 5 mW, 300 μW and 1 mW, 400 μW and 50 mW, 400 μW and 45 mW, 400 μW and 40 mW, 400 μW and 35 mW, 400 μW and 30 mW, 400 μW and 25 mW, 400 μW and 20 mW, 400 μW and 15 mW, 400 μW and 10 mW, 400 μW and 5 mW, 400 μW and 1 mW, 500 μW and 50 mW, 500 μW and 45 mW, 500 μW and 40 mW, 500 μW and 35 mW, 500 μW and 30 mW, 500 μW and 25 mW, 500 μW and 20 mW, 500 μW and 15 mW, 500 μW and 10 mW, 500 μW and 5 mW, 500 μW and 1 mW, 1 mW and 50 mW, 1 mW and 45 mW, 1 mW and 40 mW, 1 mW and 35 mW, 1 mW and 30 mW, 1 mW and 25 mW, 1 mW and 20 mW, 1 mW and 15 mW, 1 mW and 10 mW and 1 mW and 5 mW. Each possibility represents a separate embodiment of the invention. In some embodiments, the power of the light source is between 1 mW and 45 mW. A person skilled in the art will appreciate that as the wavelength of the light is decreases the power can be decreased without a deleterious effect on the ability of the system to etch. Thus, a purple light at a lower power can etch at the same rate as a green light at a higher power, for non-limiting example. In some embodiments, the power of the light source is the intensity of the light at a spot on the membrane. In some embodiments, the light source is configured to produce the intensity of light at a spot on the membrane. In some embodiments, the spot is on the first layer. In some embodiments, the first spot is on the first layer. In some embodiments, the second spot is on the second layer.

In some embodiments, a pulsed laser produces pulse widths of between 50-150 picoseconds (ps). In some embodiments, pulsed laser light comprises pulse widths of between 50-150 ps. In some embodiments, a pulsed laser produces pulse widths of at least 20, 30, 40, 50, 60, 70, 80, 90 100, 110, 120, 130, 140, or 150 ps. Each possibility represents a separate embodiment of the invention. In some embodiments, pulsed laser light comprises pulse widths of at least 20, 30, 40, 50, 60, 70, 80, 90 100, 110, 120, 130, 140, or 150 ps. Each possibility represents a separate embodiment of the invention. In some embodiments, a pulsed laser produces pulse widths of at most 50, 60, 70, 80, 90 100, 110, 120, 130, 140, 150, 160, 170, 180, 190, 200, 210, 220, 230, 240, 250, 260, 270, 280, 290 or 300 ps. Each possibility represents a separate embodiment of the invention. In some embodiments, pulsed laser light comprises pulse widths of at most 50, 60, 70, 80, 90 100, 110, 120, 130, 140, 150, 160, 170, 180, 190, 200, 210, 220, 230, 240, 250, 260, 270, 280, 290 or 300 ps. Each possibility represents a separate embodiment of the invention. In some embodiments a pulsed laser produces pulse widths or pulsed laser light comprises pulse widths of between 40-200, 40-180, 40-160, 40-150, 10-140, 10-130, 40-120, 40-110, 40-100, 40-90, 40-80, 40-70, 40-60, 50-200, 50-180, 50-160, 50-150, 50-140, 50-130, 50-120, 50-110, 50-100, 50-90, 50-80, 50-70, 50-60, 60-200, 60-180, 60-150, 60-140, 60-130, 60-120, 60-110, 60-100, 60-90, 60-80, 60-70, 70-200, 70-180, 70-160, 70-150, 70-140, 70-130, 70-120, 70-110, 70-100, 70-90, 70-80, 80-200, 80-180, 80-160, 80-150, 80-140, 80-130, 80-120, 80-110, 80-100, 80-90, 90-200, 90-180, 90-160, 90-150, 90-140, 90-130, 90-120, 90-110, 90-100, 100-200, 100-180, 100-160, 100-150, 100-140, 100-130, 100-120, 100-110, 100-200, 110-180, 110-160, 110-150, 110-140, 110-130, 110-120, 120-200, 120-180, 120-160, 120-150, 120-140, 120-130, 130-200, 130-180, 130-160, 130-150, 130-140, 140-200, 140-180, 140-160, 140-150, 150-200, 150-180, or 150-160. Each possibility represents a separate embodiment of the invention.

In some embodiments, a pulsed laser pulses with a repetition rate of up to 80 mega Hertz (MHz). In some embodiments, pulsed laser light comprises a repetition rate of up to 80 MHz. In some embodiments, a pulsed laser pulses with a repetition rate of up to 20, 30, 40, 50, 60, 70, 75, 80, 90 or 100 MHz. Each possibility represents a separate embodiment of the invention. In some embodiments, pulsed laser light comprises a repetition rate of up to 20, 30, 40, 50, 60, 70, 75, 80, 90 or 100 MHz. Each possibility represents a separate embodiment of the invention. In some embodiments, a pulsed laser pulses with a repetition rate of not more than 40, 50, 60, 70, 80, 90 or 100 MHz. Each possibility represents a separate embodiment of the invention. In some embodiments, pulsed laser light comprises a repetition rate of not more than 40, 50, 60, 70, 80, 90 or 100 MHz. Each possibility represents a separate embodiment of the invention. In some embodiments, a pulsed laser pulses with a repetition rate or pulsed laser light comprises a repetition rate of between 20-100, 20-90, 20-80, 20-70, 20-60, 20-50, 20-40, 30-100, 30-90, 30-80, 30-70, 30-60, 30-50, 30-40, 40-100, 40-90, 40-80, 40-70, 40-60, 40-50, 50-100, 50-90, 50-80, 50-70, 50-60, 60-100, 60-90, 60-80, 60-70, 70-100, 70-90, 70-80, 80-100 or 80-90 MHz. Each possibility represents a separate embodiment of the invention.

As used herein, the terms "film" and "membrane" are used interchangeably and refer to a thin water-impermeable layer of material. In some embodiments, the membrane is ion-impermeable. In some embodiments, the membrane is insulated. In some embodiments, the membrane is electrically insulated. In some embodiments, the membrane is mechanically robust. In some embodiments, mechanically robust refers to physical strength. In some embodiments, the membrane comprises a tensile strength of at least 100, 150, 200, 250, 275, 300, 325, 350, 375, 400, 450 or 500 mega pascals (MPa). Each possibility represents a separate embodiment of the invention. In some embodiments, the membrane comprises a tensile strength of at least 300 mega pascals (MPa). In some embodiments, the membrane is chemically inert. In some embodiments, chemically inert comprises difficult to etch by organic solvent or aqueous based acids or bases. In some embodiments, the membrane is free-standing. In some embodiments, the membrane is freely standing. In some embodiments, a free-standing membrane is immersed in an aqueous solution. In some embodiments, a free-standing membrane is surrounded on both sides by an aqueous solution. In some embodiments, a free-standing membrane is covered by aqueous solution on both sides. In some embodiments, both sides are two drillable sides. In some embodiments, both sides the side upon which the light is shone and the side upon which light exits when a pore is drilled. It will be understood by a stilled artisan that the sides of the membrane that are not being drilled do not need to be covered by the aqueous solution. Rather, the spot where the light is shone needs to be covered by the aqueous solution, and if the laser spot is considered three dimensionally to pass through the membrane, the spot on the opposite side of the membrane must also be covered by the aqueous solution. A laser spot has a thickness (~300 nm) that is thicker than the width of the membrane. Thus, the "spot" on the membrane actually is a three-dimensional spot that extends through the entire width of the membrane. Thus, the laser spot is on both sides of the membrane and both sides of the spot are immersed in an aqueous solution. In some embodiments, a free-standing membrane comprises both sides of the spot on the membrane covered by an aqueous solution. In some embodiments, a free-standing membrane comprises access of an aqueous solution over both sides of the spot on the membrane. In some embodiments, the laser spot on the first side of the membrane is a first spot. In some embodiments, the laser spot on the second side of the membrane is a second spot. In some embodiments, the spot is a first spot. In some embodiments, the spot is a second spot. In some embodiments, the spot is a first spot and a second spot. In some embodiments, a free-standing membrane comprises access of an aqueous solution over a first spot on the membrane. In some embodiments, a free-standing membrane comprises access of an aqueous solution over a second spot on the membrane. In some embodiments, the first spot and the second spot are on opposite sides of the membrane. In some embodiments, the first spot and the second spot are positioned such that a line passing through the membrane passes through the first spot and the second spot. In some embodiments, a free-standing membrane comprises an aqueous solution over a first spot on the membrane. In some embodiments, a free-standing membrane comprises an aqueous solution over a second spot on the membrane.

In some embodiments, the membrane comprises a first layer. In some embodiments, the membrane comprises silicon. In some embodiments, the first layer comprises silicon. In some embodiments, the membrane or first layer is silicon based. In some embodiments, the membrane or first layer comprises silicon nitride ($SiN_x$). As used herein, the terms "$SiN_x$" and "$Si_xN$" are used interchangeably and refer to silicon nitride. The "x" refers to the ratio of silicon to nitride which is variable in the substance. In some embodiments, the silicon nitride is amorphous silicon nitride. In some embodiments, amorphous silicon nitride is one with a variable ratio of silicon to nitride.

In some embodiments, membrane comprises a second layer. In some embodiments the film comprises a metal oxide. In some embodiments, the second layer is a layer of metal oxide. In some embodiments, the metal oxide is selected from aluminum oxide ($AlO_2$), titanium oxide ($TiO_2$), silicon oxide ($SiO_2$) and hafnium oxide ($HfO_2$). In some embodiments, the metal oxide is selected from aluminum oxide ($AlO_2$), titanium oxide ($TiO_2$), and hafnium oxide ($HfO_2$). In some embodiments, the metal oxide is $TiO_2$. In some embodiments, membrane or second layer comprises amorphous silicon nitride. In some embodiments, the silicon nitride is amorphous silicon nitride. In some embodiments, the membrane or second layer comprises silicon nitride, titanium dioxide or a combination thereof. In some embodiments, the membrane comprises more than one layer. In some embodiments, the membrane comprises a layer of $SiN_x$. In some embodiments, the membrane comprises a layer of $TiO_2$. In some embodiments, the membrane comprises a layer of $TiO_2$ layered on a layer of $SiN_x$. In some embodiments, the second layer is layered on the first layer. In some embodiments, the second layer is a dielectric layer.

As used herein, the term "layer" refers to a thin flat continuous piece of material. In some embodiments, the layer comprises a metallic layer having plasmonic properties. In some embodiments, the layer comprises a metal. In some embodiments, the metal is selected from gold, silver, copper, aluminum, titanium, hafnium and a combination thereof. In some embodiments, the metallic layer comprises at least one layer of metal. In some embodiments, the metallic layer comprises more than one layer of metal. In some embodiments, the more than one layer of metal is layered one on top of the other to create one combined metallic layer. In some embodiments, the layer comprises a metal oxide. In some embodiments, the layer is a silicon layer. In some embodiments, the layer is a layer that comprises silicon. In some embodiments, the layer is a silicon nitride layer. In some embodiments, a layer is deposited by Atomic Layer Deposition (ALD). In some embodiments, one layer is deposited upon another by ALD.

In some embodiments, the second layer is refractory to etching. In some embodiments, the second layer is refractory to thinning. In some embodiments, the second layer is refractory when not layered on the first layer. In some embodiments, the second layer when layered on the first layer can be etched or thinned. In some embodiments, the second layer is layered on the first layer.

In some embodiments, the membrane is deposited on a silicon wafer. In some embodiments, the membrane is formed from a silicon wafer. In some embodiments, the wafer is a crystal orientation wafer. In some embodiments, the wafer is thicker in regions that lack a nanopore. In some embodiments, the wafer comprises a diameter of at least 1, 10, 50, 75, 100 or 200 mm. Each possibility represents a separate embodiment of the invention. In some embodiments, the wafer comprises a thickness of at least 50, 100, 150, 200, 250, 300, 350 or 400 μm. Each possibility represents a separate embodiment of the invention.

In some embodiments, the membrane or first layer has a universal thickness. In some embodiments, the membrane or first layer has a constant thickens across its entire area. In some embodiments, the membrane or first layer has a variable thickness. In some embodiments, the membrane or first layer is thinner in the area of the nanopore. In some embodiments, the membrane or first layer does not comprise a thickness of less than 100, 90, 80, 75, 70, 60, 50, 45, 40, 35, 30, 25, 20, 15, 10, or 5 nm. Each possibility represents a separate embodiment of the invention. In some embodiments, the membrane or first layer does not comprise a thickness of greater than 100, 90, 80, 75, 70, 60, 50, 45, 40, 35, 30, 25, or 20 nm. Each possibility represents a separate embodiment of the invention. In some embodiments, the membrane or first layer at the spot where the light focuses comprises a thickness of between 1-100, 1-75, 1-50, 1-45, 1-40, 1-35, 1-30, 1-25, 1-20, 1-15, 1-10, 1-5, 5-100, 5-75, 5-50, 5-45, 5-40, 5-35, 5-30, 5-25, 5-20, 5-15, 5-10, 10-100, 10-75, 10-50, 10-45, 10-40, 10-35, 10-30, 10-25, 10-20, 10-15, 15-100, 15-75, 15-50, 15-45, 15-40, 15-35, 15-30, 15-25, 15-20, 20-100, 20-75, 20-50, 20-45, 20-40, 20-35, 20-30, or 20-25 nm. Each possibility represents a separate embodiment of the invention. In some embodiments, the membrane or first layer at the spot where the light focuses comprises a thickness of between 10 and 50 nm. In some embodiments, the membrane or first layer at the spot where the light focuses does not comprise a thickness of less than 100, 90, 80, 75, 70, 60, 50, 45, 40, 35, 30, 25, 20, 15, 10, or 5 nm. Each possibility represents a separate embodiment of the invention. In some embodiments, the membrane or first layer at the spot where the light focuses does not comprise a thickness of more than 100, 90, 80, 75, 70, 60, 50, 45, 40, 35, 30, 25, or 20 nm. Each possibility represents a separate embodiment of the invention.

In some embodiments, the membrane comprises a high index of refraction. In some embodiments, the first layer comprises a high index of refraction. In some embodiments, the silicon nitride membrane comprises a high index of refraction. In some embodiments, a high index of refraction is an index at and/or above 1.8, 1.9, 2.0, 2.05, 2.1, 2.15, 2.2, 2.25, 2.3, 2.35 or 2.4. Each possibility represents a separate embodiment of the invention. In some embodiments, a high index of refraction is an index greater than 1.8, 1.9, 2.0, 2.05, 2.1, 2.15, 2.2, 2.25, 2.3, 2.35 or 2.4. Each possibility represents a separate embodiment of the invention. In some embodiments, a high index of refraction is an index greater than 2.2. In some embodiments, a high index of refraction is an index greater than 2.0. In some embodiments, the second layer does not comprise a high index of refraction. In some embodiments, the second layer comprises an index of refraction below a high index of refraction.

In some embodiments, the $SiN_x$ membrane comprises a silicon to nitride ratio of at least 0.7, 0.75, 0.8, 0.85, 0.9, 0.95, 1.0, 1.05, 1.1, 1.2 or 1.25. Each possibility represents a separate embodiment of the invention. In some embodiments, the $SiN_x$ membrane comprises a silicon to nitride ratio of at least 0.8. In some embodiments, the $SiN_x$ membrane comprises a silicon to nitride ratio of at least 0.75. In some embodiments, the $SiN_x$ membrane comprises a silicon to nitride ratio of greater than 0.7, 0.75, 0.8, 0.85, 0.9, 0.95, 1.0, 1.05, 1.1, 1.2 or 1.25. Each possibility represents a separate embodiment of the invention. In some embodiments, the $SiN_x$ membrane comprises a silicon to nitride ratio of greater than 0.8. In some embodiments, the $SiN_x$ membrane comprises a silicon to nitride ratio of greater than 0.75. It will be appreciated by a skilled artisan that increasing the refraction index and/or the ratio of silicon to nitride will increase the rate at which etching/thinning of the membrane proceeds. Further, a lower laser power, or a high wavelength of light could be used in combination with a membrane of higher index or ratio and not proceed more slowly as the two changes would offset.

In some embodiments, the membrane comprises a first layer and a second layer wherein the two layers have different refraction indexes, and/or different ratios of silicon to nitride. In some embodiments, the second layer that is refractory to etching/thinning by focused light. In some embodiments, the second layer is an inert layer. In some embodiments, the membrane comprises a dielectric layer. In some embodiments, the second layer is refractory/inert when not layered on a silicon nitride layer. In some embodiments, a metal oxide layer is refractory and/or inert. In some embodiments, a dielectric layer is refractory and/or inert. In some embodiments, the metal oxide layer is selected from a $TiO_2$, an aluminum oxide ($AlO_2$) and a hafnium oxide ($HfO_2$) layer. In some embodiments, the metal oxide is $TiO_2$. In some embodiments, the inert/refractory layer is layered onto a layer of silicon nitride. In some embodiments, the layer of silicon nitride sensitizes the refractory/inert layer to etching/thinning. In some embodiments, the silicon nitride layer catalyzes the etching/thinning of the refractory/inert layer when focused light is shown on the silicon nitride layer and/or the refractory/inert layer. In some embodiments, the membrane comprises a plurality of layers with different refraction indexes, and/or different ratios of silicon to nitride. A skilled artisan will appreciate that by modulating the intensity of light, the wavelength of the light, or the pH of the aqueous solution, thinning/etching can be done in only particular layers at a time.

In some embodiments, the membrane is a free-standing membrane. In some embodiments, the membrane is immersed in an aqueous solution. In some embodiments, the membrane is at least partially immersed in an aqueous solution. In some embodiments, the spot on the membrane is immersed in an aqueous solution. In some embodiments, immersed comprises an aqueous solution on both sides of the membrane. In some embodiments, the same aqueous solution is on both sides of the membrane. In some embodiments, different aqueous solutions are on each side of the membrane. In some embodiments, the system further comprises a first and second liquid reservoir. In some embodiments, the first and second liquid reservoirs are separated by the membrane.

In some embodiments, the system is configured to receive a free-standing membrane. In some embodiments, the system comprises an area configured to receive a free-standing membrane. In some embodiments, the area is a receiving area. In some embodiments, the area comprises at least one dimension configured for the placement of a free-standing membrane. In some embodiments, the area comprises a receptacle for an aqueous solution. In some embodiments, a receptacle is configured to receive an aqueous solution. In some embodiments, a receptacle is configured to hold an aqueous solution. In some embodiments, the receptacle is configured such that a received aqueous solution covers a spot on a received membrane. In some embodiments, the receptacle is configured such that a received aqueous solution covers a first spot on a received membrane. In some embodiments, the receptacle is configured such that a received aqueous solution covers a first spot and a second spot on a received membrane. In some embodiments, the area comprises two receptacles. In some embodiments, a first receptacle is configured such that a received aqueous solution covers a spot on one side of a received membrane and a second receptacle is configured such that a received aqueous solution covers the spot on the opposite side of a received membrane. In some embodiments, a first receptacle is configured such that a received aqueous solution covers a first spot on a received membrane and a second receptacle is configured such that a received aqueous solution covers a second spot on a received membrane. In some embodiments, a first receptacle and second receptacle receive different aqueous solutions.

In some embodiments, the aqueous solution is water. In some embodiments, the water is ultrapure water. In some embodiments, the aqueous solution is a salt buffer. In some embodiments, the aqueous solution comprises neutral pH. In some embodiments, the aqueous solution comprises alkaline pH. In some embodiments, the aqueous solution comprises neutral or alkaline pH. In some embodiments, alkaline pH is pH above 8. In some embodiments, alkaline pH is a pH between 8 and 10. In some embodiments, alkaline pH is a pH between 8 and 12. In some embodiments, alkaline pH is a pH between 10 and 12.

In some embodiments, the aqueous solution is at most at room temperature. In some embodiments, the membrane is at most at room temperature. In some embodiments, the spot on the membrane is at most at room temp. In some embodiments, the aqueous solution is at most at room pressure. In some embodiments, the membrane is at most at room pressure. In some embodiments, the spot on the membrane is at most at room pressure. In some embodiments, room temperature is 25 degrees Celsius. In some embodiments, room temperature is 20 degrees Celsius. In some embodiments, room temperature is between 20 and 25 degrees Celsius. In some embodiments, room pressure is 1 atmosphere. It will be understood by a skilled artisan that the method of drilling is advantageous as it does not require high temperature and/or high pressure in order to achieve drilling.

In some embodiments, the membrane is in an optically accessible flow cell. In some embodiments, the system further comprises an optically accessible flow cell. In some embodiments, optically accessible comprises optically accessible by a high numerical aperture objective. In some embodiments, the system further comprises a high numerical aperture objective. In some embodiments, the high numerical aperture objective is in a microscope. In some embodiments, the high numerical aperture objective is configured to focus light to a spot on the membrane. In some embodiments, the high numerical aperture objective is configured to focus light to a first spot on the membrane. In some embodiments, the system further comprises a microscope. In some embodiments, the microscope is a confocal microscope. In some embodiments, the microscope is for positioning the membrane so the light is focused on the spot. In some embodiments, the lens of the microscope focuses the light from the light source. In some embodiments, the system that directs and focuses light is a system of mirrors. In some embodiments, the system that directs and focuses light is a microscope. In some embodiments, the system that directs and focuses the light is a system of reflective metal surfaces. In some embodiments, the system is configured to direct and focus light from the light source.

In some embodiments, a spot on the membrane is a predetermined spot. In some embodiments, a spot on the membrane is a diffraction limited spot. In some embodiments, a spot is at least 1, 2, 3, 4, 5, 6, 7, 8, 9, 10, 15, 20, 30, 40, 50, 60, 70, 80, 90 or 100 spots. Each possibility represents a separate embodiment of the invention. In some embodiments, a spot is part of an array of spots. In some embodiments, the array of spots in a geometric configuration. Geometric configurations include squares, rectangles, circles, ovals, triangles, bowties, rods, cylinders, ellipses, disks, rhombuses and any other shape that may be found by one skilled in the art for nanopore arrays.

In some embodiments, the membrane comprises a second spot. In some embodiments, the second spot is on an opposite side of the membrane from the first spot. In some embodiments, the second spot is on the inverse side of the membrane from the first spot. In some embodiments, the second spot is positioned such that a line passing through the first spot also passed through the second spot. In some embodiments, the second spot is the spot on the membrane where light shined on the first spot exists the membrane. In some embodiments, the second spot is the spot on the membrane where light shined on the first spot would exit the membrane if the light generated a pore through the membrane. In some embodiments, the first spot and the second spot are a single spot that passes through the width of the membrane.

In some embodiments, the system further comprises a sensor. In some embodiments, the sensor is a photodetector. In some embodiments, the sensor is capable and/or configured to measure low light intensities. In some embodiments, the sensor is capable and/or configured to measure at high temporal resolution. In some embodiments, the sensor is configured to detect at the spot on the membrane. In some embodiments, the sensor is configured to detect emissions from the spot on the membrane. In some embodiments, the sensor is configured to detect at the membrane. In some embodiments, the sensor is configured to detect emissions from the membrane. In some embodiments, the sensor is configured to detect photoluminescent intensity (PL). In some embodiments, the sensor is configured to detect light. In some embodiments, the sensor is an electron detector. In some embodiments, the photodetector is a photodiode. In some embodiments, the photodiode is an avalanche photodiode. In some embodiments, the photodetector is a photomultiplier tube. In some embodiments, the photodetector is a CMOS camera.

In some embodiments, the sensor is an imaging sensor. In some embodiments, the system comprises a photodetector, an imaging sensor or both. In some embodiments, the imaging sensor is an electron microscope. In some embodiments, the imaging sensor is an electron multiplying charge-coupled device (CCD) camera. In some embodiments, the imaging sensor is a complementary metal oxide semiconductor (CMOS) camera. In some embodiments, the imaging sensor is a scientific CMOS (sCMOS) camera.

In some embodiments, the system further comprises a means to induce movement of a molecule from one side of the membrane to the other side of the membrane when there is a pore through the membrane. In some embodiments, the system further comprises a means to induce a current through the membrane. In some embodiments, the system further comprises a means to induce a current from one side of the membrane to the other side. In some embodiments, the system further comprises a means to induce movement of a molecule or create a charge from a first reservoir to a second reservoir. In some embodiments, the means to induce movement comprises a means of inducing an electrical current from one side of the membrane to the other side. In some embodiments, one side of the membrane to the other is from the first reservoir to the second reservoir. In some embodiments, the means to induce movement comprises a negative electrode on one side or within the first reservoir and a positive electrode on the second side or in the second reservoir. In some embodiments, the means is an apparatus configured to pass an electric current between two electrodes. In some embodiments, the system further comprises a current detector. In some embodiments, the current detector is configured to measure current between the two electrodes. In some embodiments, the current detector is configured to measure current between one side of the membrane and the other. In some embodiments, the current detector is configured to measure current between a first reservoir and a second reservoir.

In some embodiments, the current detector and/or the sensor are configured to shut off the light source upon a particular measurement. In some embodiments, the particular measurement is indicative of thinning to a desired thickness. In some embodiments, the particular measurement is indicative of the formation of a nanopore. In some embodiments, the particular measuring is indicative of a nanopore reaching a predetermined diameter. In some embodiments, the particular measurement is a predetermined threshold of PL intensity. In some embodiments, PL intensity is inversely proportional to the thickness of the spot on said membrane. In some embodiments, the sensor is configured to shut off the light source based on a measured PL intensity. In some embodiments, the particular measurement is an increase in ionic current. In some embodiments, an increase in ionic current through the membrane indicates the formation of a pore in the membrane. In some embodiments, a threshold ionic current indicates a particular diameter of pore has been formed. In some embodiments, the particular measurement is a visual measurement of the pore and/or its diameter.

In some embodiments, the system of the invention comprises the set up depicted in FIG. 1A. In some embodiments, the system of the invention comprises the set up depicted in FIG. 7A. In some embodiments, the system of the invention comprises the set up depicted in FIG. 16A. In some embodiments, the system of the invention comprises a portion of the set up depicted in FIGS. 1A, 7A and/or 16A.

In some embodiments, the system of the invention is for thinning a membrane. In some embodiments, the system of the invention is for controlled thinning of a membrane. In some embodiments, the system of the invention is for forming a pore through the membrane. In some embodiments, the forming a pore is in situ forming a pore at a predetermined spot. In some embodiments, the forming a pore is forming an array of pores. In some embodiments, the pore is a nanopore. In some embodiments, the pore is a pore of predetermined size. In some embodiments, a predetermined size is a predetermined diameter. In some embodiments, the predetermined size is diameter not greater than 1, 2, 3, 4, 5, 6, 7, 8, 9, 10, 15, 20, 25, 30, 35, 40, 45 or 50 nm. Each possibility represents a separate embodiment of the invention. In some embodiments, the predetermined size is diameter not less than 1, 2, 3, 4, 5, 6, 7, 8, 9, 10, 15, 20, 25, 30, 35, 40, 45 or 50 nm. Each possibility represents a separate embodiment of the invention. In some embodiments, the predetermined size is diameter of about 1, 2, 3, 4, 5, 6, 7, 8, 9, 10, 15, 20, 25, 30, 35, 40, 45 or 50 nm. Each possibility represents a separate embodiment of the invention.

In some embodiments, the system is for forming at least 1, 2, 3, 4, 5, 10, 15, 20, 25, 30, 35, 40, 45, 50, 60, 70, 80, 90, 100, 200, 300, 400, 500, or 1000 nanopores. Each possibility represents a separate embodiment of the invention. In some embodiments, the system is for producing a plurality of nanopores. In some embodiments, the array comprises dimensions of 5×5, 5×10, 5×15, 5×20, 5×25, 5×30, 5×35, 5×40, 5×45, 5×50, 10×10, 10×15, 10×20, 10×25, 10×30, 10×35, 10×40, 10×45, 10×50, 15×15, 15×20, 15×25, 15×30, 15×35, 15×40, 15×45, 15×50, 20×20, 20×25, 20×30, 20×35, 20×40, 20×45, 20×50, 25×25, 25×30, 25×35, 25×40, 25×45, 25×50, 30×30, 30×35, 30×40, 30×45, 30×50, 35×35, 35×40, 35×45, 35×50, 40×40, 40×45, 40×50, 45×45, 45×50, or 50×50 µm. Each possibility represents a separate embodiment of the invention. In some embodiments, the nanopores are separated by about 1 µm. In some embodiments, the nanopores in the array are separate by at least 1, 1.5, 2, 2.5, 3, 3.5, 4, 4.5, 5, 6, 7, 8, 9 or 10 µm. Each possibility represents a separate embodiment of the invention.

Methods of Use

By another aspect, there is provided a method of thinning a membrane, the method comprising shining focused light on a spot on a membrane, thereby thinning the membrane.

By another aspect, there is provided a method of thinning a membrane, the method comprising shining pulsed laser light on a spot on the membrane, thereby thinning the membrane.

By another aspect, there is provided a method of generating a nanopore, the method comprising shining a laser light on a spot on the membrane while monitoring ion current, stopping the laser light when the ion current begins increasing thereby generating a pore, shining a laser light on the pore for a first duration and at a first intensity, stopping the laser light and measuring at least of electrical resistance and current, shining a laser light on the pore for a second duration and at a second intensity, and repeating the stopping and shining until the measured electrical resistance and/or current indicates the pore is at a predetermined size, thereby generating a nanopore.

By another aspect, there is provided a method of generating a nanopore, the method comprising shining a continuous wave focused laser light on a spot on the membrane while monitoring ion current, stopping the continuous wave focused laser light when the ion current begins increasing thereby generating a pore, and shining pulsed laser light on the pore until the pore reaches a predetermined size, thereby generating a nanopore.

In some embodiments, the method is for light-induced thinning. In some embodiments, the method is for controlled thinning. In some embodiments, the method is for thinning in situ on a membrane. In some embodiments, the method is for thinning at a predetermined spot on a membrane. In some embodiments, the method is for rapid thinning. In some embodiments, the method is for light-induced drilling. In some embodiments, thinning comprises producing a pore through the membrane. In some embodiments, thinning is to a thickness of less than 10, 9, 8, 7, 6, 5, 4, 3, 2 or 1 nm. Each possibility represents s separate embodiment of the invention. In some embodiments, thinning is to a thickness of less than 5 nm. In some embodiments, thinning is to a thickness of less than 3 nm. In some embodiments, thinning is a thinning of at least 50, 60, 70, 75, 80, 85, 90, 95, 97, 99 or 100% of the membrane thickness. Each possibility represents s separate embodiment of the invention. In some embodiments, thinning is a thinning of at least 75% of the membrane thickness. It will be understood that thinning of 100% produces a hole through the membrane. In some embodiments, the thinning is performed by a first shining. In some embodiments, the shining is a first shining. In some embodiments, the pore is generated by a first shining.

In some embodiments, the thinning does not comprise a pretreatment. In some embodiments, the thinning does not comprise a pre-patterning step. In some embodiments, pretreatment is a pre-patterning. In some embodiments, pre-patterning is by a method other than a method of the invention. Any method of pre-patterning known in the art is envisioned. In some embodiments, the method is devoid of chemical etching. In some embodiments, the method is devoid of dielectric breakdown. In some embodiments, the method is devoid of electrochemical anodization. In some embodiments, the method is devoid of metal-assisted chemical etching. In some embodiments, the method is devoid of electron beam lithography (EBL) etching. In some embodiments, the method is devoid of reactive ion etching (RIE). In some embodiments, the method is devoid of metal deposition fabrication. In some embodiments, the method is devoid of ion-track etching. In some embodiments, the method is devoid of focused electron beam (e-Beam) lithography. In some embodiments, the method is devoid of focused ion beam (FIB) lithography.

In some embodiments, the focused light is laser light. In some embodiments, the light is focused light. In some embodiments, the light is monochromatic light. In some embodiments, the focused light is within the purple spectrum. In some embodiments, the focused light is purple light. In some embodiments, the focused light is within the blue spectrum. In some embodiments, the focused light is blue light. In some embodiments, the focused light is within the green spectrum. In some embodiments, the focused light is green light. In some embodiments, the focused light is light focused from a light source. In some embodiments, the light is focused by a system for focusing the light and directing it to a spot on the membrane. In some embodiments, the light comprises a wavelength of between 300-600 nm. In some embodiments, the laser light is continuous-wave laser light. In some embodiments, the laser light is continuous-wave focused laser light. In some embodiments, the laser light is pulsed laser light. In some embodiments, shining pulsed laser light is pulsing laser light on a spot on the membrane.

In some embodiments, the light has an intensity of at least 1, 10, 50, 100, 200, 300, 400, 500, 600, 700, 800, 900 or 1000 µW. Each possibility represents a separate embodiment of the invention. In some embodiments, the light has an intensity of at least 1 µW. In some embodiments, the light has an intensity of at least 10 µW. In some embodiments, the light has an intensity of at least 100 µW. In some embodiments, the light has an intensity of at least 1000 µW. In some embodiments, the power of the light is between 1 µW and 50 mW, 1 µW and 45 mW, 1 µW and 40 mW, 1 µW and 35 mW, 1 µW and 30 mW, 1 µW and 25 mW, 1 µW and 20 mW, 1 µW and 15 mW, 1 µW and 1 mW, 1 µW and 5 mW, 1 µW and 1 mW, 10 µW and 50 mW, 10 µW and 45 mW, 10 µW and 40 mW, 10 µW and 35 mW, 10 µW and 30 mW, 10 µW and 25 mW, 10 µW and 20 mW, 10 µW and 15 mW, 10 µW and 10 mW, 10 µW and 5 mW, 10 µW and 1 mW, 100 µW and 50 mW, 100 µW and 45 mW, 100 µW and 40 mW, 100 µW and 35 mW, 100 µW and 30 mW, 100 µW and 25 mW, 100 µW and 20 mW, 100 µW and 15 mW, 100 µW and 10 mW, 100 µW and 5 mW, 100 µW and 1 mW, 200 µW and 50 mW, 200 µW and 45 mW, 200 µW and 40 mW, 200 µW and 35 mW, 200 µW and 30 mW, 200 µW and 25 mW, 200 µW and 20 mW, 200 µW and 15 mW, 200 µW and 10 mW, 200 µW and 5 mW, 200 µW and 1 mW, 300 µW and 50 mW, 300 µW and 45 mW, 300 µW and 40 mW, 300 µW and 35 mW, 300 µW and 30 mW, 300 µW and 25 mW, 300 µW and 20 mW, 300 µW and 15 mW, 300 µW and 10 mW, 300 µW and 5 mW, 300 µW and 1 mW, 400 µW and 50 mW, 400 µW and 45 mW, 400 µW and 40 mW, 400 µW and 35 mW, 400 µW and 30 mW, 400 µW and 25 mW, 400 µW and 20 mW, 400 µW and 15 mW, 400 µW and 10 mW, 400 µW and 5 mW, 400 µW and 1 mW, 500 µW and 50 mW, 500 µW and 45 mW, 500 µW and 40 mW, 500 µW and 35 mW, 500 µW and 30 mW, 500 µW and 25 mW, 500 µW and 20 mW, 500 µW and 15 mW, 500 µW and 10 mW, 500 µW and 5 mW, 500 µW and 1 mW, 1 mW and 50 mW, 1 mW and 45 mW, 1 mW and 40 mW, 1 mW and 35 mW, 1 mW and 30 mW, 1 mW and 25 mW, 1 mW and 20 mW, 1 mW and 15 mW, 1 mW and 10 mW, and 1 mW and 5 mW. Each possibility represents a separate embodiment of the invention. In some embodiments, the power of the light is between 100 µW and 45 mW. In some embodiments, the power of the light is between 1 mW and 45 mW.

In some embodiments, the method further comprises measuring PL intensity from the membrane. In some embodiments, the measuring PL intensity is from the spot on the membrane. In some embodiments, the method further comprises stopping thinning bases on the measured PL intensity. In some embodiments, the stopping occurs when the PL intensity reaches a predetermined threshold. In some embodiments, the predetermined threshold is when a pore is formed in the membrane. In some embodiments, the predetermined threshold is when a pore has reached a predetermined diameter. In some embodiments, the PL intensity is inversely proportional to the thickness of the spot on the membrane. In some embodiments, the thinning is stopped at a predetermined thickness. In some embodiments, PL intensity comprises ion current. In some embodiments, measuring is performed while the light is not shining. In some embodiments, measuring is performed at a time point after the light is turned off sufficient to allow PL through the pore to stabilize.

In some embodiments, the thinning comprises forming a pore through the membrane at the spot. In some embodiments, the pore is a nanopore. In some embodiments, the nanopore comprises a diameter not greater than 1, 2, 3, 4, 5, 10, 15, 20, 25, 30, 35, 40, 45 or 50 nm. Each possibility represents a separate embodiment of the invention. In some embodiments, the nanopore comprises a diameter not greater than 5 nm. In some embodiments, the nanopore comprises a diameter of about 5 nm. In some embodiments, the nanopore comprises a diameter between 0.5 and 10, 0.5 and 15, 0.5 and 20, 1 and 10, 1 and 15, 1 and 20, 3 and 10, 3 and 15, 3 and 20, 5 and 10, 5 and 15, or 5 and 20 nm. Each possibility represents a separate embodiment of the invention. In some embodiments, the diameter of the nanopore can be selected by monitoring the PL intensity and or optically monitoring the nanopore formation. In some embodiments, the diameter of the nanopore can be selected by altering the light intensity, wavelength, or duration, or the pH of the solution. A skilled artisan can optimize the variable parameters to generate a nanopore of the desired diameter in the desired time.

In some embodiments, the nanopore comprises a Gaussian shape. In some embodiments, the nanopore comprises a varying diameter. In some embodiments, the nanopore comprises a Gaussian curve shaped cross-section. In some embodiments, the thinning produces a nanowell adjacent to the nanopore. In some embodiments, the thinning produces a nanowell without a nanopore. In some embodiments, the thinning produces a nanowell in one layer and an adjacent nanopore in a second layer. As used herein, the term "nanowell" refers to a passage through the membrane. A nanowell may also be referred to as a nanoslot. In some embodiments, the nanowell comprises a Gaussian shape. In some embodiments, the nanowell comprises a varying diameter. In some embodiments, the nanowell comprises a Gaussian curve shaped cross-section. In some embodiments, the nanopore and/or nanowell produce a low optical background. In some embodiments, the membrane produces a low optical background. In some embodiments, the low optical background is lower than the optical background of a nanopore and/or nanowell that does not have a Gaussian curve shape or a Gaussian curve shaped cross-section. In some embodiments, the low optical background is at least 10, 20, 30, 40, 50, 60, 70, 80, 90, 95, 97 or 99% lower. Each possibility comprises a separate embodiment of the invention.

In some embodiments, a membrane comprising a first and second layer comprises an interface of the first and second layer. In some embodiments, the interface is the place wherein the second layer is layered on the first layer. In some embodiments, the membrane comprises a first layer and a second layer and the nanopore comprises a first Gaussian curve shaped cross-section increasing in diameter from the interface of the first layer with the second layer to an exposed surface of the first layer. In some embodiments, the membrane comprises a first layer and a second layer and the nanopore comprises a second Gaussian curve shaped cross-section increasing in diameter from the interface of the first layer with the second layer to an exposed surface of the second layer. In some embodiments, the nanopore comprises two regions each with a Gaussian curve shaped cross-section. In some embodiments, the first Gaussian curve shaped cross-section is in the first layer. In some embodiments, the second Gaussian curve shaped cross-section is in the second layer.

In some embodiments, the method further comprises measuring ionic current through the membrane. In some embodiments, the spot of the membrane is immersed in an aqueous solution and the ionic current is measured from the solution on one side of the membrane to the solution on the other side of the membrane. In some embodiments, an increase in ionic current through the membrane or from one side to the other, or from one reservoir to the other, indicates the formation of a pore in the membrane. In some embodiments, formation of the pore in the membrane is formation of the pore at the spot in the membrane. In some embodiments, the spot is a predetermined spot. In some embodiments, the increase in ionic current is a sudden increase in ionic current. In some embodiments, the increase in ionic current is not gradual. In some embodiments, the increase is at least a 10, 20, 30, 40, 50, 60, 70, 80, 90, 100, 150, 200, 250, 300, 350, 400, 450 or 500% increase in ionic current. Each possibility represents a separate embodiment of the invention. In some embodiments, after a pore has been formed a gradual increase in ionic current corresponds to the widening of the diameter of the nanopore. In some embodiments, the thinning is stopped at a predetermined current and/or diameter.

In some embodiments, the method further comprises measuring ion current. In some embodiments, measuring is monitoring. In some embodiments, ion current is ion current through the nanopore. In some embodiments, ion current is from a first side of the membrane to a second side of the membrane. In some embodiments, the first side is the cis side. In some embodiments, the second side is the trans side. In some embodiments, the cis side is the side which the light comes from. In some embodiments, the cis side is the side on which thinning/drill is occurring. In some embodiments, the cis side is the side with the first layer. In some embodiments, measuring is performed while the light is not shining. In some embodiments, measuring is performed at a time point after the light is turned off sufficient to allow ion current through the pore to stabilize.

In some embodiments, the method is for rapid formation of a nanopore. In some embodiments, a pore can be produced at a spot in the membrane with a thickness of at least 10, 20, 30, 40, 50, 60, 70, 80, 90 or 100 nm. Each possibility represents a separate embodiment of the invention. In some embodiments, a pore can be produced at a spot in the membrane with a thickness of at most 10, 20, 30, 40, 50, 60, 70, 80, 90 or 100 nm. Each possibility represents a separate embodiment of the invention. In some embodiments, a pore can be produced at a spot in the membrane with a thickness of at most 50 nm. In some embodiments, a pore can be produced at a spot in the membrane with a thickness of at most 100 nm. In some embodiments, a pore can be produced in less than 1, 5, 10, 15, 20, 25, 30, 35, 40, 45, 50, 55 or 60 seconds. Each possibility represents a separate embodiment of the invention. In some embodiments, a pore can be produced through a spot in the membrane with a thickness of at least 40 nm in less than 20 seconds.

In some embodiments, the method further comprises stopping the light when the ion current begins increasing. In some embodiments, the stopping is stopping the first shining. It will be understood by a skilled artisan that until a pore is formed the ion current will stay constant, however, upon pore formation ions will begin moving from one side of the membrane to the other resulting in an increase in ion current. Thus, the formation of a nanopore can be identified by the onset of ion current increase. In some embodiments, the stopping is stopping upon formation of a pore through the membrane. In some embodiments, the shining and stopping generates a pore through the membrane. In some embodiments, the ion current increase is an increase of at least a predetermine threshold. In some embodiments, the increase is to above a predetermined threshold. In some embodiments, the increase is by at least a predetermined threshold. In some embodiments, the threshold is about 4 nA/s. In some embodiments, the threshold is about 1, 2, 3, 3.5, 4, 4.5, 5, 6, 7, 8, 9 or 10 nA/s. Each possibility represents a separate embodiment of the invention. In some embodiments, the threshold is between 1-6, 1-5, 1-4.5, 1-4, 2-6, 2-5, 2-4.5, 2-4, 3-6, 3-5, 3-4.5, 3-4, 3.5-6, 3.5-5, 3.5-4.5, 3.5-4, 4-6, 4-5 or 4-4.5 nA/s. Each possibility represents a separate embodiment of the invention. In some embodiments, the threshold is between 3-5 nA/s. In some embodiments, the threshold is between 3.5-4.5 nA/s.

In some embodiments, the method further comprises shining a light on the pore. In some embodiments, the pore is the generated pore. In some embodiments, the shining is a second shining. In some embodiments, the shining is for a first duration. In some embodiments, the second shining is for a first duration. In some embodiments, the shining is at a first intensity. In some embodiments, the second shining is at a first intensity.

In some embodiments, the duration is about 5, 10, 15, 20, 25, 30, 35, 40, 45, 50, 55, 60, 65, 70, 75, 80, 85, 90, 95, 100, 105, 110, 115, 120, 125, 130, 140, 150, 160, 170, 175, 180, 190, 200, 210, 220, 225, 230, 2450, 250, 260, 270, 275, 280, 290, 300, 325, 350, 375, 400, 425, 450, 475, or 500 seconds. Each possibility represents a separate embodiment of the invention. In some embodiments, the duration is about 100 seconds. In some embodiments, the duration is the first duration. In some embodiments, the duration is the second duration.

In some embodiments, the method further comprises stopping the light. In some embodiments, the method further comprises stopping the shining. In some embodiments, the shining is the second shining. In some embodiments, the shining is the first shining. In some embodiments, the shining is the third shining.

In some embodiments, the method further comprises measuring electrical resistance. In some embodiments, the method further comprises measuring current. In some embodiments, current is electrical current. In some embodiments, the method further comprises measuring at least one of electrical resistance and current. In some embodiments, current is current at the pore. In some embodiments, current is current through the pore. In some embodiments, resistance is resistance through the pore. In some embodiments, resistance is resistance at the pore. In some embodiments, measuring is performed while the light is not shining. In some embodiments, measuring is performed at a time point after the light is turned off sufficient to allow resistance through the pore to stabilize.

In some embodiments, the method further comprises shining laser light at the pore. In some embodiments, the shining is a third shining. In some embodiments, the pore is the generated pore. In some embodiments, the pore is the pore after the second shining. In some embodiments, the shining is for a second duration. In some embodiments, the third shining is for a second duration. In some embodiments, the shining is at a second intensity. In some embodiments, the third shining is at a second intensity.

In some embodiments, the second duration is based on the measured electrical current. In some embodiments, the second duration is based on the measured electrical resistance. In some embodiments, the second intensity is based on the measured electrical current. In some embodiments, the second intensity is based on the measured electrical resistance. In some embodiments, at least one of the second duration and second intensity are based on at least one of the electrical resistance and electrical current. In some embodiments, both the second duration and second intensity are based on the electrical resistance, current or both.

In some embodiments, the second duration is different than the first duration. In some embodiments, the second intensity is different than the first intensity. In some embodiments, the second duration is longer than the first duration. In some embodiments, the second duration is shorter than the first duration. In some embodiments, the second intensity is greater than the first intensity. In some embodiments, the second intensity is less than the first intensity. In some embodiments, the second duration is increased as compared to the first duration if the measured current indicates an effectiveness ratio above a predetermined threshold. In some embodiments, the second duration is increased as compared to the first duration if the measured resistance indicates an effectiveness ratio above a predetermined threshold. In some embodiments, the second intensity is increased as compared to the first intensity if the measured current indicates an effectiveness ratio above a predetermined threshold. In some embodiments, the second intensity is increased as compared to the first intensity if the measured resistance indicates an effectiveness ratio above a predetermined threshold. In some embodiments, the second duration is decreased as compared to the first duration if the measured current indicates an effectiveness ratio at or below a predetermined threshold. In some embodiments, the second duration is decreased as compared to the first duration if the measured resistance indicates an effectiveness ratio at or below a predetermined threshold. In some embodiments, the second intensity is decreased as compared to the first intensity if the measured current indicates an effectiveness ratio at or below a predetermined threshold. In some embodiments, the second intensity is decreased as compared to the first intensity if the measured resistance indicates an effectiveness ratio at or below a predetermined threshold. In some embodiments, decreased comprises returning the intensity and/or duration to a starting level. In some embodiments, decreased is decreased to the starting level.

In some embodiments, the effectiveness ratio is determined by $$\frac{\mu^{N-1}}{I_N}.$$

In some embodiments, $\mu^{N-1}$ is the mean current. In some embodiments, $\mu^{N-1}$ is the mean current of previous measurements. In some embodiments, pervious measurements is all previous measurements. In some embodiments, previous measurements is the last 2, 3, 4, 5, 6, 7, 8, 9, 10, 11, 12, 13, 14, 15, 16, 17, 18, 19 or 20 previous measurements. Each possibility represents a separate embodiment of the invention. In some embodiments, previous measurements is all previous measurements since a last measurement that produced an effectiveness ratio at or below the predetermined threshold. In some embodiments, previous measurements is all previous measurements since a last measurement that produced an effectiveness ratio above the predetermined threshold. In some embodiments, the predetermined threshold is about 0.8. In some embodiments, the predetermined threshold is about 0.6, 0.65, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, or 1. Each possibility represents a separate embodiment of the invention. In some embodiments, $I_N$ is the measured electrical current. In some embodiments, the current is derived from the resistance.

In some embodiments, increased is geometrically increased. In some embodiments, the duration is geometrically increased. In some embodiments, the intensity is geometrically increased. In some embodiments, the intensity is linearly increased. In some embodiments, the duration is increased geometrically based on the number of consecutive measurements that produced an effectiveness ratio above the predetermined threshold. In some embodiments, the duration is increased geometrically based on the number of consecutive measurements that produced an effectiveness ratio at or below the predetermined threshold. In some embodiments, the second duration is increased. In some embodiments, any subsequent duration is increased. In some embodiments, the linear increase is based on the number of consecutive measurements that produced an effectiveness ratio above the predetermined threshold. In some embodiments, the linear increase is based on the number of consecutive measurements that produced an effectiveness ratio at or below the predetermined threshold.

In some embodiments, the second intensity is the same as the first intensity. In some embodiments, the second duration is the same as the first duration. In some embodiments, the second intensity is the same as the first intensity if the measured resistance indicates an effectiveness ratio at or below a predetermined threshold. In some embodiments, the second duration is the same as the first duration if the measured resistance indicates an effectiveness ratio at or below a predetermined threshold. In some embodiments, the duration and/or intensity are the same if the effectiveness ratio is at or below a predetermined threshold and a significance parameter is at or below a predetermined threshold. In some embodiments, the duration and/or intensity are the same if the effectiveness ratio is above a predetermined threshold and a significance parameter is at or below a predetermined threshold. In some embodiments, the duration and/or intensity are increased if the effectiveness ratio is at or below a predetermined threshold and a significance parameter is above a predetermined threshold. In some embodiments, the duration and/or intensity are increased if the effectiveness ratio is above a predetermined threshold and a significance parameter is at or below a predetermined threshold. In some embodiments, the significance parameter s $I_N - \mu^{N-1}$. In some embodiments, the significance parameter predetermined threshold is about 1 nA. In some embodiments, the significance parameter predetermined threshold is about 0.1, 0.2, 0.3, 0.4, 0.5, 0.6, 0.7, 0.75, 0.8, 0.9, 1.0, 1.1, 1.2, 1.3, 1.4, 1.5, 1.6, 1.7, 1.75, 1.8, 1.9, 2.0, 2.5, 3.0, 3.5, 4.0, 4.5, 5, 6, 7, 7.5, 8, 9 or 10 nA. Each possibility represents a separate embodiment of the invention.

In some embodiments, the method further comprises repeating the stopping and shining until the pore is at a predetermined size. In some embodiments, the repeated shining is repeating the third shining. In some embodiments, the predetermined size is determined by the measured electrical resistance and/or current. In some embodiments, the repeating is performed until the measured electrical resistance and/or current indicates the pore is at a predetermined size. In some embodiments, electrical resistance indicates the size. In some embodiments, electrical current indicates the size.

In some embodiments, the repeating comprises shining pulsed laser light on the pore. In some embodiments, each shining and stopping is a pulse. In some embodiments, the measuring is performed between pulses. In some embodiments, the measuring is performed between each pulse. In some embodiments, the measuring is performed during shining pulsed light. In some embodiments, the pulsed laser light comprises pulses of different duration. In some embodiments, the pulsed laser light comprises pulses of different intensity. In some embodiments, shining pulsed laser light comprises: shining the light at the pore for a first duration and at a first intensity, stopping the shining and measuring, shining light at the pore for a second duration and at a second intensity and repeating the stopping and shining.

In some embodiments, following a measured current below a predetermined threshold a first amount of time is allowed to pass before the measuring after the laser is stopped. In some embodiments, following a measured resistance above a predetermined threshold a first about of time is allowed to pass before the measuring after the laser is stopped. In some embodiments, the current is determined from the resistance. In some embodiments, following a measured current above a predetermined threshold a second amount of time is allowed to pass before the measuring after the laser is stopped. In some embodiments, following a measured resistance below a predetermined threshold a second amount of time is allowed to pass before the measuring after the laser is stopped. In some embodiments, the second amount of time is larger than the first amount of time. In some embodiments, the second amount of time is shorter than the first amount of time. In some embodiments, larger is twice the amount. In some embodiments, larger is 1.5, 1.75, 2, 2.25, 2.5, 2.75, 3, 3.5, 4, or 5 times the amount. Each possibility represents a separate embodiment of the invention.

In some embodiments, the current threshold is a predetermined percentage of the current. In some embodiments, the current threshold is a predetermined percentage of the current through the nanopore. In some embodiments, the current through the nanopore is at a predetermined size. In some embodiments, the current through the nanopore is through ha nanopore at the predetermined size. In some embodiments, the predetermined threshold percentage is about 20, 25, 30, 35, 40, 45, 50, 55, 60, 65, 70, 75, 80, 85, 90, 95 or 97%. Each possibility represents a separate embodiment of the invention. In some embodiments, the predetermined threshold percentage is about 50%.

In some embodiments, the method further comprises a focusing step. In some embodiments, the focusing step is before the first step. In some embodiments, the first step is shining the light on the spot. In some embodiments, focusing comprises using imaging of the membrane to focus the laser light at the spot. In some embodiments, the imagine is light imaging. In some embodiments, the imaging is white light imagine. In some embodiments, the light is visible light. In some embodiments, focusing comprises shining laser light on the membrane. In some embodiments, the laser light is at a reduced intensity. In some embodiments, reduced is as compared to the intensity used for thinning. In some embodiments, reduced is as compared to the intensity used for drilling. In some embodiments, reduced is as compared to the intensity used in the first step. In some embodiments, the reduced intensity laser light produces a photoluminescent spot. In some embodiments, focusing comprises selecting a focus. In some embodiments, the selecting a focus comprises selecting the focus at which the photoluminescent spot is at its minimum size. In some embodiments, the selecting a focus comprises selecting the focus at which the photoluminescent spot is at its maximum intensity. In some embodiments, the selecting a focus comprises selecting the focus at which the photoluminescent spot is at its maximum intensity and minimum size. In some embodiments, minimum size is minimum diameter.

Nanopores/Nanowells

By another aspect, there is provided a membrane comprising a nanopore and/or nanowell, wherein the nanopore and/or nanowell is produced by a method of the invention.

By another aspect, there is provided a membrane comprising a nanopore and/or nanowell, wherein the nanopore and/or nanowell comprises a varying diameter and a Gaussian curve shaped cross-section.

In some embodiments, a nanopore and/or nanowell produced by the method of the invention comprises a varying diameter. In some embodiments, the varying diameter is a Gaussian shape. In some embodiments, the varying diameter corresponds to a Gaussian shaped cross-section of the nanowell and/or nanopore. In some embodiments, the nanopore and/or nanowell produced by a method of the invention comprises a Gaussian curve shaped cross-section. In some embodiments, the nanopore and/or nanowell increases in diameter from one side of the membrane to the other. In some embodiments, the nanopore and/or nanowell has a larger diameter on the side of the membrane upon which the light was shown. In some embodiments, the increasing diameter from one side to the other follows a Gaussian curve. In some embodiments, the Gaussian curve comprises a full width at half maximum of one half of the wavelength of the focused light used to generate the nanopore and/or nanowell.

In some embodiments, the nanopore, nanowell and/or membrane produces a low optical background. In some embodiments, the low optical background is lower than the background of a membrane comprising a nanopore and/or nanowell that does not comprise a Gaussian shape or cross-section. In some embodiments, the low optical background is lower than the background of a membrane not produced by the method of the invention.

In some embodiments, a membrane comprising a first and second layer comprises an interface of the first and second layer. In some embodiments, the interface is the place wherein the second layer is layered on the first layer. In some embodiments, the membrane comprises a first layer and a second layer and the nanopore comprises a first Gaussian curve shaped cross-section increasing in diameter from the interface of the first layer with the second layer to an exposed surface of the first layer. In some embodiments, the membrane comprises a first layer and a second layer and the nanopore comprises a second Gaussian curve shaped cross-section increasing in diameter from the interface of the first layer with the second layer to an exposed surface of the second layer. In some embodiments, the nanopore comprises two regions each with a Gaussian curve shaped cross-section. In some embodiments, the first Gaussian curve shaped cross-section is in the first layer. In some embodiments, the second Gaussian curve shaped cross-section is in the second layer.

In some embodiments, the membrane is a membrane as described hereinabove. In some embodiments, the nanopore is a nano-scale aperture. In some embodiments, the nanopore is as described hereinabove. In some embodiments, the nanowell is a nanowell as described hereinabove. In some embodiments, the membrane comprises a plurality of layers. In some embodiments, at least two layers comprise nanopores and/or nanowells of different sizes. In some embodiments, one layer comprises a nanowell and a second layer comprises a nanopore.

As used herein, the term "about" when combined with a value refers to plus and minus 10% of the reference value. For example, a length of about 1000 nanometers (nm) refers to a length of 1000 nm+−100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Chip fabrication. Nanopore chips were fabricated from a 4" (100 mm) double-side polished, 350 µm thick silicon wafers coated with 500 nm of thermal SiO$_2$ (Silicon Valley Microelectronics, CA USA). 50 nm thick low-stress silicon nitride (SiN$_x$) layers were deposited on both sides using low pressure chemical vapor deposition (LPCVD) with different NH$_3$/SiH$_2$Cl$_2$ gas ratios, resulting in different refractive indices ranging from 2.15 to 2.43. The refractive index was then measured by ellipsometry (Film Sense, FS-1). Next, direct-write photolithography (MicroWriter ML3, DMO) was used to pattern the windows and dice lines on the resist. A hard mask was created using reactive ion etch (RIE, Diener Electronic) followed by buffered oxide etch (BOE) to remove the SiO$_2$ and expose the Si layer. The wafer was then immersed in KOH at 65° C. for up to 20 hours followed by a second round of BOE to open up a freestanding SiN$_x$ membrane. Each chip was cleaned by piranha before usage (3:1 H$_2$SO$_4$:H$_2$O$_2$), vacuum dried, and mounted onto a Teflon holder with Ecoflex 5 (Smooth-ON, Reynolds Advanced Materials) silicone rubber. The chip was then placed in a Teflon cell equipped with a quartz cover-slide bottom. The position of the cell was controlled using a 3D nanopositioner stage (Physik Instrumente, P-561.3CD). Alternatively, nanopore chips were fabricated from a 4" silicon wafer coated with 500 nm SiO$_2$ and 50 nm low-stress amorphous SiN$_x$. To create freestanding membranes, a hard mask was RIE-etched into the SiN$_x$ followed by HF etching to remove the SiO$_2$, and then through-etching of Si with KOH. The free-standing membranes were 40-45 nm thick.

Chip assembly. Chips were first cleaned by piranha (3:1 H$_2$SO$_4$:H$_2$O$_2$). They were then glued onto a custom-made Teflon insert, immersed in buffer (1 M KCl, 40 mM Tris-HCl, 1 mM EDTA, pH 7.5), and placed in a Teflon cell with a quartz cover-slide bottom. The cell was mounted onto a 3D nanopositioner located above the microscope objective. The setup was shielded by a grounded copper box and placed on a vibration-isolating optical table.

Optical setup. A previously described custom-built confocal microscope was modified for this study: Two collimated laser lines are focused onto a diffraction-limited laser spot at the membrane surface. The emitted light is collected by the same objective (NA=1.15), focused onto a spatial pinhole to reject out-of-focus light, passed through an ND-filter and directed onto two spectrally separated APDs for two-color imaging.

In FIG. 1A-D, the full photoluminescence is roughly 3 orders in magnitude larger. In order not to damage the APDs, an ND3 filter is positioned in the emission pathway during etching and before the excitation pathway during profiling. The photoluminescence count is a summation of the red (>650 nm) and green (550-650 nm) channels.

Ionic current was measured by cis/trans-immersed Ag/AgCl electrodes connected to a high-bandwidth amplifier (Axon 200B) sampled at 125 kHz (DAQ NI-6211) and filtered at 10 kHz. Photon counting was sampled at 500 kHz (DAQ NI-6602). The two cards were triggered simultaneously via a hardware connection and were fully controlled by custom LabVIEW software.

Figure 7A:
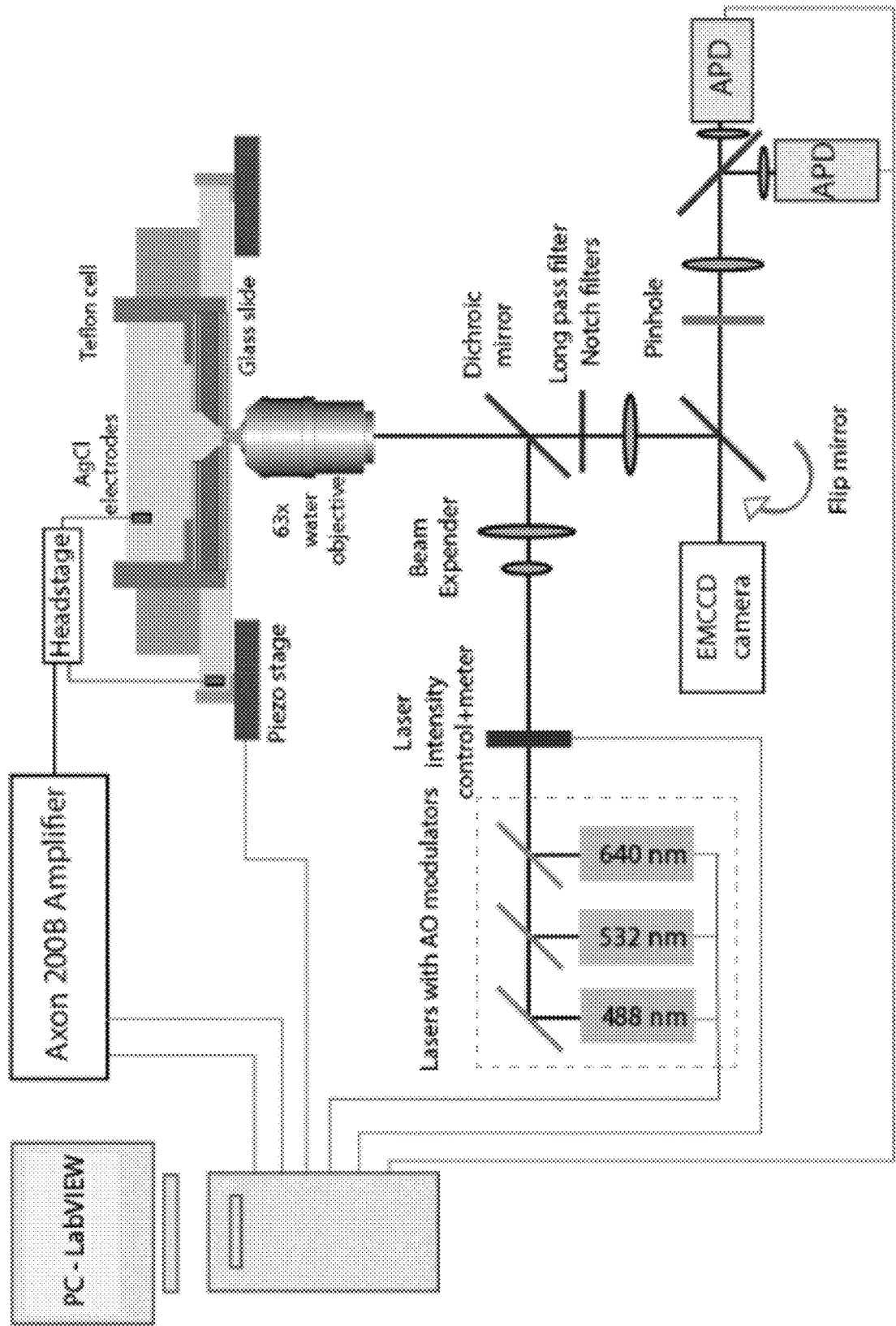

Alternatively, A custom-made three-color confocal set up was used for the electro-optical measurements as depicted in FIG. 7A. The lasers were focused to a diffraction-limited spot at the membrane surface using a high NA objective (Zeiss Apochromat 63x/1.15). The emitted light was collected using the same objective, filtered using the appropriate long pass and notch filters (Semrock) and focused on either an EMCCD camera (ANDOR, iXon 887) or a 100 µm pinhole (Thorlabs). Light passing through the pinhole was collimated and split using a dichroic mirror (Semrock) with center wavelengths of λ=650 nm and focused onto two APDs (Perkin Elmer SPCM-AQR-14). The emitted light was attenuated using an ND3 filter during thinning and drilling to protect the APDs. Photon counting from the APDs was sampled at 500 kHz (DAQ NI-6602). The photoluminescence presented throughout the paper is a summation of the red (>650 nm) and green (550-650 nm) channels. Ionic current was measured by cis/trans-immersed Ag/AgCl electrodes connected to a high-bandwidth amplifier (Axon 200B) sampled at 125 kHz (DAQ NI-6514) and filtered at 10 kHz. The two cards were triggered simultaneously via a hardware connection and were fully controlled by custom LabVIEW software.

TEM imaging. High-resolution images were acquired with a FEI Titan Themis Cs-Correct HR-S/TEM. The relative thickness map (RTM) was automatically generated using the Gatan Digital Micrograph® EFTEM technique by first acquiring an unfiltered and a zero-loss image from the same region under identical conditions. The RTM was then computed using the Poisson statistics of inelastic scattering: $t/\lambda = -\ln(I_O/I_t)$, where $I_O$ is the zero-loss intensity and $I_t$ is the total intensity. To obtain the true thickness, $t/\lambda$ is multiplied by the mean free path (110 nm) in silicon nitride (Si:N 3:4). The low loss energy spectrum was measured in scanning transmission electron microscopy (STEM) in increments of 20 nm and was used to automatically generate relative thickness maps using Digital Micrograph software (Gatan).

Composition analysis: Chemical mapping of the SiN$_x$ membranes was performed using energy dispersive X-ray imaging (EDS, Dual Bruker XFlash6) and scanning transmission electron microscopy (STEM) based on core-loss electron energy loss spectroscopy (EELS). The EDS quantification was done using Velox (Thermo Fisher) and EELS quantification was done using the Digital Micrograph software (Gatan).

Ellipsometry measurements. Performed with model FS-1 multi-Wavelength Ellipsometer (Film Sense).

Calcium indicator experiments. The setup and protocol exactly follow standard procedures with a Fluo-4 and CaCl$_2$) concentration of 500 nM and 500 mM, respectively.

DNA Translocation experiments. Nanopores were allowed to equilibrate at a low probing voltage (0.1 to 0.3 V) in buffer (1 M KCl, 40 mM Tris-HCl, 1 mM EDTA, pH 7.5) for at least 10 minutes to obtain a stable open pore current prior to adding homemade 5054 bp dsDNA. Events were monitored using an Axon 200B filtered at 100 kHz and custom LabVIEW software.

Alternatively, for the translocation experiment, the chip was immersed in a pH 7 buffer (in buffer (1 M KCl, 40 mM Tris-HCl, 1 mM EDTA) and 300 mV was applied until the open pore current stabilized. 300 bp dsDNA was added to the cis chamber at a concentration of 1 nM. Translocation events were monitored and recorded using an Axon 200B filtered at 100 kHz and custom LabVIEW software. An offline analysis program was used to analyze each event separately to extract the amplitude block and dwell time for each translocation.

Protein Translocation Experiments. In some cases, nanopores were kept dry in air for up to 10 days prior to performing the experiment. These nanopores were cleaned by Dynasolve 185 to remove PDMS and then made hydrophilic by piranha (3:1 H$_2$SO$_4$:H$_2$O$_2$). Nanopores were allowed to equilibrate at a low probing voltage (0.1 to 0.3 V) in buffer (1 M KCl, 40 mM Tris-HCl, 1 mM EDTA, pH 7.0) for at least 10 minutes to obtain a stable open pore current prior to adding 0.007 µg/µl di-ubiquitin. Commercially available, as well as home-purified proteins such as Ubiquitin, eIF4A, Albumin, etc. where suspended in the buffer and translocation events were monitored using an Axon 200B filtered at 100 kHz and custom LabVIEW software.

Automated nanopore drilling: Custom software (LabVIEW) was used to automatically drill either a single or multiple pores according to the input coordinates (x,y) list and a current gradient threshold. 150 mV potential was applying across the membrane and the current was monitored in real time. The piezoelectric stage was moved to each coordinate, where the laser was switched on until the current threshold was reached. The laser was then switched off, stopping the drilling. As a preliminary stage to this process, the laser was focused at the (x=0,y=0) coordinate at low intensity. The nanopores array was validated using $Ca^{+2}$ based imaging.

pH experiments: Four 1 M KCl buffers with different pH levels were prepared: 20 mM Sodium acetate (SodAc) for pH 4, 20 mM Tris for pH 7, 20 mM Sodium bicarbonate (SodBic) for pH 10, and KOH based buffer for pH 12. The buffers' refractive index was measured using a refractometer (Rudolph, J257) and was found to be similar for the four solutions (Table 2). For measuring the dependency of etching in pH, the membrane was immersed in each buffer solution and was exposed to 2 minutes of laser illumination of increasing intensities. The chip was washed (Milli-Q) and dried before exchanging the buffer. White light images of the membrane were taken before and after the laser exposure using an EMCCD camera and were used to compute the change in reflection through each etched spot (ImageJ and MATLAB). Laser intensity was controlled using a ND filter and monitored using a power meter (Thorlabs).

To confirm that the pH dependence measurements are not biased by different buffer indices, we measured them using a refractometer (Rudolph, J257). The measurements were performed at similar temperature to the thinning experiment (22° C.). The results in Table 2 show similar values for all solutions, indicating that the buffer did not play a role in the PL measurements.

TABLE 2

Refractive index measurements for the different solutions.

| Solution (1 M KCl) | pH4 | pH7 | pH10 | pH12 |
|---|---|---|---|---|
| Refractive index | 1.3405 | 1.3410 | 1.3409 | 1.3402 |

NLDA pulse control: FIGS. 21A-B show a set of 10 laser pulses during the nanopore drilling step, and the resulting nanopore current. The laser pulses widths are indicated at the top. After each pulse the laser is blocked for time $t_{IPD}$ and the system's open pore current is stabilized and measured. With each successive pulse the current is either increased or remain roughly at the same level. See Tables 3 and below for the NLDA variable description. Table 4 provides side by side comparisons of the main differences between the laser drilling system and protocol designed in this publication and previous reports.

TABLE 3

NLDA inputs and parameters

| Input/parameter | Notation | Description |
|---|---|---|
| NLDA inputs (Set by the user) | $P_0$ | Initial laser power |
| | $P^+$ | Laser power increment factor |
| | $\eta_{TH}$ | Current gradient threshold |
| | $I_t$ | Target open pore current |

TABLE 3-continued

NLDA inputs and parameters

| Input/parameter | Notation | Description |
|---|---|---|
| Optimized parameters (Should not be changed between batches) | $t_0$ | Initial pulse duration |
| | d | Delay before applying the η condition during the pulse operation |
| | $t_{IPD}^l$ | Long inter-pulse delay |
| | $t_{IPD}^s$ | Short inter-pulse delay |
| | γ | Pulse time geometrical increment factor |
| | $\varphi_{TH}$ | Polishing threshold |
| | $\rho_{TH}$ | Effectiveness threshold |
| | $\psi_{TH}$ | Significant threshold |
| | R | Consecutive ineffective pulses limit |

List of Notations of Variable and Parameters—NLDA
Measured Variable:
    I—Sampled current.
Notations and Definitions:
    $I_i$—Current sampled at a certain pulse, where the index i denotes the pulse number, last pulse is notated with i=N.
    $t_{Active}$ The time the pulse is active in a specific pulse iteration.

$$\mu^{N-1} \equiv \frac{1}{N-1}\sum_{n=1}^{N-1} I_n -$$

Mean current of the samples that were kept before the last one, N.

$$\rho \equiv \frac{\mu^{N-1}}{I_N} - \text{The pulse effectiveness ratio.}$$

$\psi \equiv I_N - \mu^{N-1}$—The pulse significance difference.
Software Determined Parameters:
    P—Laser intensity.
    $t_{pulse}$—Pulse duration.
User-Set Parameters (Software Inputs):
    $P_0$—Initial laser power.
    $P^+$—Laser power increment factor [% of the maximum intensity].
    $\eta_{TH}$—Current gradient threshold.
    $I_t$—Target open pore current.
Programmer-Set Parameters (Values Rarely Change):
    $t_0$—Initial pulse duration.
    d—Delay before applying the η condition during the pulse operation.
    $t_{IPD}^l$—Long inter-pulse delay.
    $t_{IPD}^s$—Short inter-pulse delay.
    γ—Pulse time geometrical increment factor.
    $\varphi_{TH}$—Polishing threshold.
    $\rho_{TH}$—Effectiveness threshold.
    $\psi_{TH}$—Significant threshold.
    R—Consecutive ineffective pulses limit.
Output:
    $\tilde{I}_t$—Obtained open pore current.

TABLE 4

Laser drilling protocol enhancements and innovation

| Feature | This publication | Previous reports |
|---|---|---|
| Laser wavelength | 405 nm | 488 nm (or 532 nm) |
| PL detector | sCMOS | Avalanche photodiodes |
| Automation | Complete(one-button) automation | Current gradient threshold or manual stopping |

TABLE 4-continued

Laser drilling protocol enhancements and innovation

| Feature | This publication | Previous reports |
|---|---|---|
| Laser mode | Continuous and ms-pulses | Continuous |
| Laser power | Altering | Constant |
| Focusing | Automated-PL assisted | Manual |
| Target nanopore size | Tunning enabled | Not targeted |

Basic methods of membrane thinning/drilling and current/resistance measuring are provided in International Patent Publication WO2020194303. The main control principle implemented in the NLDA involves decision making based on analysis of the drilling past trajectory (as opposed to a single data point), performed in real-time by the setPulseParameters (sPP) function (See Algorithm 1). Two parameters control the next pulse characteristics: the effectiveness and significance of the previous pulse, denoted $\rho$ and $\psi$, respectively. These parameters are used to classify the pulse into one of three categories: "effective and significant", "effective but insignificant" or "ineffective". Examples of this classification are shown in FIG. 20A. The effectiveness parameter, defined as $$\rho \equiv \frac{\mu^{N-1}}{I_N},$$

where $$\mu^{N-1} \equiv \frac{1}{N-1} \sum_{n=1}^{N-1} I_n$$

and N is the last pulse, quantifies the change in the current after the last pulse in comparison to several previous pulses. The R parameter (i.e., R=2) determines the number of the previous pulses to be considered and serves as a limit for consecutive ineffective pulses. The algorithm keeps in memory the currents of the consecutive ineffective pulses, as $\mu^{N-1}$ suggests, and when this number is crossed, i.e., N>R, the sPP function alters $t_{pulse}$ and P to be used in the next pulse. A pulse is assumed to be effective when the effectiveness parameter meets the threshold condition $\rho \leq \rho_{TH}$ (i.e., $\rho_{TH}$=0.8). The significant parameter is defined as $\psi \equiv I_N - \mu^{N-1}$ and similarly a pulse is considered significant when $\psi > \psi_{TH}$ (i.e., $\psi_{TH}$=1 nA). If a pulse is found to be effective but insignificant sPP will keep the same laser intensity and duration for the next pulse. This occurred after the $2^{nd}$ pulse in FIG. 17B, where 207 ms duration was applied in the $3^{rd}$ pulse as well (note the mild current level rise between these pulses). On the contrary, consecutive ineffective pulses will results in increments of these properties, as in the shift between the $4^{th}$ and $5^{th}$ pulses towards the $6^{th}$ one, where the duration grows to 249 ms (in this case R=2). The increment is set by a factor $\gamma$ (i.e., $\gamma$=1.2) that alters the duration in geometrical growth (i.e., $t_{pulse} \leftarrow \gamma t_{pulse}$), which can result a steep pulse-duration increment in cases of long ineffective pulses series. On the other hand, the intensity grows in a linear manner (i.e., P←P+P$^+$, where P$^+$ is the power increment factor with units of % measured from the maximum laser power, e.g., P$^+$=1%), to keep mild steps of power over the duration geometrical growth. Notice that pulses $7^{th}$ to $10^{th}$ are considered ineffective despite the observable growth in the current level, which is a result of the ratio definition of $\rho$. Accordingly, at higher currents levels the threshold becomes much less permissive. This causes to linearly increase the intensity when the pore is already open yet has not reached its final targeted size. Thus, it usually happens at the beginning of an ineffective series when the duration geometrical increment is still at its short negligible period (mild increments). Such behavior is found to be beneficial to the polishing stage. This incremental behavior ceases when a significant pulse appears. Then, the significance parameter crosses a threshold value ($\psi > \psi_{TH}$), which causes the duration and intensity to be restored back to their initial low values (e.g., $P_0$=14.4 mW and $t_0$=100 ms) and ensure pulsing in a fine-tuning mode. This is demonstrated in FIG. 20A, where a significant current rise following the $6^{th}$ pulse is considered, resulting the shortening of the $7^{th}$ pulse back to 100 ms. This behavior of substantial pore expansion is often visible in the transition between the drilling and polishing stages, as demonstrated in FIG. 16C, where the pulses are becoming weaker and shorter. Note that FIG. 20A represents only an example taken from a specific experiment, where in fact each of the experiments results in a different trajectory of pulses with diversity of durations and intensities, according to the initial conditions.

Another performance that the NLDA alters is the duration of $t_{IPD}$, i.e., how much time the algorithm waits before sampling $I_N$. This simple yet important distinction sets the threshold between the drilling and polishing modes. By passing the "polishing threshold" $\varphi_{TH}$, an optimized parameter defined with an absolute current level, the NLDA switches between two $t_{IPD}$ values: short $t_{IPD}^s$ and long $t_{IPD}^l$ for drilling and polishing, respectively. In this way the NLDA alternates between two types of behaviors: the short inter-pulse delay allows the overall process to run faster, whereas the long inter-pulse delay permits a more precise measurement of the ion current I, after waiting the extended time. This might alternate several times in different manners during each specific pulse trajectory, but usually will end with a series of consecutive polishing pulsing, as FIG. 16C suggests. FIG. 20B, displays the transition section between drilling and polishing triggered by crossing the threshold $\varphi$=1 nA and the resulting doubling of $t_{IPD}$ from 1 s to 2 s between the $2^{nd}$ and $3^{rd}$ pulses.

A summary flow chart of a method of the invention is provided in FIG. 33.

---

Algorithm 1: Nanopore laser drilling algorithm (NLDA)

1: Autofocus
2: //Thinning: "Keep laser on until the current penetrates the membrane for the first time"
3: P ← $P_0$ //initialize
4: Turn laser on
5: While laser is on
6:    If VI ≥ $\eta_{TH}$

| Algorithm 1: Nanopore laser drilling algorithm (NLDA) |
|---|
| 7:     Turn laser off
8: //Pulsing:
9:   $t_{pulse} \leftarrow t_0$; $I_N \leftarrow I$ //(initialize - set last current after turning off the laser as the last sampled current)
10: While True //(to stop the loop needs to reach the break statement, can also be stopped via the UI)
11:     Wait $t_{IPD}^S$
12:     If $I \geq \varphi_{TH}$ //"Polishing? Else drilling"
13:         Wait $t_{IPD}^I - t_{IPD}^S$
14:     $I_N \leftarrow I$ (keep last current sample N)
15:     If $I_N < I_t$ //"Did the current reach the target OPC?"
16:         $t_{pulse}$, P $\leftarrow$ setPulseParameters($i_S^N$)
17:         Turn pulse on
18:         If $t_{pulse} < d$
19:             Wait $t_{pulse}$
20:             Turn pulse off
21:         else
22:             Wait d
23:             While pulse is on //"Track an abrupt expansion"
24:                 If $VI > \eta_{TH}$ or $t_{active} \geq t_{pulse}$
25:                     Turn pulse off
26:     else
27:         break
28:
29: Function setPulseParameters($i_S^N$)
30:     If $\rho \leq \rho_{TH}$ //"Is the pulse effective?"
31:         If $\psi > \psi_{TH}$ //"Is the pulse significant?"
32:             $t_{pulse} \leftarrow t_0$
33:             $I \leftarrow P_0$
34:             Keep $I_N$, flush the previous kept currents ($I_1$, ..., $I_{N-1}$)
35:         else if $N - 1 \geq R$ //"Consider number of consecutive ineffective pulses"
36:             $t_{pulse} \leftarrow \gamma t_{pulse}$
37:             $P \leftarrow P + P^+$
38:             Keep $i_S^N$, flush the previous kept currents ($I_1$, ..., $I_{N-1}$)
39:     else
40:         Add $I_N$ to the previous kept currents ($I_1$, ..., $I_{N-1}$)
41:     Return $t_{pulse}$, P |

Membrane fabrication and device assembly: 4-inch ~350 μm thick silicon wafers were coated by LPCVD with layers of ~500 nm silicon dioxide ($SiO_2$) and ~50 nm $SiN_x$ from both sides. The $SiN_x$ refractive index was measured by ellipsometry (FS-1, Film sense) and confirmed to be n=2.29±0.01. Each wafer was spin-coated with a photoresist (AZ1518, Micro chemicals) applied by direct photolithography with a custom window-pattern mask (written with Microwriter ML3, Durham Magneto Optics Ltd), and finally developed (5035S, Novo). Then the first $SiN_x$ layer was etched and removed by reactive ion etching (RIE, diener electronic PCCE machine). The exposed $SiO_2$ was dissolved with buffered oxide etch (BOE) to complete the hard mask. Then KOH was used to etch the Si layer all the way through for 19 hours at 57 degrees Celsius in a custom-built bath for maintaining the temperature and flow in the solution. Another BOE etching was applied to remove the second $SiO_2$ layer, resulting in a ~50 nm $SiN_x$ free-standing membrane. For the $TiO_2$ samples, the membrane was coated using atomic layer deposition (ALD) according to the manufacturer's recipe (GEMStar XT) to obtain a 10 nm layer (applied before the KOH step).

Each chip is mounted onto a Teflon holder by PDMS, which is used to isolate the two chip sides. The holder is placed in a Teflon cell to form two chambers of separated aqueous solution. A custom seating is installed above the objective to hold the Teflon cell, where its bottom side is glued to a thin glass cover slide that allows the laser to be focused on the chip through the aqueous solution.

Optical setup: A custom-made confocal set up was used for the NLDA as described in FIG. 2a. The excitation path includes the Toptica iBeam smart lasers (488 nm or 405 nm, including clean-up filters) and Thorlabs neutral density filters and mirrors. All are directed through a Zeiss Axiovert 200M microscope frame into a Zeiss Apochromat water objective (NA=1.15, 63×) which focuses the laser into a diffraction-limited spot. In the emission path, the fluorescence and reflected laser from the sample are collected by the same objective, where a Semrock dichroic mirror of 405 nm (Di01-R405/488/532/635-25×36), and 430 nm or 488 nm (laser dependent) long-pass filter (FF01-430 or—496/LP-25) are used to selectively capture the PL and measure it by an Andor Zyla 4.2 sCOMS camera (PL images are sampled at 33.33 Hz). The laser intensity was measured by a Thorlabs power-meter before the objective lens. A PI P-561 piezo stage controlled by an E-710 controller is installed above the objective and is used to move the nanopore device in sub-micrometer steps laterally and axially. An Axon Axopatch 200B amplifier is used to measure the electrical current (sampled at 125 KHz) and apply voltage across the membrane. All the instruments and devices are controlled by a custom Lab VIEW software, connected through serial connections and/or digital/analog input and outputs of NI PCI-6602 and NI PCI-6154.

Aqueous solution preparation: Drilling only experiments were performed in a salt solution containing 1 M KCl and 0.02M sodium bicarbonate-based buffer (18:22 ratio of sodium bicarbonate and sodium carbonate, "Sod-Bic") titrated to pH 10. For in situ translocation experiments, 173 μM sodium-dodecyl sulfate (SDS) was added to the buffer.

TEM imaging and EDS analysis: EM Imaging: High-resolution images were acquired with an FEI Titan Themis Cs-Correct HR-S/TEM, The low loss energy spectrum was measured in scanning transmission electron microscopy (STEM) in increments of 20 nm and was used to automatically generate relative thickness maps using Digital Micrograph software (Gatan). Composition Analysis: Chemical mapping of the SiNx membranes was performed using EDS (Dual Bruker XFlash6) and STEM based on core-loss EELS. The EDS quantification was done using Velox (Thermo Fisher) and EELS quantification was done using the Digital Micrograph software (Gatan).

Signal and image processing: All postprocessing of the LD experiments and image processing during laser focusing were computed with a custom Matlab (Mathworks) code. All graphs were plotted and fitted in IgorPro (Wavemetrics).

Signal processing: A MATLAB code was used to post-process the NLDA traces. The main goal of the code was to clear the PL and current traces from parts in which the laser was either off or on, respectively (as was done for example in the filtered traces in FIG. 16C, compared to their raw traces in FIG. 24). Both traces were processed in a similar way, to remove the transition phases of switching on/off the laser: first they were subjected to thresholds filtering. Then, a 1D median filter was used to clean the signals from abrupt changes which are due to the transition periods. On the last step the signals were interpolated with a linear kernel and smoothed to create continuous traces that represent the overall drilling behavior.

Image processing: To show how the laser etching progresses with its irradiation, the FWHM of the nanowells from FIG. 1a were estimated by a simple image processing technique. Each etched region from the original image (FIG. 15A) was extracted separately with inverted gray levels (FIG. 29A). Then, as shown in FIG. 29B, the images were binarized by a certain threshold to obtain their brightest pixels. Each point in main FIG. 15B was estimated by $$FWHM \approx r \cdot \sqrt{\sum \# \text{ of bright pixels}}, \text{ where } r = \frac{1}{100} \frac{um}{\text{pixel}}.$$

Software programming: Control and automation software including the NLDA algorithm (algorithm 1) was programmed in LabVIEW (National Instruments).

Sample preparation: The protein sample was prepared at high concentration which was further diluted by 100-fold for the nanopore experiment. For preparing a denatured protein sample, a standard protocol was followed: 10 µg/ml of the Carbonic Anhydrase protein was dissolved into 1 M PBS buffer. To disrupt the disulfide interaction of the cysteine residue, 5 mM of TCEP was added to the reaction mixture. 350 µM of ionic surfactant SDS, which is used for protein denaturation in combination with heat, was also added to the reaction mixture. The reaction was allowed to shake for 30 min at 25° C. and 300 rpm. Furthermore, to denature the protein, the reaction mixture was heated at 90° C. for 5 min. The reaction was allowed to cool again to room temperature before it was added to the nanopore device cis chamber for the experiment.

Numerical simulations: Numerical simulations were conducted via Comsol Multiphysics (Comsol Inc.) to solve the Nernst-Planck-Poisson equations in a finite element method.

We used numerical simulations to solve the Nernst-Planck-Poisson equations and produce the electric potential and current density vectors distribution in the nanopore vicinity, using different form factors models (FIG. 32). We compared between a cylindrical (or a naïve) nanopore model, an hourglass shape which has been shown to be produced in TEM-fabricated pores, and the double Gaussian form factor model of the invention for the laser-drilled nanopores, as illustrated in FIG. 30. Simulations were implemented by a finite element method in Comsol Multiphysics (Comsol Inc.), which involves the Electrostatics and Transport of Diluted Species modules.

Basic geometry and dimensions of the electrolyte chambers were built as in Wanunu, M. et al., Electrostatic Focusing of Unlabelled DNA Into Nanoscale Pores Using a Salt Gradient. Nat. Nanotechnol. 2010, 5 (2), 160-165, together with a 50 nm-thick membrane. We divided the geometry into two domains—the membrane and the solution, where all the computations take place in the solution and around the membrane. The geometries were built in a 2D axisymmetric space dimension, therefore assuming cylindrical axial symmetry (z-axis). Moreover, we assumed steady state (stationary solution), charge conservation, zero charge on the membrane surface and zero flux through the membrane.

Under these assumptions we solved the following equations for each of the dissolved ions i:

$$\nabla \cdot J_i = 0 \,|\, J_i = -D_i \nabla c_i - z_i \mu_i e F c_i \nabla V \tag{1}$$

$$\nabla^2 V = -\frac{\rho_v}{\varepsilon_0 \varepsilon_r} \tag{2}$$

Where J is the molar flux, D is the diffusion coefficient, c is the concentration, z is the charge number, µ is the mobility, e is the elementary charge, F is the Farady constant, V is the electric potential, $\rho_v$ is the volumetric charge density and $\varepsilon_0 \varepsilon_r$ is the permittivity. The Nernst-Einstein relation was used by the software to extract the mobility:

$$\mu = \frac{D}{RT} \tag{3}$$

where R is the gas constant and T is the absolute temperature.

The diffusion coefficients of the $K^+$ and $Cl^-$ ions used were based on experimental measurements of the hourglass model:

$$D_{Na} = 6 \times 10^{-9} \frac{m^2}{s}\, D_{Cl} = 1.22 \times 10^{-9} \frac{m^2}{s}$$

for sodium and chloride, respectively. These were then configured in the Gaussian form factor to numerically evaluate the laser-drilled pores.

Regarding initial conditions, we used V=0 for the electric potential and C=1M for the species concentration of sodium and chloride inside the solution. The boundary conditions included V=0.3 V on the bottom boundary of the bottom chamber, and a ground on the upper boundary of the upper chamber. Both boundaries are defined with C=1 M of sodium and chloride.

To obtain the Gaussian-profile of the pore vicinity we assumed a diffraction limited laser intensity profile according to our laser's wavelength λ and our optical system numerical aperture NA.

The computed back-to-back Gaussians were separated by the length defined as the effective thickness of the pore, i.e., defined as membrane thickness divided by 3, as FIG. 31 suggests. Then, the membrane is being cut by the shape of the Guassians to obtain the Gaussian form factor geometry. A gap between the symmetry axis and the effective thickness area defines the nanopore radius. FIG. 31 shows how the Gaussians are drawn upon the membrane before the cut parts are removed.

Example 1: Laser-Etching of Freestanding $SiN_x$

We first developed a procedure for etching freestanding $SiN_x$ with a continuous-wave blue (488 nm) solid-state laser. It begins by assembling a Si-supported SiNx membrane (typically 40-45 nm thick) in an optically accessible flow cell, which is then mounted on top of a high NA microscope objective in a homebuilt confocal setup (FIG. 1A). The setup is equipped with an EMCCD for widefield viewing and an avalanche photodiode (APD) detector for high temporal resolution sensing of the photoluminescence (PL) intensity. For alignment, we set the blue laser at low intensity (40 μW) to prevent unintentional etching and bring the membrane into focus of the laser spot. Once aligned, the laser intensity is increased to full power (~45 mW) for the etching step, but in cases of a high index of refraction and/or high pH values, lower laser intensities were applied.

Figure 1B:
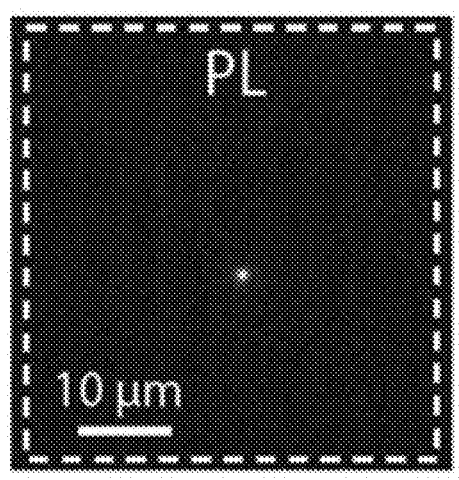
Figure 1C:
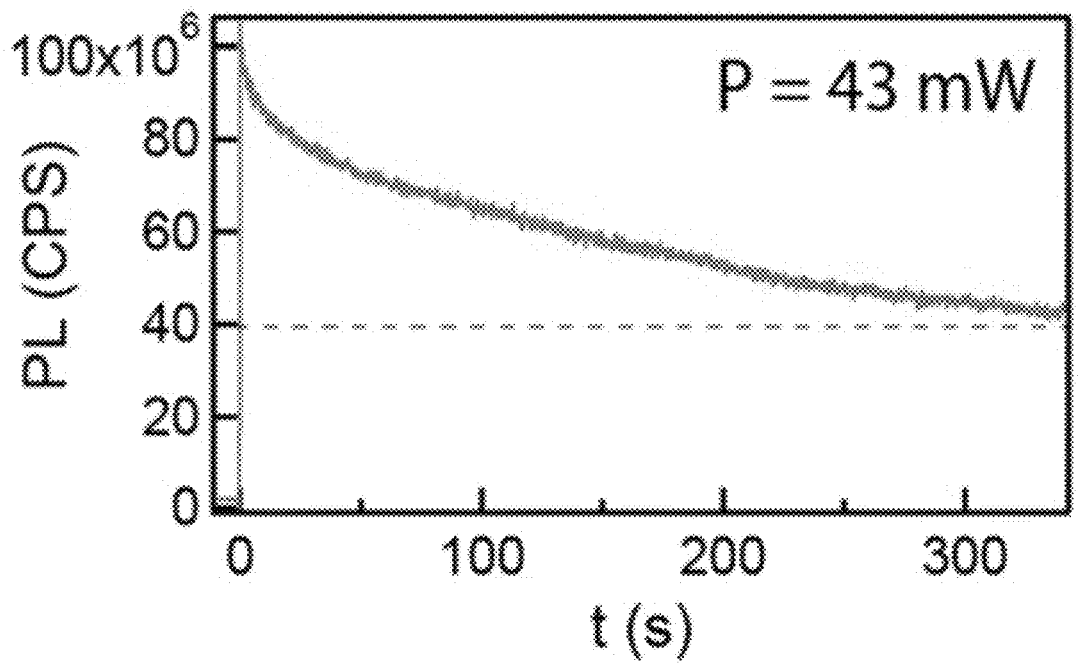
Figure 1D:
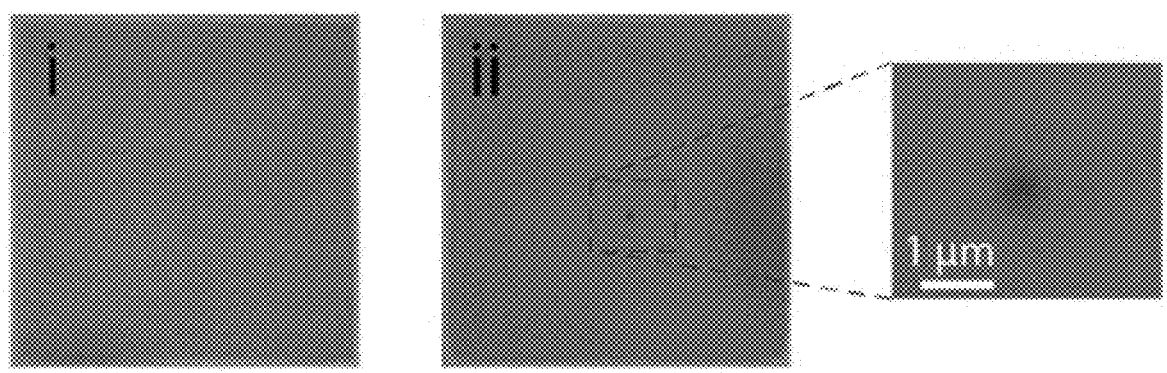

Notably, we observed that under high laser intensity, a bright PL emission was visible by our EMCCD camera (FIG. 1B). The measured PL intensity exhibited a decay over time before reaching a near plateau level after roughly 300 s (FIG. 1C). We confirmed that the decay in PL is not due to mechanical drift and is in fact irreversible: momentarily switching off the laser beam and then switching it on again showed that the PL level retuned to the same level at which the laser was switched off (and not to the initial level). Furthermore, widefield optical inspection of the membrane revealed a darkened spot at the point where the material was illuminated by the laser (FIG. 1D). The material darkened proportionally to the PL reduction, and this spot could not be revived by solvent or acid cleaning.

Figure 2:
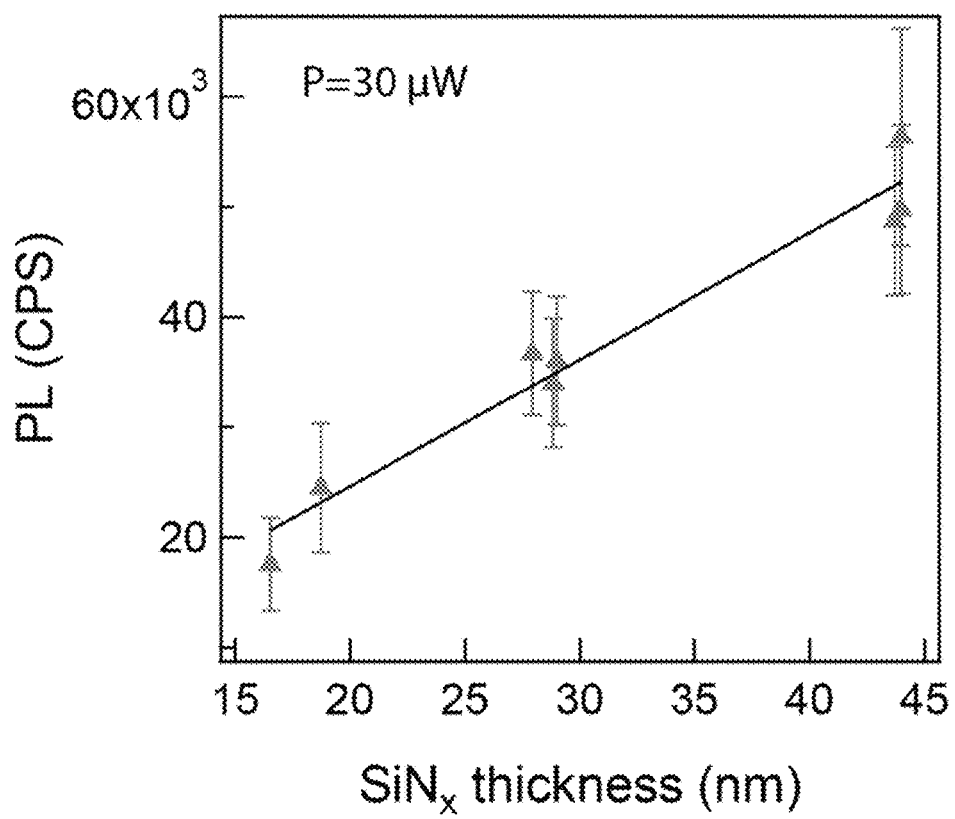
FIG. 2. Photoluminescence (PL) intensity calibration as a function of $SiN_x$ thickness. The PL in counts per second (CPS) was measured by the APD during laser-exposure (488 nm, 30 µW) for 6 chips of different membrane thickness. Prior to the PL measurements, the membrane thickness was measured by ellipsometry. Thicker membranes result in higher PL.

As contrast under white-light illumination typically indicates a difference in material thickness, to further characterize this phenomenon we fabricated a series of freestanding SiNx membranes from the same stock material, using reactive ion etching (ME) to obtain different final thicknesses. Accurate thickness measurements were made by ellipsometry after performing a careful calibration using a factory-supplied model specimen. The chips were then mounted in our optical setup and the PL level was determined under otherwise identical conditions. Our results, summarized in FIG. 2, show a linear relationship between PL and the $SiN_x$ membrane thickness. We note that, as expected, the measured PL intensity varies sharply with the distance between the objective lens and the membrane and reaches a maximum value when the laser spot is centered in the z direction on the membrane. Hence the measurements shown in FIG. 2 involved careful maximization of each PL read in the z direction. Measurements were performed using an attenuated laser (30 μW) to avoid etching of the membrane and remain constant over time. The error bars reflect the standard deviation in the PL intensity over 1 minute of measurement.

Figure 3A:
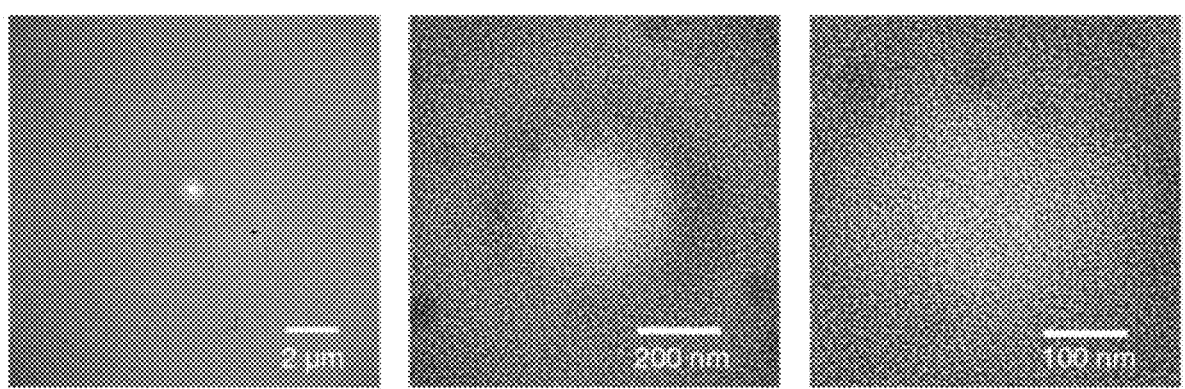
FIGS. 3A-E. Thickness characterization of a laser-etched spot. (3A) TEM images at 195×, 39000× and 75000× (left to right). The lighter region corresponds with higher transmittance and thus thinner material. (3B) TEM images of laser-etched thin regions. (Upper left) TEM image at 7500× of two thin regions corresponding to 2 different laser exposure durations: 1 and 3 minutes (left to right). (Upper right) TEM image at 21000× of one thin region after 1 minute of laser exposure. (Lower) TEM image at 16500× of a thin region after 1 minute of laser exposure (left), and a zoom-in at 75000× (right). (3C) TEM thickness map of an etched spot in nanometers. (3D) Blue curve—TEM thickness map. Purple curve—normalized photoluminescence (PL) scanned in the x direction with a 30 nm step size. Red curve—simulated normalized PL based on a convolution of a diffraction-limited Gaussian, representing the laser beam, with the TEM thickness map. (3E) Laser-etching wavelength dependency. Free-standing 40-45 nm thick $SiN_x$ were subjected to ~45 mW 488 (blue), 532 (green), and 645 (red) laser intensities for 2, 4 and 6 minutes. Consequently, the membranes were imaged using a light microscope in transmission mode. The grayscale intensity values are shown as arbitrary greyscale units, obtained by averaging the pixel values at the center of the etched regions. Experiments were performed in triplicates. A higher pixel intensity corresponds to greater light transmittance and thus a thinner membrane region.
Figure 3B:
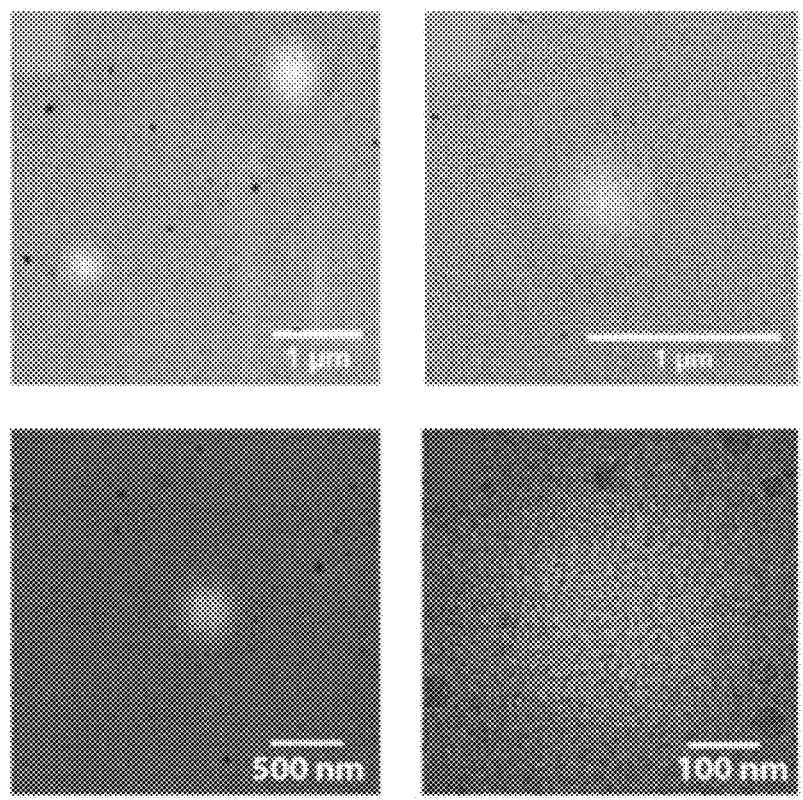
Figure 3C:
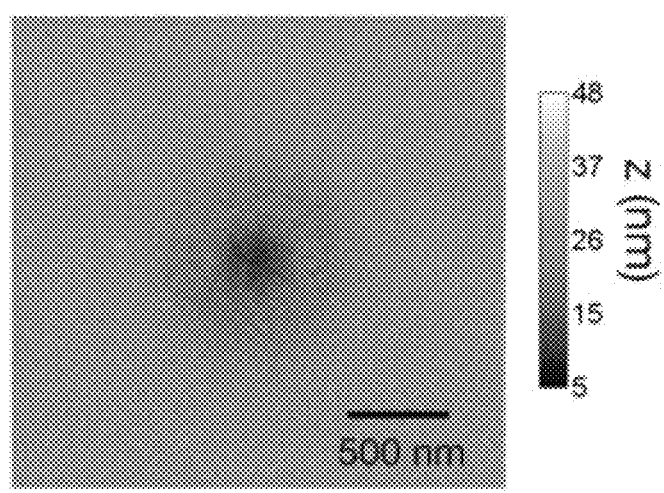

We next imaged the samples by Transmission Electron Microscopy (TEM) to determine whether the darkened membrane spot caused by the laser was in fact due to material removal and not a type of laser-induced chemical reaction or adsorption process. Indeed, the TEM images reveal that the material had thinned at the position of the laser focus (FIG. 3A-B). Moreover, the TEM images show that the material thins non-uniformly: the thickness profile closely follows the intensity point-spread function (PSF) of the laser beam used to induce thinning, where etching occurs fastest at the center (FIG. 3C). See Methods for a description on making the TEM thickness map.

Figure 3D:
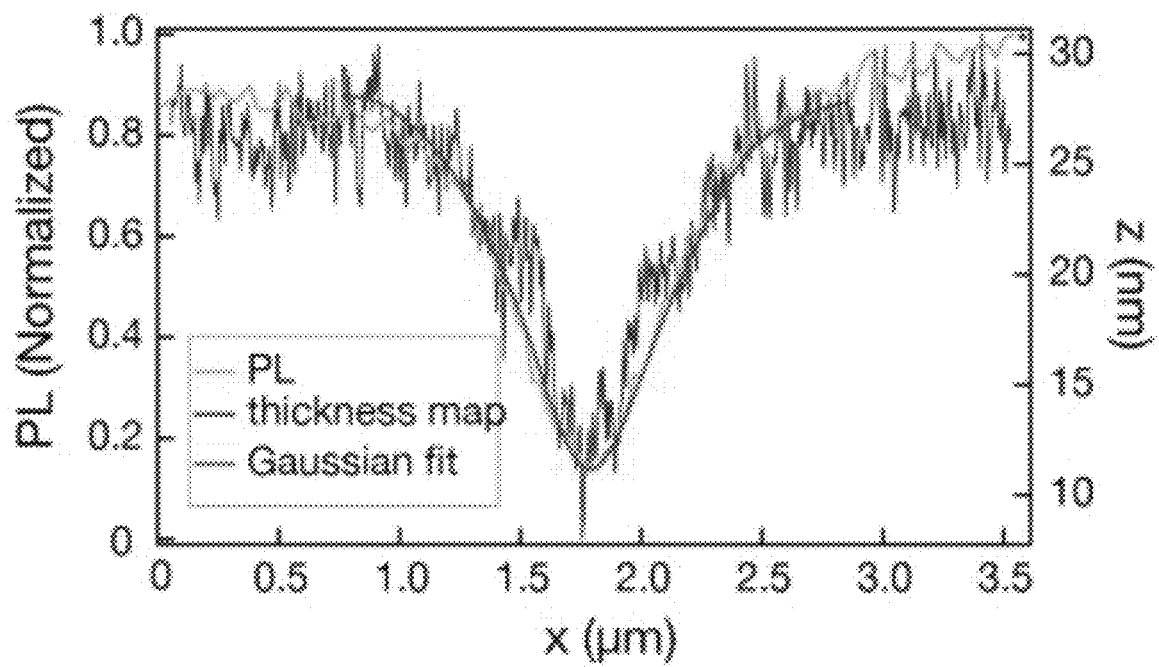

After establishing that the laser etches $SiN_x$, we formulated a relationship between measured PL and etch depth which is consistent with the TEM analysis. After two minutes of laser exposure, we lowered the laser intensity to prevent etching and scanned in the x direction with a 30 nm step size while measuring PL intensity. The generated 1D PL profile and TEM thickness map were both normalized and overlaid on the same graph (FIG. 3D, orange and blue curves, respectively). As can be seen, the PL curve matches the true $SiN_x$ thickness, deviating slightly because of practical limitations of the optical setup. We simulated a PL curve based on a convolution of a Gaussian PSF, representing the laser beam, with the TEM thickness map (FIG. 3D, red curve). Overlaying the modelled data on the same graph shows a tight fit with the PL measurement, with a PSF full width at half maximum (FWHM) of 325±15 nm. This compares favorably with the diffraction-limited FWHM of 330±20 nm for PL emission collected by an objective lens with a numerical aperture (NA) of 1.15. Therefore, we can reliably use the PL measurement to infer the membrane thickness.

Figure 3E:
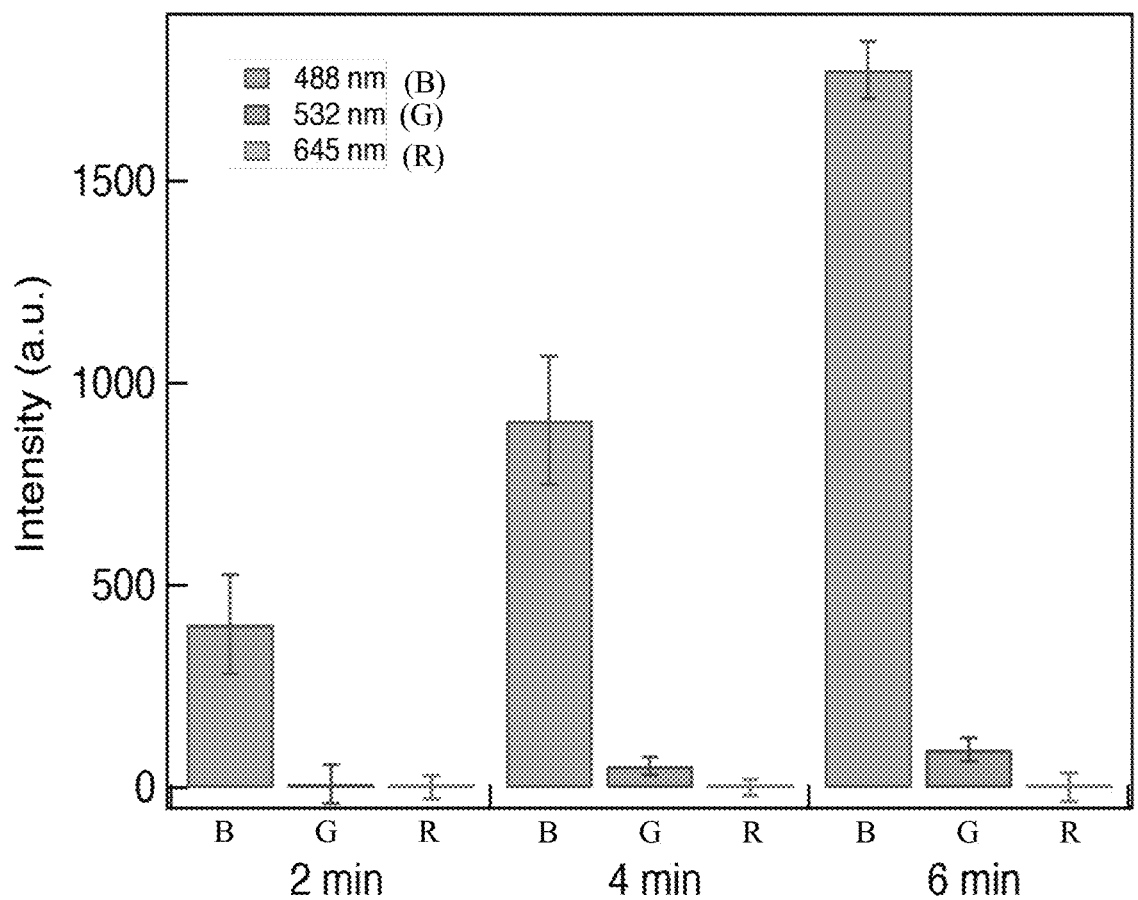

We found that the etch rate is significantly reduced at low laser intensity and is practically undetectable for 488 nm laser intensities <1 mW over the course of our measurements. The etch rate for the 488 nm laser at an intensity of ~45 mW was found to be up to 25 nm/minute. Interestingly, red laser (645 nm) induced no appreciable membrane thinning over a similar timescale, while green laser (532 nm) focused on the membrane at the same power as the 488 nm laser, resulted in roughly an order of magnitude less thinning, indicating that the etching mechanism is dependent not only on the laser intensity but also on its wavelength (FIG. 3E). This is consistent with a previous study which did not report any membrane thinning despite using a comparable laser power (~45 mW, 785 nm). Interestingly, we found that etching also proceeds in ultrapure water (18.2 MΩ×cm) and not just in KCl buffer. Although slow $SiN_x$ etching in water has been reported before in the literature, it required the use of sub- or super-critical water with temperatures in the 200° C. range and a pressure of 10 MPa. Our finding that the 532 nm laser produced much less $SiN_x$ thinning than the 488 nm laser at the same power suggests that the etch process is likely not temperature-activated but rather follows a wavelength-dependent photochemical etching. It is known that differences in laser-etching rates is a consequence of differences in spatial-electron hole pair density, which is a function of their respective absorption coefficient for a particular material.

Example 2: Nanopore Fabrication and Validation

Based on our observation that a ~45 milliwatt-intensity blue laser etches $SiN_x$, we attempted to fabricate nanopores by progressively thinning the membrane until the point of nanopore formation. For this, we monitored the ionic current across the membrane, applying a 300 mV transmembrane potential via cis/trans-immersed AgCl electrodes connected to an Axon 200B amplifier. We simultaneously measure the PL as a way to track the fabrication progress. An example experiment with concurrent ionic and PL feedback is given in FIG. 4A. In this example, we observed an increase in ionic current after roughly 145 seconds, which we attribute to the formation of an ionic passageway through the membrane. The current continues to rise until the laser is deactivated, which we associate with nanopore growth. Notably, upon pore formation the ~45 mW laser also causes an increase in electrolyte conductivity hence, turning the laser off causes the current to drop. The open pore conductance then stabilizes over the next few minutes, usually deviating at most 2 nS from its initial value. The final conductance level increases with the time that the laser is kept on after the initial formation of the pore.

Figure 4B:
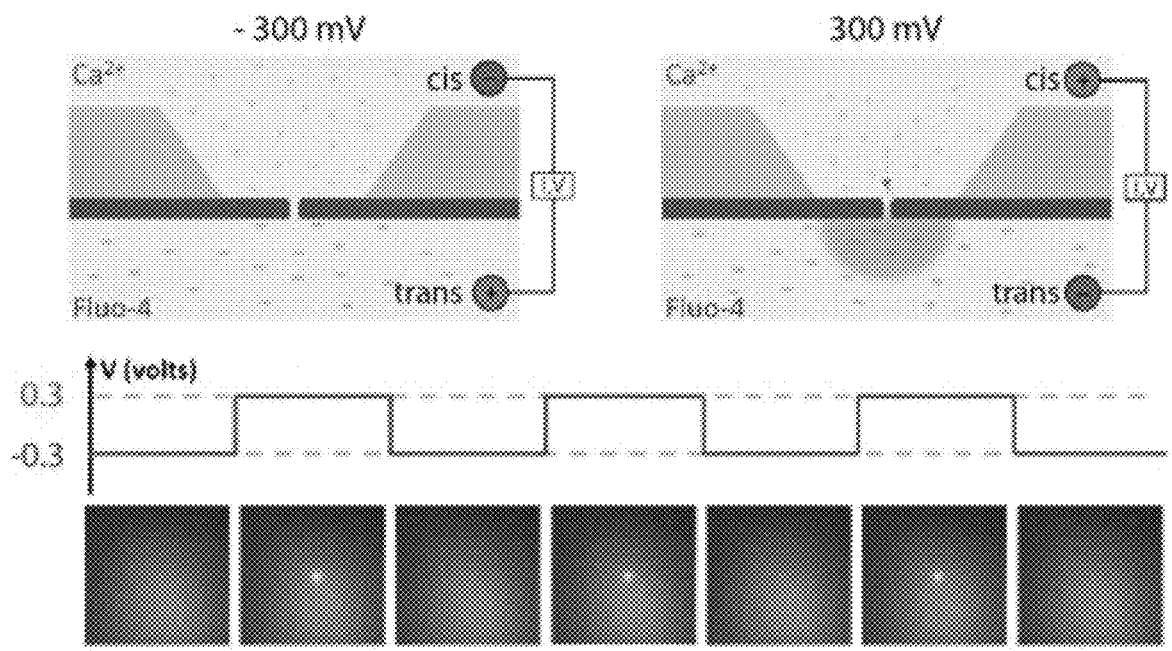
Figure 5A:
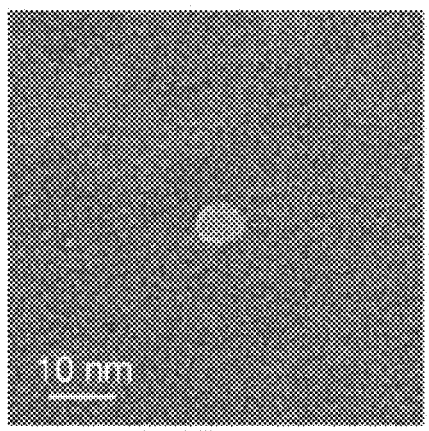
FIG. 5A-N. Noise and functionality of a laser-etched nanopore. (5A) TEM image showing a nanopore with a diameter of 6.5 nm. Compared to the peripheral membrane, the nanopore is very bright, owing to an unobstructed electron beam path. (5B) Three examples of measured photoluminescence (red curve) and ionic current (grey curve) during laser-exposure. A nanopore was formed after (top) 400 s (middle) 920 s and (bottom) 140 s. (5C) Power spectral density (PSD) plot of a nanopore for an applied bias of 300 mV. The inlet shows the corresponding current-voltage (IV) curve for this nanopore, with a linear fitting ($R^2$>0.99). (5D) Scatter plot of dsDNA translocation events. The trans chamber was biased to 300 mV to drive translocation of 300 pM 5054 bp dsDNA from cis to trans. The size of the pore is 3.1±0.3 nm based on the current blockage level/molecular ruler model. (5E) A concatenated ionic current trace showing sample dsDNA translocation events.

We first validated that a thoroughfare path was truly made in the membrane and that the measured current was not caused by surface charging or some other effect. To do so, we loaded the cis side chamber with calcium ($Ca^{2+}$) and the trans chamber with Fluo-4, and illuminated the entire membrane at 488 nm while monitoring it with a CCD (FIG. 4B, upper panel). For there to be a path through the membrane, the fluorescence signal should sharply increase when the applied cis/trans bias is positive, as the $Ca^{2+}$ would be driven through and activate Fluo-4. Indeed, as shown in FIG. 4B (lower panel), we observed a fluorescent signal at the exact position where the material was etched. We next sought to corroborate our calcium-imaging data with TEM data. After a laser drilling experiment, we allowed the OPC to stabilize for over 15 minutes. We then immersed the $SiN_x$ chip in ultrapure water to remove salt residue. FIG. 5A gives an example TEM image of a 6.5 nm nanopore formed in under 5 minutes, which was a typical fabrication time in a 40-45 nm thick membrane based on >30 trials (100% yield).

Figure 5B:
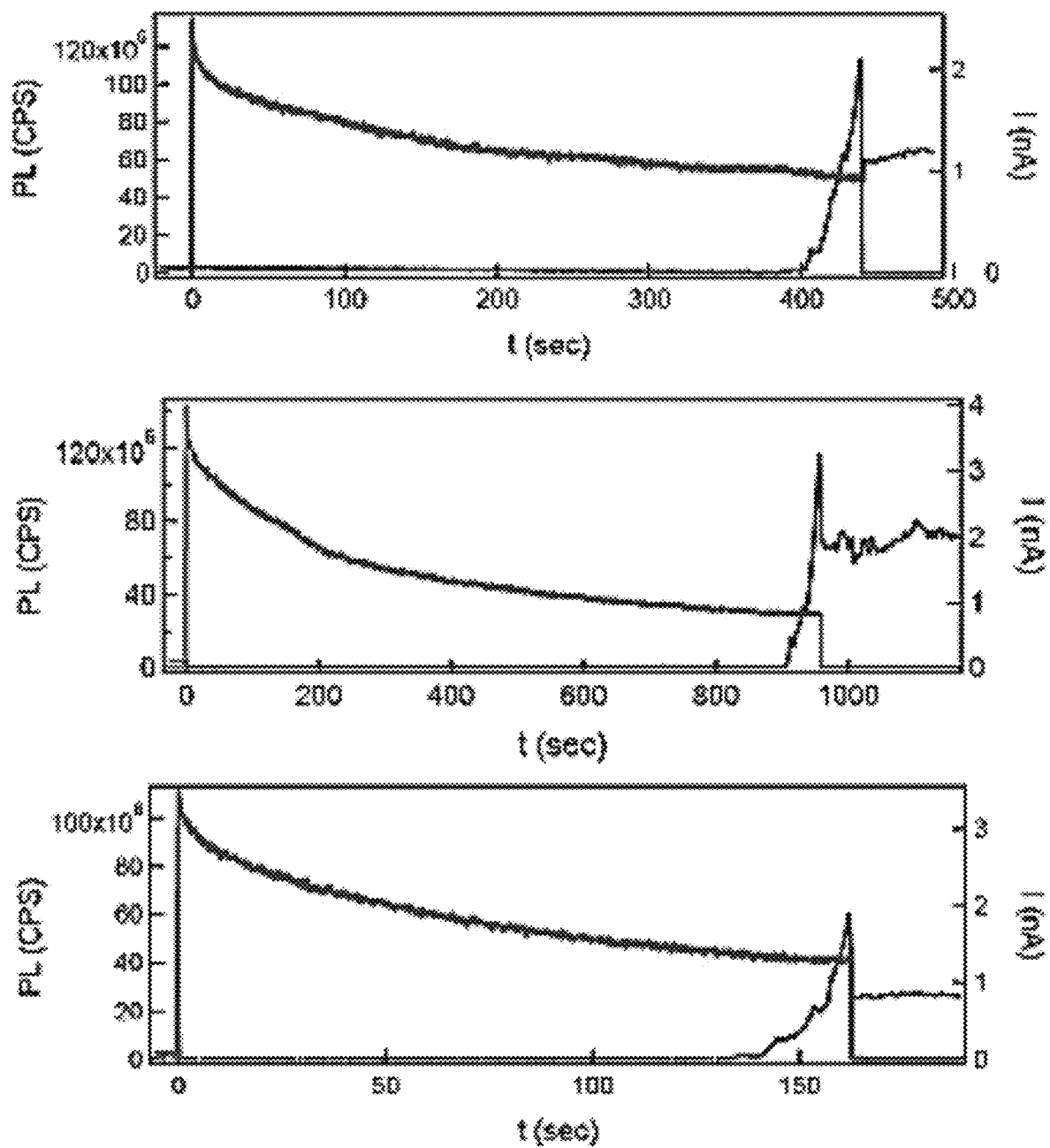

As we show, by choosing a current threshold for laser shutoff, we are able to reproducibly fabricate both small (1 nm), medium (5 nm), and large (over 10 nm) nanopores according to the sensing requirement (FIG. 5B, Table 1). Given that our nanopore fabrication strategy is markedly different than existing techniques such as CBD or TEM-drilling, we cannot expect that the standard conductance model for pore size determination applies; in particular, this model assumes an effective nanopore height equivalent to or one third of the membrane thickness, depending on the method employed. Instead, we can reliably estimate the nanopore diameter according to the translocation blockage level using a molecular ruler of known dimensions, such as dsDNA (2.2±0.1 nm), and the following equations:

$$i_O = \frac{V}{\frac{4l}{\pi d^2} + \frac{1}{d}} \sigma \quad (1)$$

$$I_B \equiv \frac{i_B}{i_O} = \left(1 - \frac{a^2}{d^2}\right) \quad (2)$$

where $i_O$ and $i_B$ are the open and blocked pore current levels, respectively, l is the local membrane thickness, d the pore diameter, a the solution conductivity and a is the analyte diameter. To demonstrate the extent by which the conductance model needs to be adjusted, we calculated the effective thickness for a pore with an OPC of 11±0.7 nS and a diameter of 3.2±0.3 nm. Remarkably, we get an effective thickness of 4-6 nm, which is up to 11 times smaller than the surrounding membrane and is consistent with our observation that the membrane gradually thins to the point of nanopore formation. Such ultrathin architectures are highly desirable due to their larger conductance and hence improved spatial resolution and have therefore been the subject of much research.

TABLE 1

Table of nanopores fabricated by laser-etching.

| Pore | OPC (± 0.1 nA) | Pore | OPC (± 0.1 nA) | Pore | OPC (± 0.1 nA) |
|---|---|---|---|---|---|
| 1 | 0.5 | 11 | 1.5 | 21 | 2.4 |
| 2 | 0.5 | 12 | 1.7 | 22 | 3.1 |
| 3 | 0.7 | 13 | 1.9 | 23 | 3.6 |
| 4 | 0.8 | 14 | 2.0 | 24 | 3.9 |
| 5 | 0.9 | 15 | 2.1 | 25 | 4.3 |
| 6 | 1.1 | 16 | 2.1 | 26 | 4.4 |
| 7 | 1.1 | 17 | 2.1 | 27 | 5.4 |
| 8 | 1.2 | 18 | 2.2 | 28 | 5.8 |
| 9 | 1.3 | 19 | 2.2 | 29 | 6.1 |
| 10 | 1.3 | 20 | 2.2 | 30 | 8.1 |

The table is ordered according to the open pore current (OPC) from smallest to largest. In order to show that a wide distribution of pore sizes is possible, the laser was kept on following pore creation to expand the pore. The open pore current (OPC) was recorded 1-2 minutes after the laser was turned off.

Figure 5C:
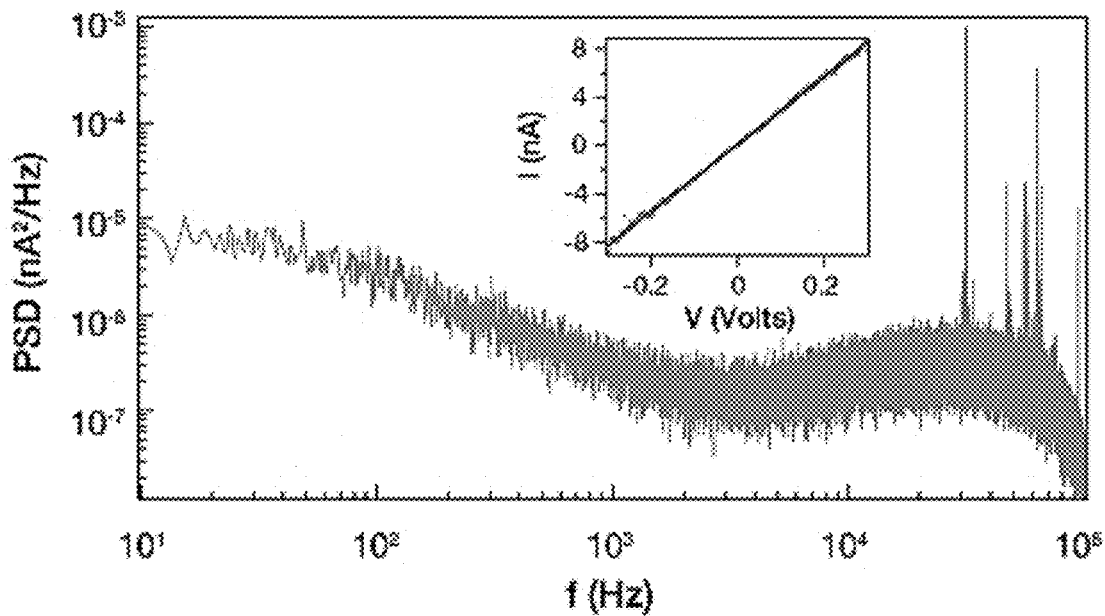

We next evaluated the noise characteristics of laser-etched nanopores. FIG. 5C shows the power spectral density (PSD) plot of a nanopore for an applied bias of 300 mV after allowing the nanopore to stabilize in KCl buffer. Similar to TEM-drilled nanopores, two sources of noise dominate the PSD: high-frequency background noise associated with the chip capacitance, and low-frequency flicker noise with $1/f^{\alpha}$ dependency. At an applied voltage of 300 mV, these nanopores typically exhibit an $i_{RMS}$ in the range of 100-200 pA. To assess ionic current rectification, which occurs due to a geometric or surface charge asymmetry along the axis of current flow, we varied the potential from −300 to +300 mV with equimolar salt concentrations in the cis/trans chambers. The resulting IV curve is linear ($R^2$>0.99), indicating minimal rectification and therefore a symmetric geometry (FIG. 5C, inset). This suggests that the laser-induced etch mechanism occurs on both sides of the membrane equally to produce a very thin hourglass-shaped nanopore.

Figure 5D:
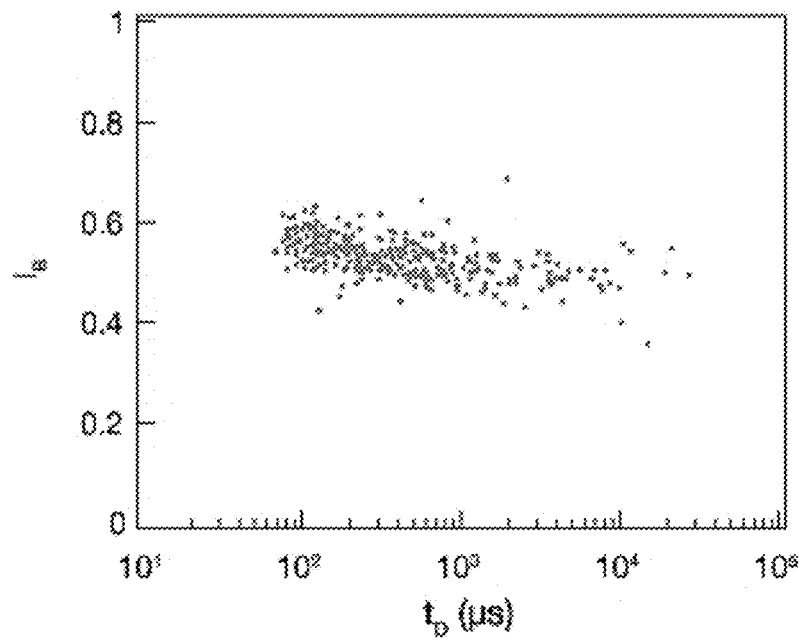
Figure 5E:
Figure 5F:
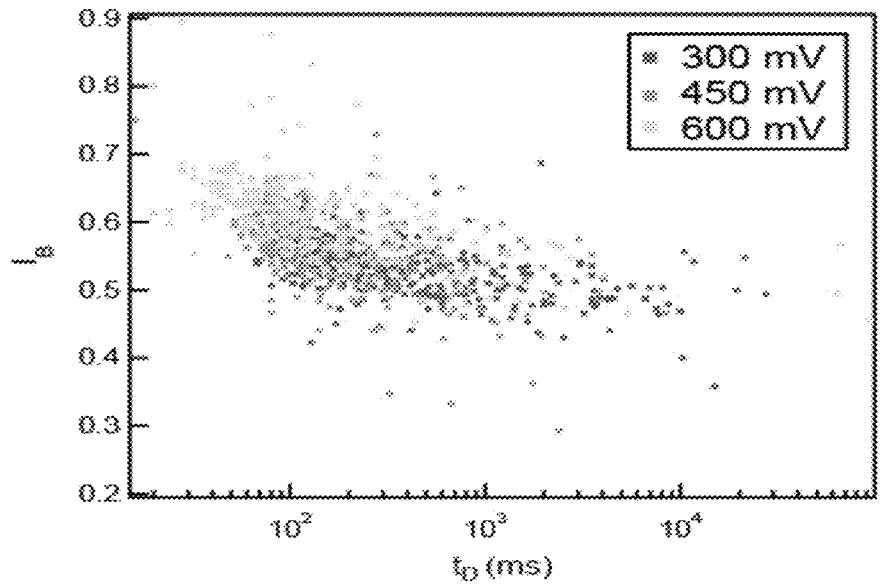
Figure 5G:
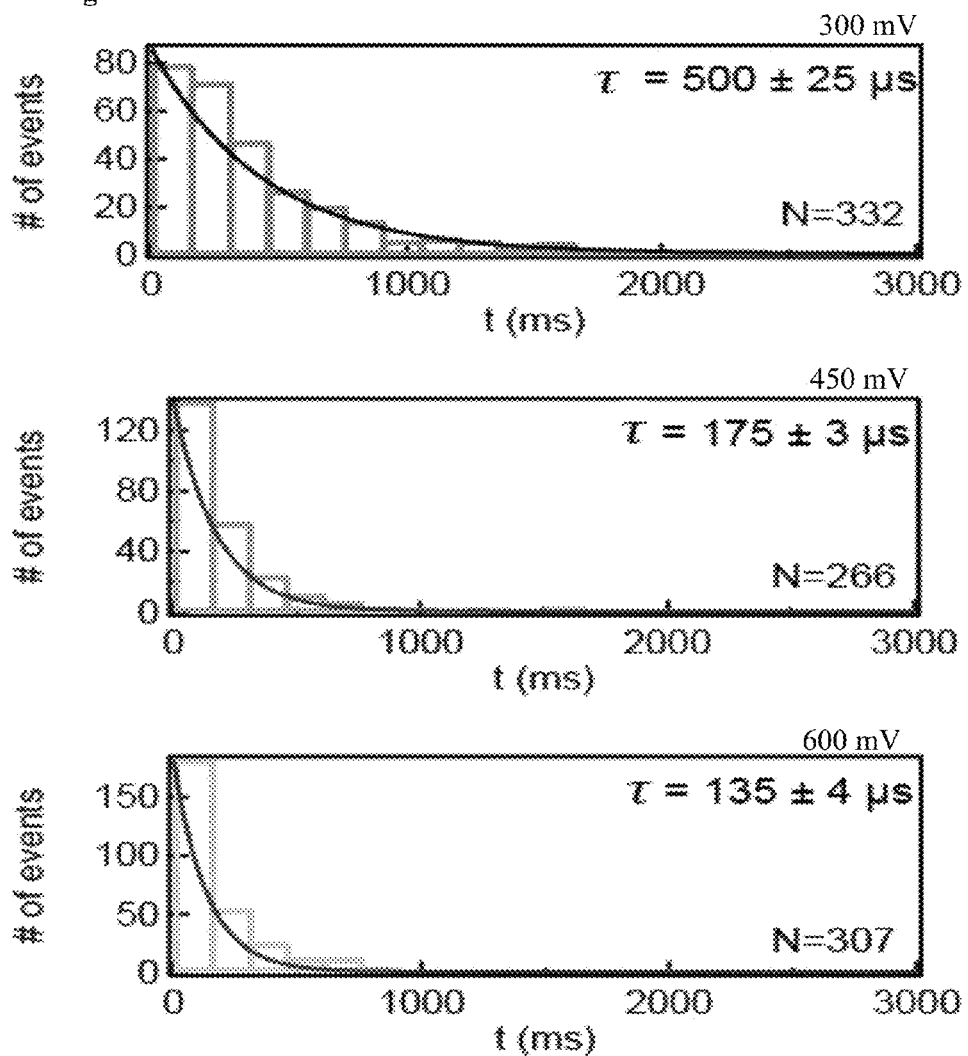
Figure 5H:
Figure 5H:
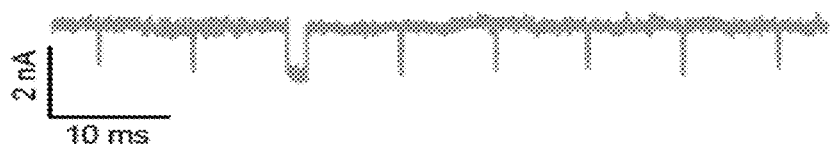
Figure 5H:
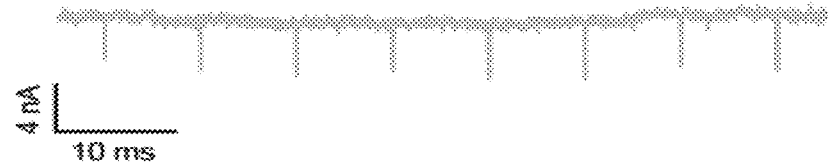
Figure 5I:
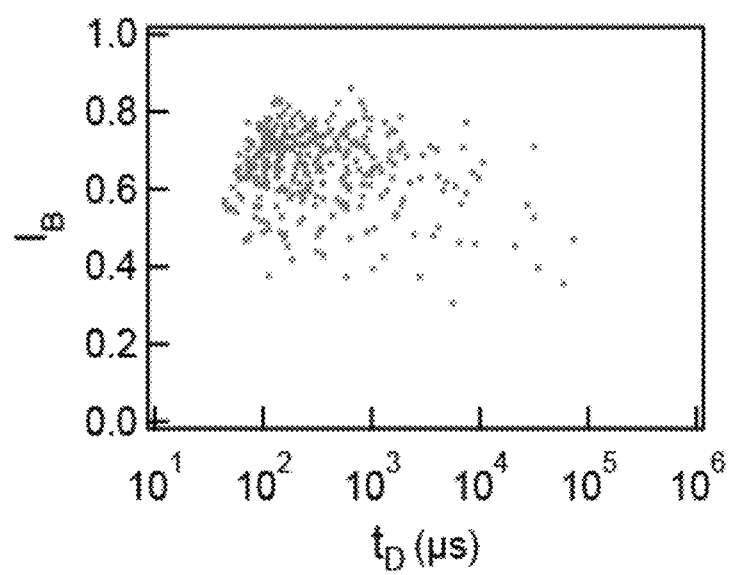
Figure 5J:
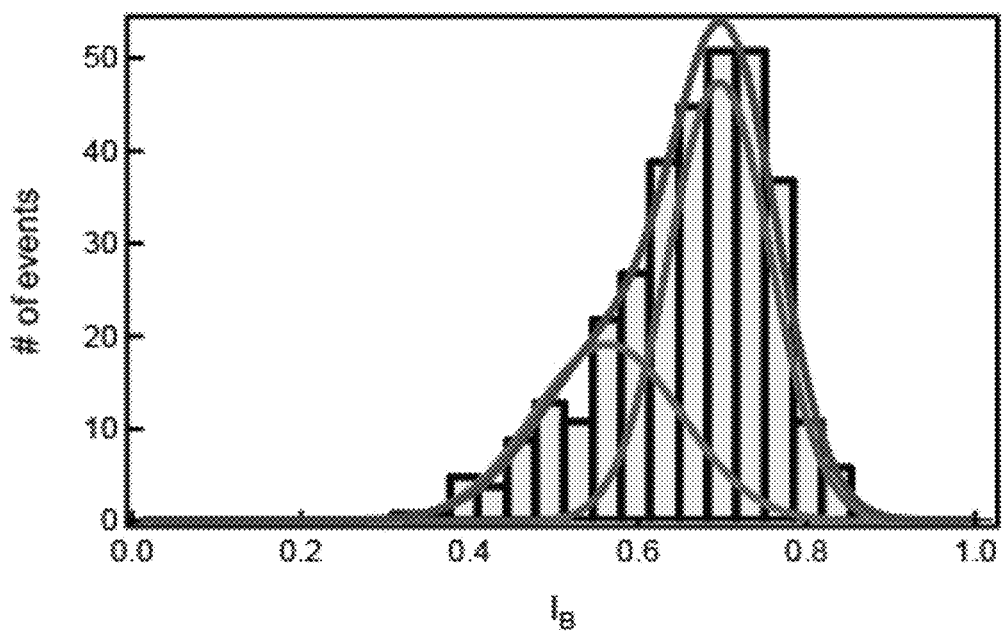
Figure 5K:
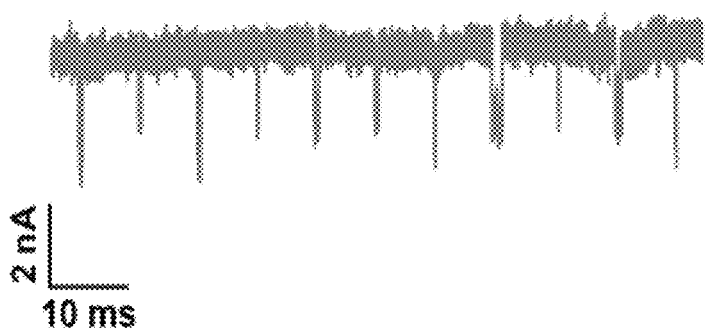

Finally, we validated the functionality of laser-etched nanopores by performing extensive sets of DNA and proteins translocation experiments. First, we added 300 pM 5054 bp dsDNA, produced and purified in house, to the cis chamber filled with KCl buffer. Upon biasing the trans chamber at +300 mV, the initially stable open pore was interrupted by current blockage events of 1.4-2.2 nA or 0.42-0.62 of the open pore current (FIG. 5D-E). For a pore of this small size (3.2±0.3 nm), we can expect a significant fraction of events to be collisions, as has been established by both theory and experiment. Therefore, to determine whether there are any full translocations, we performed an additional two translocation experiments at 450 and 650 mV and compared the dwell times of the three experiments. As can be seen in FIG. 5F-H, there is an obvious decrease in average dwell time with increasing voltage, indicating that a distinct portion of the events are successful translocations and not collisions. In a subsequent experiment using another pore, the Gaussian fitting clearly delineates two populations corresponding to two event types: short and low blockage/shallow events representing translocations, and long and high blockage/deep events representing collisions (FIG. 5I-K). The short and shallow events, though fewer in number, appear at the expected ratio relative to the long and deep events assuming that the DNA polymer behaves the same as it does with TEM-drilled nanopores. Nevertheless, both nanopores studied generated sufficient events to produce a statistically reliable result.

Figure 5L:
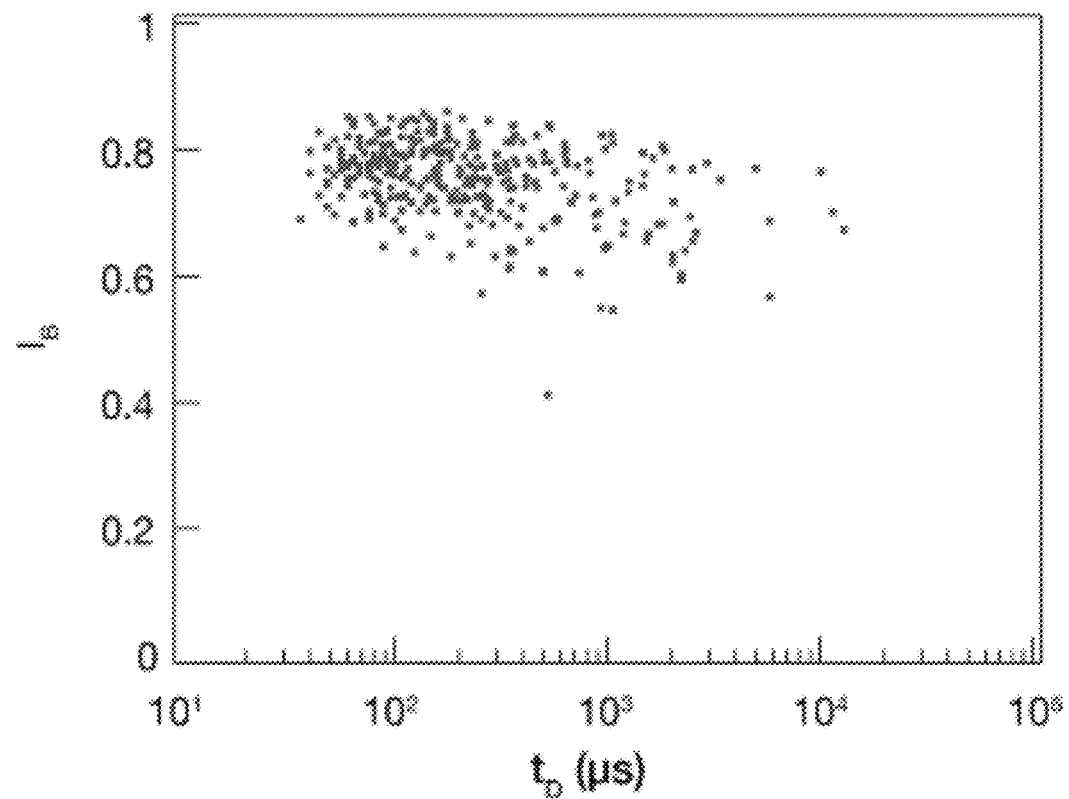
Figure 5M:
Figure 5N:
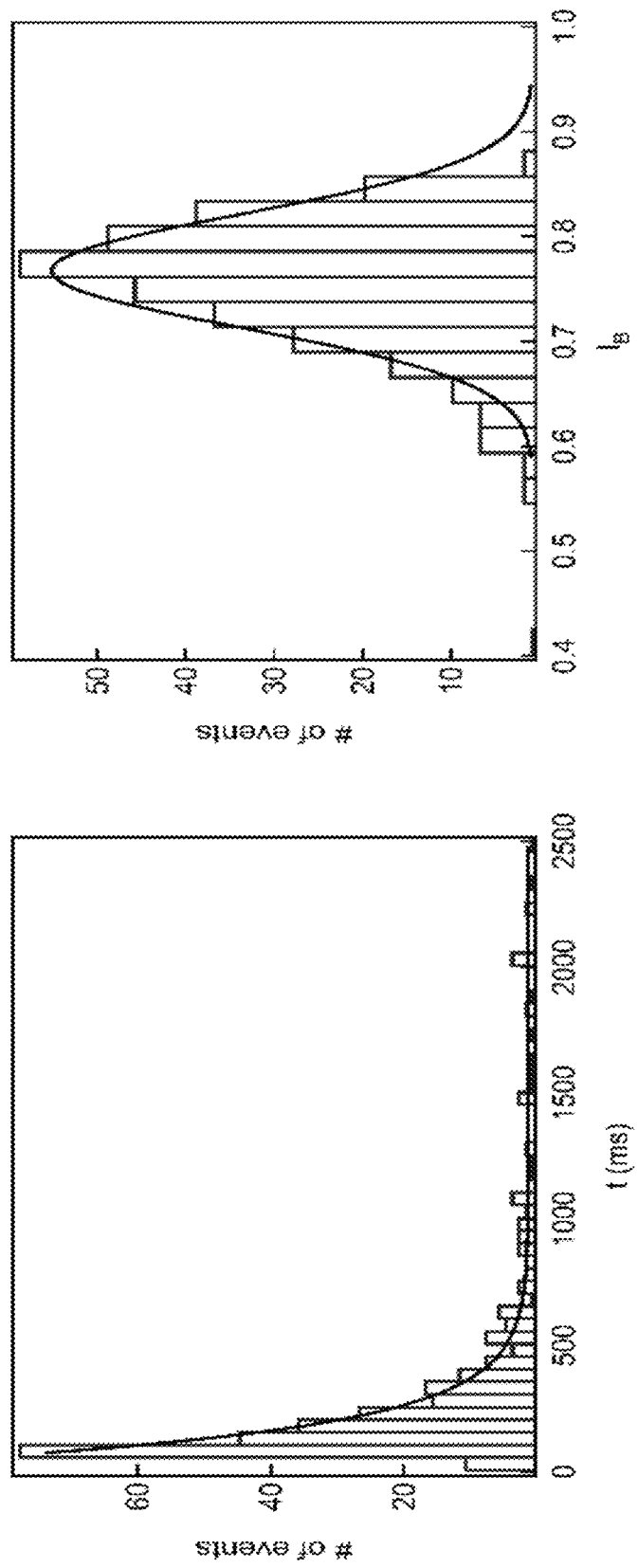

We further challenged our nanopore fabrication method to the purpose of detecting one of the smallest protein molecules (K63-linked di-ubiquitin, ~17 kDa), which compared to DNA, poses exceptional spatial and temporal resolution requirements. As has been demonstrated with TEM-drilled pores, one way to reduce the protein translocation rate is to use a buffer pH close to the isoelectric point (pI) of the protein. Therefore, for di-ubiquitin (di-Ub) with a pI of 6.7, we adjusted the KCl buffer to an experimentally determined pH value of 7. Using a nanopore with an OPC of 7-7.2 nA, we observed shallow (0.2 of the OPC) and mainly short (40-200 μs) events upon the addition of di-Ub to the cis chamber (FIG. 5L-N), expected for this pH value. This set of experiments proves that these nanopores are suitable not just for DNA studies but also small and compact proteins such as di-Ub. Moreover, we note that many of the ssNPs used for translocation experiments were over 10 days old—kept dry in air and made hydrophilic prior to the experiment—attesting to the high stability of laser-etched nanopores.

Example 3: The $SiN_x$ Membrane Etching Rate Strongly Depends on the Si:N Ratio

We have shown direct, in-situ laser-based membrane-thinning and fabrication of ssNPs in the range of just a few nanometers in freestanding silicon nitride ($SiN_x$) membranes (x=0.75 for stoichiometric $Si_3N_4$; wherein just a mW-intensity laser and a confocal microscope was necessary for nanopore fabrication at any arbitrary position and in any quantity. However, the physical process governing laser-drilling in thin, water-immersed membranes, particularly in the absence of any dielectric breakdown application, remains obscure. Specifically, the relative contributions of direct heating versus polarization of the thin membrane by the laser light, remain unclear.

Amorphous $SiN_x$ films are typically produced using a chemical vapor deposition (CVD) process, tuned to form silicon-rich membranes with respect to stoichiometric $Si_3N_4$, resulting in low-stress thin films. The Si:N ratio (denoted x) only slightly alters the material's refractive index, but it greatly affects the abundance of the Si dangling bonds, and in turn the photoluminescence (PL) spectrum produced by the film, as the latter involves photo-activated electron excitation and relaxation. We hypothesized that materials composed of slightly different Si:N ratios would result in dramatically altered laser drilling characteristics. To check this hypothesis, we systematically fabricated a series of $SiN_x$ films with different Si:N ratios. We characterized the material properties for each batch, including the Si:N composition and energy bandgaps using electron energy-loss spectroscopy (EELS) and energy-dispersive X-ray spectroscopy (EDS), and studied the laser drilling mechanism under various excitation wavelengths and solution pH. Our results point to a highly Si:N composition- and pH-dependent mechanism that is clearly photo-activated. Importantly, we show that at high Si:N ratios and alkaline conditions, we can drill functional nanopores in <10 s at laser excitation powers that are roughly an order of magnitude smaller than those employed in previous reports. This enables controlled in-situ laser fabrication of nanopore arrays with arbitrary patterns within minutes.

Material composition analysis is not routinely performed as part of the LPCVD process because it involves delicate elemental spectroscopy. Instead, the material's index of refraction is often used as a proxy for the Si:N composition, in which a higher index of refraction corresponds to a higher content of Si over N in $SiN_x$ membranes. Notably, however, small changes in the index of refraction correspond to significantly different Si:N compositions, preventing fine control of the Si:N ratio, and resulting in significant batch-to-batch variation. While these variations may be too small to affect e-beam or ion-beam nanopore drilling methods, we readily detect their effect on laser-based drilling as reported here. We produced four wafer batches using the same LPCVD instrument which had slightly different Si:N compositions, characterized by their indices of refraction (2.15, 2.20, 2.29, and 2.42, as measured by an ellipsometer). To monitor the $SiN_x$ membrane thinning prior to pore creation, we used a custom-made confocal microscope equipped with multiple laser excitation lines and two spectrally-resolved emission channels coupled to two avalanche photodiodes (APDs; see FIG. 7A and Materials and Methods). After positioning the membrane at the focus of the laser spot, we measured the PL intensity time-trace during laser irradiation. We typically observed a fast PL intensity reduction followed by a slower decay associated with the gradual decrease in membrane thickness and the formation of a Gaussian-shaped etch profile. The ion current and PL were simultaneously monitored during laser irradiation, and pore formation was signaled by an abrupt jump in the ion current. We also inspected each nanochip before and after the laser process under white light illumination to locate visible thinning of the membrane (see Materials and Methods).

Figures 7B, 7C:
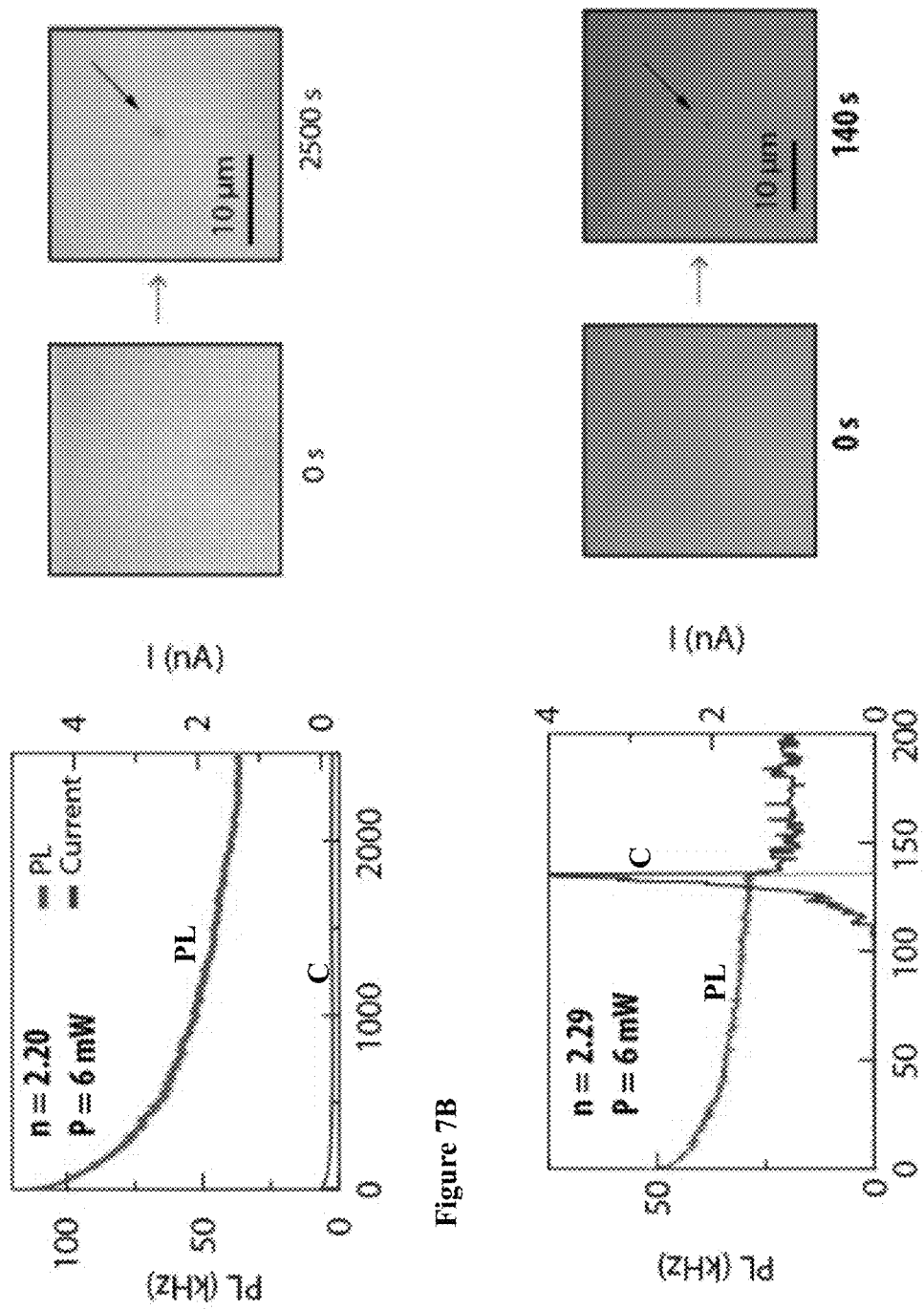
Figure 7D:
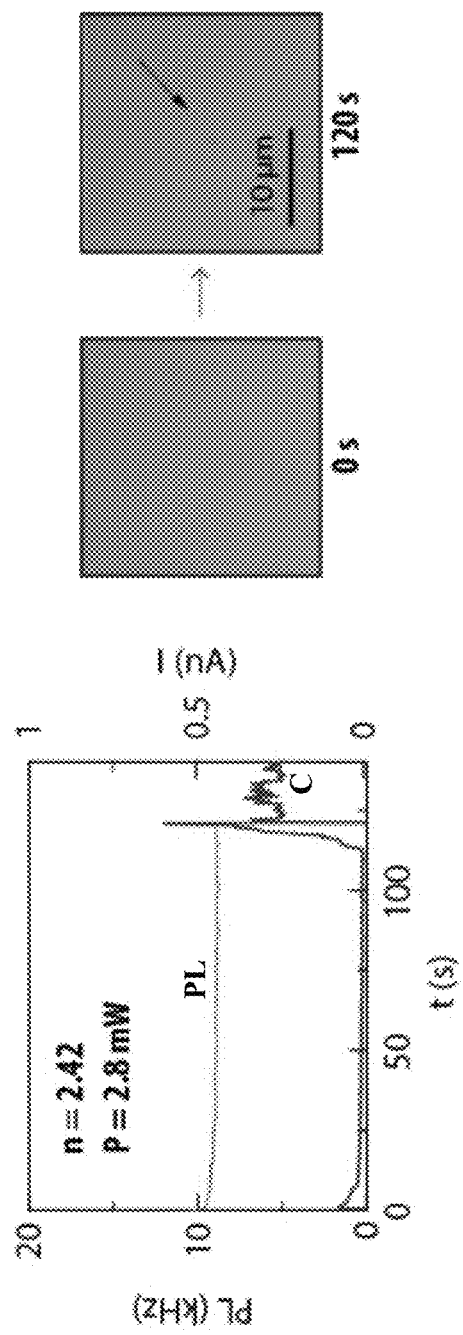

We first compare the membrane thinning and NP drilling kinetics of two 45 nm thick $SiN_x$ membranes (488 nm, 6 mW measured at sample plane) having slightly different indices of refraction (n=2.20 and n=2.29, FIGS. 7B and 7C). Although the difference in the reflectivity of the different batches (calculated as $R=(n_s-n_w)^2/(n_s+n_w)^2$ where $n_s$ and $n_w$ are the $SiN_x$ and water indices, respectively) is less than 2%, they were affected differently by laser irradiation: the membrane with the higher index of refraction formed a thinned area and a pore through the 45 nm thick membrane within 2 minutes, while the membrane with a slightly lower index of refraction did not form a pore even after >40 minutes of continuous irradiation, and displayed significantly higher initial PL. Inspecting these chips under white light illumination (right-hand experiments were performed at pH 7 in high salt (Tris-HCl buffer, 1 M KCl) and reproduced many times (N>100 times).

Figure 7E:
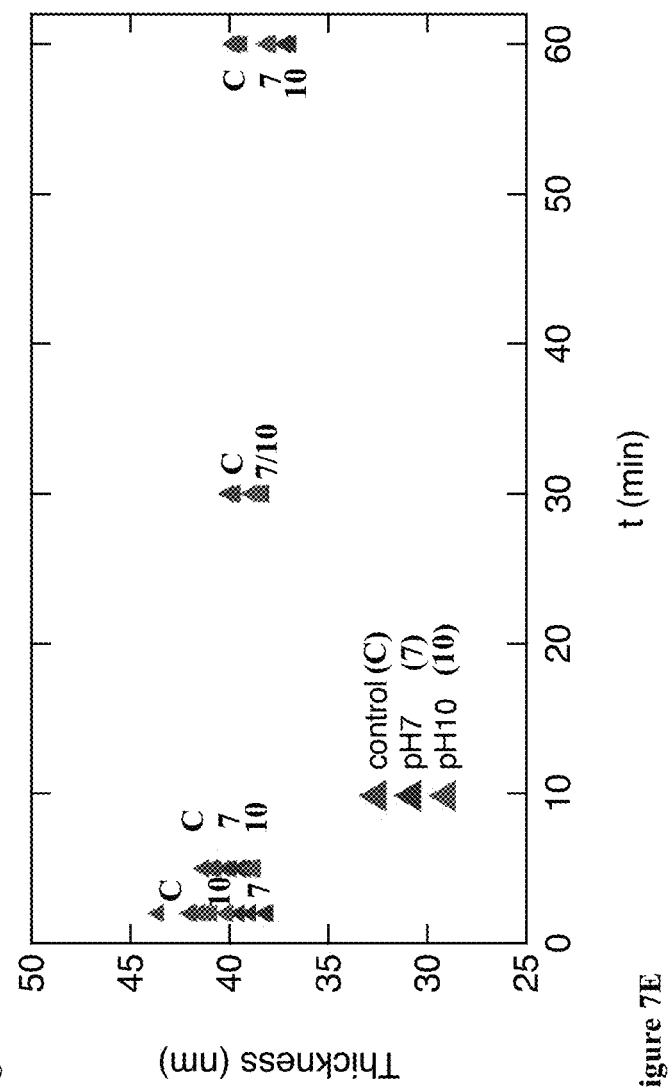

The striking difference in the thinning and drilling time between the two chip types, which only differed slightly in their Si:N compositions, prompted us to hypothesize that the nanopore drilling process is photo-activated. Attempts to thermally induce membrane etching by suspending the membranes in the same buffer (Tris-HCl pH 7, 1 M KCl) at 90° C. for over 60 minutes produced negligible or no etching at all of either $SiN_x$ membranes as measured by ellipsometry (FIG. 7E). This may suggest that the drilling process requires an electronic transition in the Si-rich membranes, which cannot be provided by heating alone. Indeed, nanochips with an even higher index of refraction (n=2.42) could be drilled in less than two minutes at even lower excitation laser power (2.8 mW, FIG. 7D). Attempting to drill the n=2.42 chips at 6 mW laser power resulted in near instantaneous (less than a second) formation of a large pore, which was hard to control.

Figure 8A:
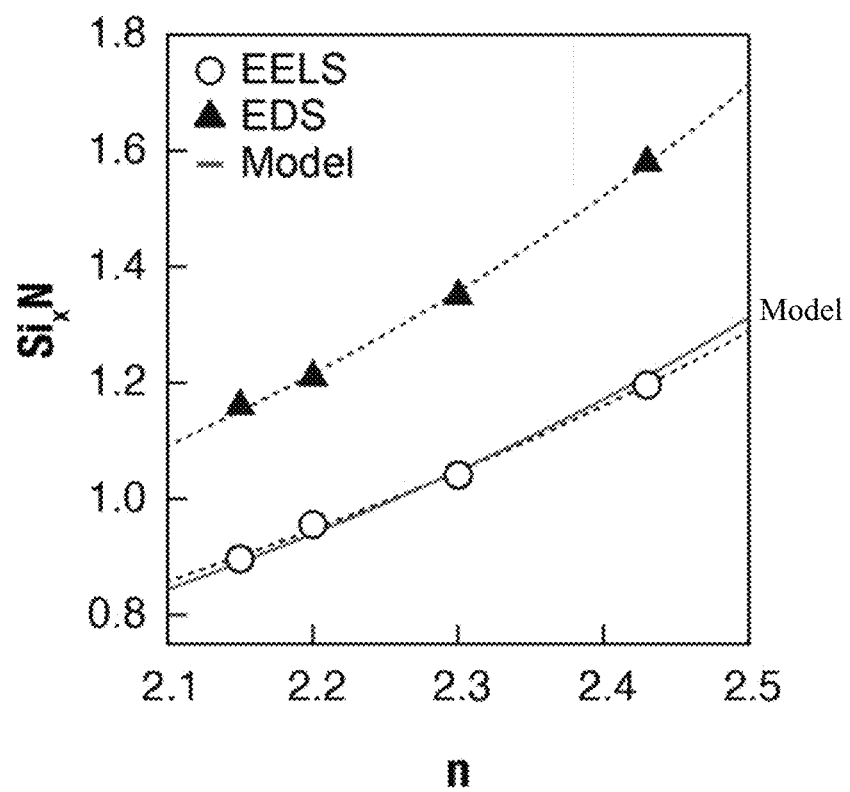
Figure 8B:
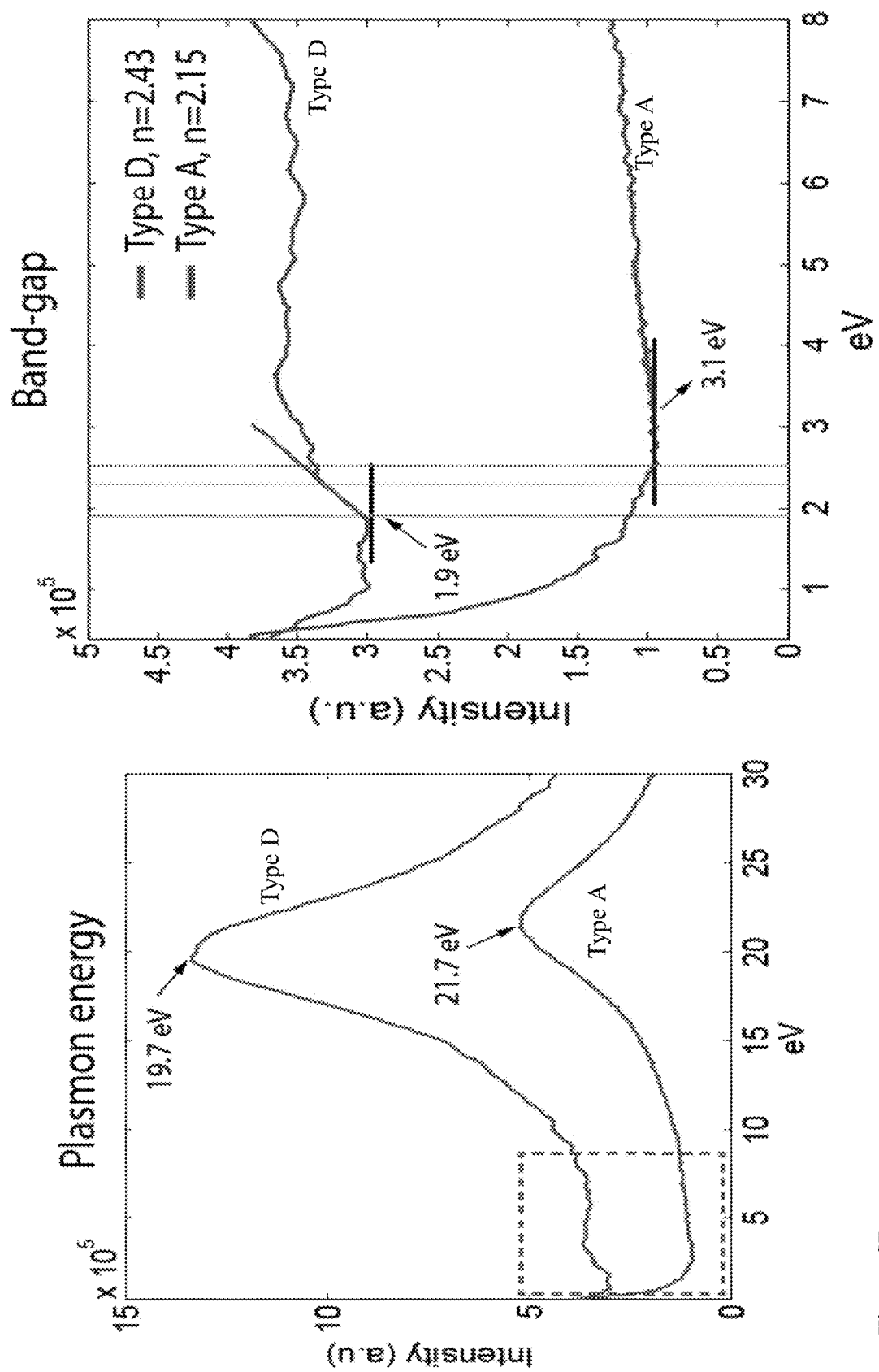

In order to establish the relationship between the $SiN_x$ membrane indices of refraction and the Si:N composition, we analyzed the materials using both electron energy loss spectroscopy (EELS) and energy dispersive x-ray spectroscopy (EDS) (see Materials and Methods). Each chip was cleaned using argon plasma before measuring the EELS or EDS spectrum. We employed dual EELS measurements to obtain both low loss and core loss data, in order to estimate both the material thickness (using the low loss spectrum) and the material composition (using the core loss spectrum). The atomic percentage of each material was also measured at the same position using EDS. The thickness estimation indicated similar thicknesses for all tested chips in the range of 44-46 nm. While systematic differences between EELS and EDS in measuring the Si:N ratio are expected based on previous literature, our results (FIG. 8A) show a consistent trend and agree very well with a previously employed empirical model (red solid lines) predicting that:

$$Si:N = \frac{3n + 3n_\infty - 6n_{3/4}}{4n_\infty - 4n}.$$

Where $n_\infty$ is the refractive index of pure Si and $n_{3/4}$ is the refractive index of $Si_3N_4$ (reported theoretical values are $n_\infty=3.86$, $n_{3/4}=1.99$). Fitting each of the measurements with the model resulted in the following parameter values: $n_\infty=3.995$, $n_{3/4}=1.964$ for the EELS and $n_\infty=3.683$, $n_{3/4}=1.740$ for the EDS (dashed lines). These measurements indicate that on average, the atomic Si:N ratio ranges from about 0.9 to 1.5 for the range of indices from 2.15 to 2.42 respectively, representing significantly larger Si content as compared to the stoichiometric value of $Si_3N_4$ (0.75). EELS-based band gap measurements of the chips with refractive indexes of 2.15 and 2.42 showed, as described before, that higher refractive index results in a smaller band gap (FIG. 8B). Using the lower band gap Si-rich chips we were able to drill nanopores using a green (532 nm) laser with intensity of 5 mW in less than 2 minutes (FIG. 8C).

Figure 8C:
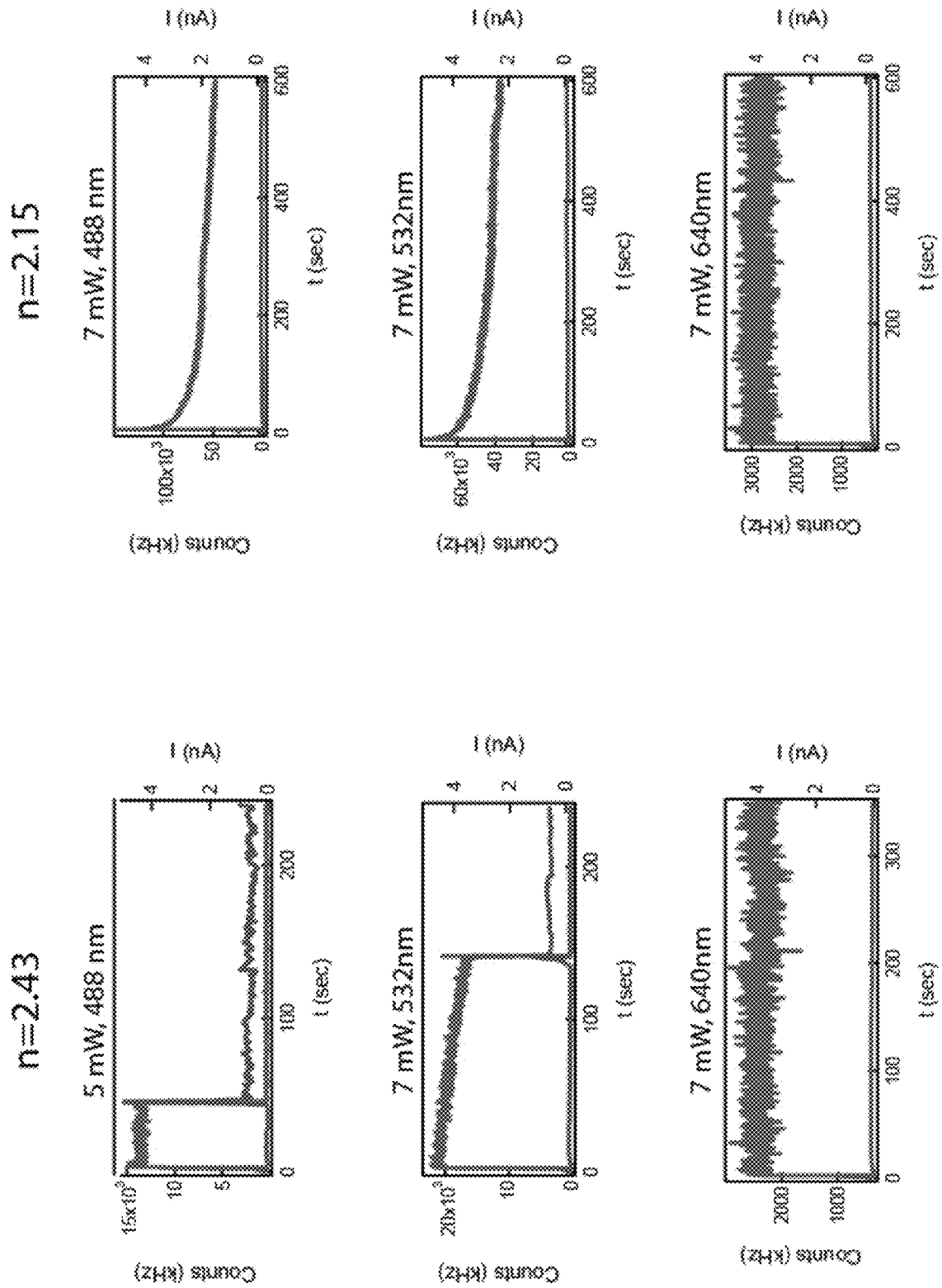

Specifically, in FIG. 8C we compare the drilling characteristics of a chips with different refractive indices (n=2.3 and n=2.43) using three laser wavelengths (488 nm, 532 nm and 640 nm). Each chip was immersed in 1 M KCl pH 7 solution and was exposed to a focused laser beam of the specified wavelengths and intensities. The current and the PL were measured until a pore was formed or up to 10 minutes. As can be seen in FIG. 8C, the high refractive index chip was easily drilled with the 488 nm laser (in this case the laser power was decreased since higher power resulted in immediate current overload) as well as the 532 nm laser, while the low refractive index chip could not be drilled with any of the three wavelengths.

Figure 8D:
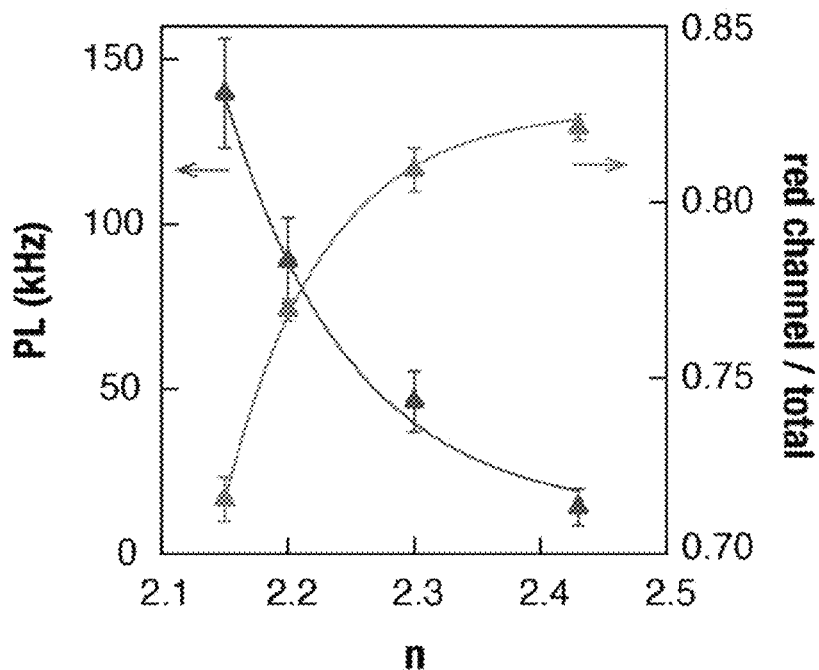

The fact that Si-rich membranes were much more readily drilled using focused light prompted us to further study their optical properties. We focused our attention on the PL emission of the membranes, as this phenomenon is strictly related to photon absorption and photon emission associated with electron excitation/relaxation (unlike scattering). To avoid inducing any material etching, we reduced the laser power by three orders of magnitude to ~7 µW and measured the PL emission in two spectrally-defined emission bands (550 nm<Ch1<650 nm, Ch2>650 nm; see Methods). In FIG. 8D we show the total PL emission (dark grey markers and line) measured for these samples, as well as the ratio of the red-band emission over the total emission (light grey markers and line). Our results show significantly lower apparent PL intensities for the higher $SiN_x$ indices of refraction: Changing the index of refraction from 2.15 to 2.42 resulted in roughly 7-fold PL reduction in the measured visible band. This result initially appeared to be counterintuitive; the $SiN_x$ membrane band-gap energy slightly decreases with increasing Si content, which should allow more efficient electron excitation from the valance to conduction bands prior to their relaxation and the emission of a red-shifted PL. However, as the material becomes successively more Si-rich, the density of the Si dangling bonds is known to increase, providing additional energy relaxation pathways involving lower energy photon emissions. Indeed, we observe a systematic red-shifting of the PL at the higher Si:N ratio (FIG. 8D, light grey curve). Noticeably, the lower energy photons associated with these transitions are expected to be outside of the photon counter measurement band. Consequently, these processes would substantially reduce the apparent PL measured in the visible emission band.

Example 4: $SiN_x$ Membrane Etching is Accelerated Under Alkaline Conditions

The strong dependency of the $SiN_x$ thinning and nanopore drilling on the Si:N composition suggests that the etching mechanism involves a photochemical reaction. At low irradiation intensities, and specifically for Si-rich material, the laser-induced temperature rise in the water-submersed thin-film appears to be less critical than electronic excitation. In this regime, the enhancement in etch rate can be related to the generation of electron—hole pairs within the $SiN_x$ surface and charge transfer at the liquid—solid interface. At the water interface, the dissolution rate of a silica-like material is expected to be strongly affected by pH since the hydroxyl ion is a catalyst for the hydrolysis that underlies the dissolution process. We therefore hypothesized that the etch rate and subsequent pore formation rates could be further accelerated under alkaline conditions.

To investigate this possibility, we performed a set of experiments to measure the membrane etching rate and pore formation as a function of pH, under different laser irradiation intensities. We performed two complimentary measurements: (1) using white-light microscopy we measured the membrane thinning rate by comparing the transmitted light intensity before and after irradiation of a laser for a fixed length of time. (2) Additionally, we used the PL intensity as a proxy for the etching process and characterized its kinetics (FIG. 9). Our results show a clear and consistent trend: Under acidic pH, the thinning process is slowed down significantly, as evidenced by nearly imperceptible changes in the transmitted light intensity. In fact, only under strong laser intensity could we visually discern thinning at all. The PL kinetics measurements were only weakly dependent on the laser intensity at this pH. In contrast, under alkaline conditions (i.e. pH 10 or 12) the drilling process is highly accelerated. Specifically, we observe membrane thinning even at extremely low laser power irradiation down to just a few mW and the PL kinetics show strong dependency on the laser power.

To quantify the thinning rate under different conditions, we irradiated the same chip for a fixed length of time at different laser intensities. Then we switched buffers as indicated (see Materials and Methods), and the measurements were repeated several times. In FIG. 10A we show typical results of the white light image (100× magnification) at 4 pH values, measured using the same laser intensity. We can clearly observe increased thinning under alkaline conditions (pH 10-12) and little to no thinning at pH 4. To quantify the result, we show in FIG. 10B the normalized intensity changes as a function of laser power, measured at t=120 s. Our results can be approximated by a linear dependence on the laser power. From the slopes of the curve we obtain the following ratios for pH 7, 10 and 12 as compared with the pH 4 slope: 2.3±0.24, 8.46±0.6, and 10±0.61 mW$^{-1}$, respectively. These results indicate that thinning can occur at high pH, even at low laser power. In addition, high pH buffer allows fast initiation of the thinning process, which could provide excellent conditions to drill nanopores at high speed (FIG. 9).

To confirm that the pH dependence measurements are not biased by different buffer indices, we measured them using a refractometer (Rudolph, J257). The measurements were performed at similar temperature to the thinning experiment (22° C.). The results in Table 2 show similar values for all solutions, indicating that the buffer did not play a role in the PL measurements.

Example 5: Ultra-Fast Nanopore Drilling in Si-Rich Membranes

Figures 11A, 11B:
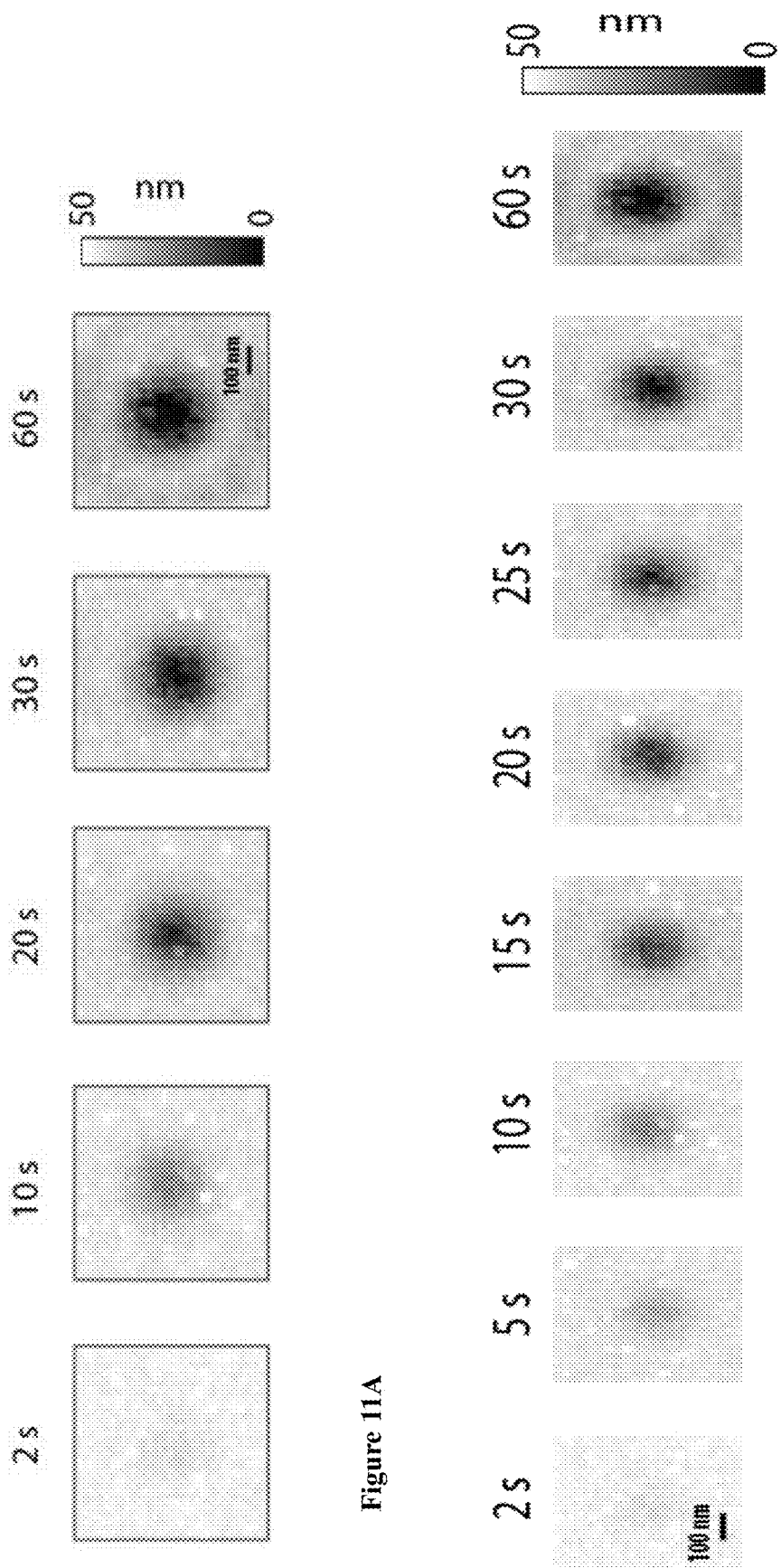
Figure 11C:
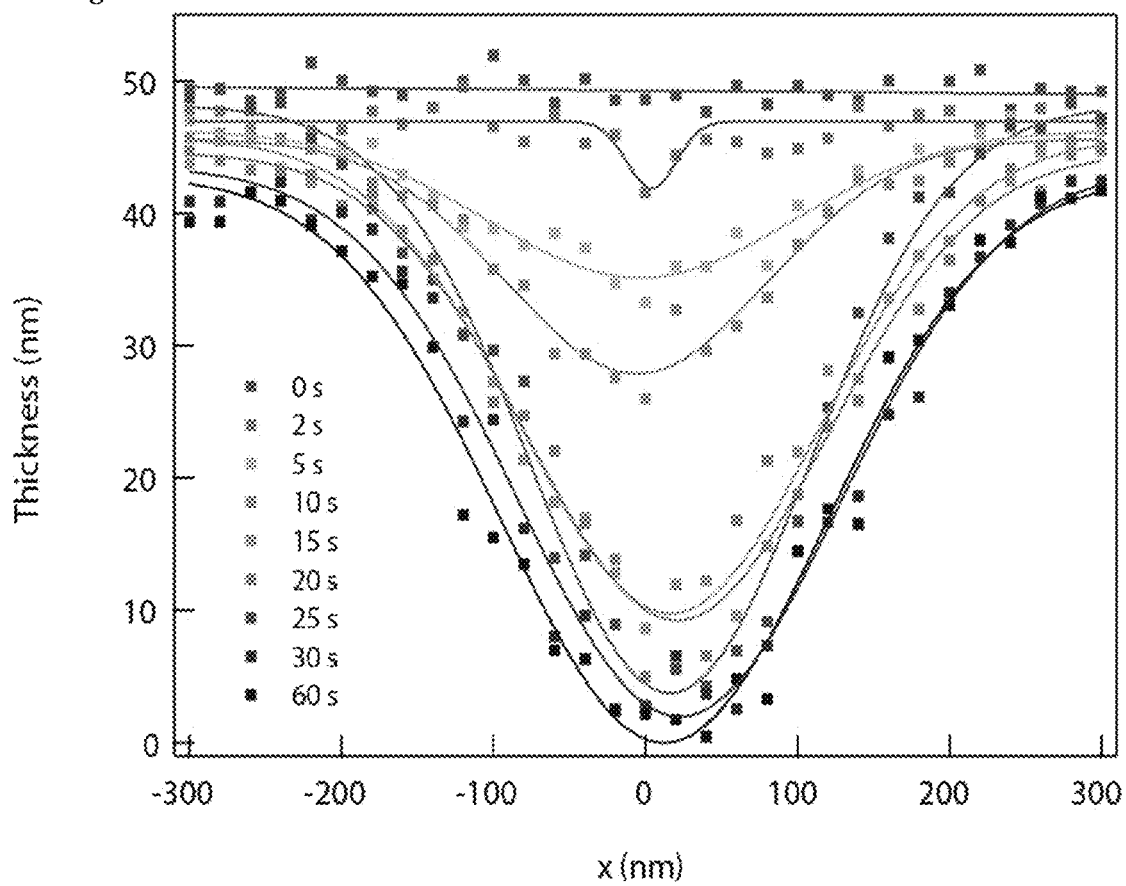
Figure 11D:
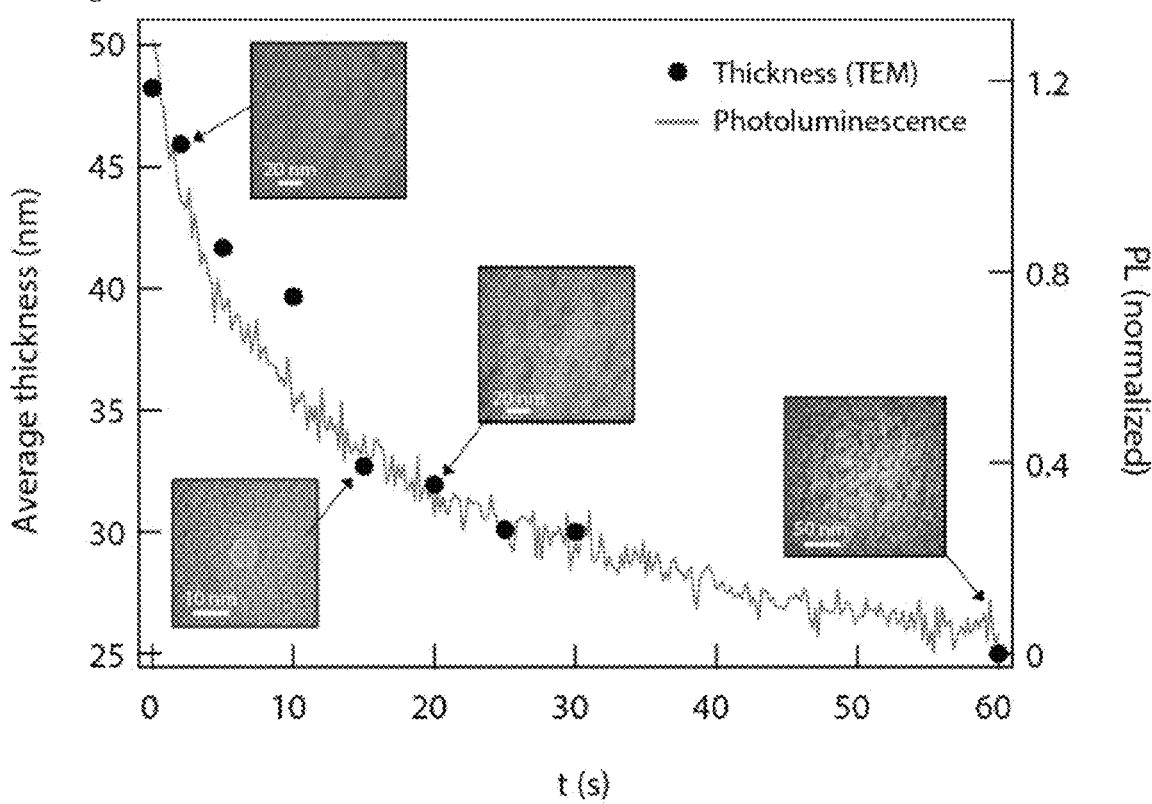

The strong dependency of thinning on pH and material composition encouraged us to further analyze and characterize this process in order to achieve controlled, ultra-fast, nanopore drilling at low laser intensities. We first immersed a chip with refractive index of 2.3 in high pH buffer (pH 10), exposed it to a 488 nm laser of 7 mW for varying durations, and created a thickness map of the exposed region using EELS. As expected, the thickness maps presented in FIG. 11A show that longer illumination results in increased thinning. This is further demonstrated by comparing the line scans in the middle of each thinned region (FIG. 11B-C). Integrating over this line scan shows a similar trend to the PL measurement during thinning, indicating that the PL can be used to approximate changes in thickness and membrane composition (FIG. 11D). High magnification TEM images revealed that an exposure of ~15 seconds was enough to create a ~5 nm pore in the center of the Gaussian shaped thin region (see left inset in FIG. 11D). However, further irradiation of the surface under these conditions resulted in multiple pores, as can be seen at ~20 s or at longer time points. An OPC gradient threshold (e.g. 0.65 nA over 100 ms) should be set to automatically shut off the laser at the onset of nanopore formation to minimize the likelihood of multiple pores, as was done for fabricating a nanopore array (FIG. 13A-C).

A drilling trace using a similar chip (refractive index of 2.3), pH 10 buffer, and 488 nm laser with intensity of 6 mW in which pore formation was detected electrically in less than 15 seconds is presented in FIG. 12A. To check the nanopore functionality, we immediately changed the buffer to a pH 7 buffer, added DNA sample (300 bp) and measured translocations (FIG. 12A-B). The pore diameter and effective thickness were calculated according to the average fractional blockage level (0.81±0.01) and conductance (19.1 nS). The calculated results suggest that the pore diameter is 5±0.4 nm with an effective thickness of 5±1 nm. A scatter plot of the dsDNA translocation events and concatenated ionic current trace showing sample translocation events are presented in FIG. 12A-B.

Having used a continuous-wave laser to this point, the ability of a pulsed laser to drill a high refractive index SiNx chip was tested. A pulsed laser source, specifically a picosecond laser (PicoQuant LDH series), was used to shine blue and green pulsed laser light on a membrane as described hereinabove (10-50 nm thickness). Pulse widths in the range 50 ps to 150 ps, with a repetition rate of up to 80 MHz were tested. The pulsed laser was coupled to the system using a single-mode optical fiber and focused on the sample using high numerical aperture water immersion objective (NA=1.15). The pulsed laser successfully drilled nanopores with an average intensity (power) of 5 mW or less. In comparison, at the same intensity and similar wavelengths a continues-wave laser took a longer time to drill. In circumstances where the continuous-wave laser resulted in no drilling after 10-20 minutes (i.e. higher wavelengths, lower refractive index) the pulsed laser was still able to produce thinning of the membrane. This demonstrates the superiority of the pulsed laser of the continuous-wave laser for thinning and drilling.

Example 6: An Automated In-Situ Fabrication of Nanopore Arrays Using Direct Laser Etching The ability to quickly form arrays of nanopores placed at any chosen locations is extremely important for future use of nanopores in high-throughput applications including nucleic-acid sequencing and protein identification. Both the means to electrically address each individual nanopore in an array, as well as parallel optical sensing, have been proposed and developed. Taking advantage of the ultra-fast, in situ drilling process presented hereinabove, we developed a simple hardware-controlled system for drilling an arbitrary array of pores. Specifically, drilling was automated by inputting a list of coordinates and a current gradient threshold. After focusing the laser on the membrane at low intensity, 150 mV was applied across the membrane, and the PL and current were measured in real time. After focusing, the piezo stage moved the membrane to the first coordinates, and the laser intensity was increased to 7 mW. Once the change in current increased above the current gradient threshold the laser was switched off and the piezo stage moved to the next coordinates (FIG. 13A, top), where the laser was switched on again. In this way the drilling process could stop immediately when a predetermined increase in current was detected (FIG. 13A, bottom).

FIGS. 13A-B display an example of an array of 25 nanopores drilled in ~6.5 minutes. The top panel in FIG. 13A displays time traces of the laser intensity. The PL and current are shown in the bottom panel (red and blue lines, respectively). As can be seen, all pores formed in less than 20 s, where small variations in the drilling time are mainly due to changes in the laser focus. Histograms of the drilling time and the change in the total current for each drilled pore are presented in FIG. 13B. The nanopore array was inspected by wide-field fluorescence microscopy using $Ca^{2+}$-activated fluorophores. Upon applying a +300 mV bias, 24 out of 25 fluorescent spots appeared at the expected nanopore locations as $Ca^{2+}$ ions were drawn through the nanopores and reacted with the $Ca^{2+}$ indicator dye (FIG. 13C, middle panel). The fluorescent spots disappeared when the opposite voltage bias was applied (FIG. 13C, left panel). To estimate the variation in pore sizes, we integrated the fluorescence intensities of each spot. A histogram of the result is shown in FIG. 13C (right) and is well-fit by a Gaussian distribution.

It has been reported that atomic layer deposition (ALD)-deposited titanium dioxide ($TiO_2$) thin membranes produce an extremely low photoluminescence and hence can be used favorably for electro-optical sensing of labelled DNA and proteins. We found that an ALD-deposited $TiO_2$ thin membrane is not appreciably etched even at high laser power (>45 mw using either red, blue, or green lasers) given its very low photon absorption in this range. However, coupling a $TiO_2$ layer to a high index refraction (>ND 2.2) layer such as $SiN_x$ enables etching at neutral and high pH (>7), similar to the etch behavior exhibited by free-standing $SiN_x$. In FIG. 14A (middle panel), the etching that occurs in a $TiO_2$ membrane on top of a $SiN_x$ membrane is depicted. This method can be used to fabricate nanopores directly in $TiO_2$. As can also be seen in FIG. 14A, the shape of the etch produced in the membrane is that of a Gaussian curve. This shape was observed when $SiN_x$ was thinned alone or with $TiO_2$. Further, the full width at half maximum of the Gaussian curve was found to always be one half of the wavelength of the laser light used to generate the nanopore, thus a given shape can be generated by selecting the wavelength of light used for the drilling.

In an alternative configuration a pH bias can be applied across the membrane surfaces (FIG. 14A, right panel), where the $TiO_2$ side is held at low pH and the $SiN_x$ is held at high pH, in order to prevent laser etching of $TiO_2$ and produce a free-standing $TiO_2$ membrane (FIG. 14B). Continued laser-etching (at a higher pH) of this free-standing $TiO_2$ membrane results in nanopore generation within the $TiO_2$ layer. The $TiO_2$ layer can be conveniently made ultrathin (<3 nm) by tuning the ALD deposition process, and generally photoluminescence monitoring allows for monitoring of local thinning in real time. This allows for distinct etching in distinct layers with different indexes of refraction.

Example 7: Characterizing Laser Etching Kinetics of Nanoscale Apertures

Before attempting to systematically manipulate and control the laser drilling (LD) process, we fabricated a custom sample that allows a thorough investigation of the laser-based etching kinetics. We hypothesized that as the full-width half maximum (FWHM) of a tightly focused laser beam is much larger than the typical ssNP diameter, if the etching process is allowed to proceed freely it would result in the formation of an aperture having a size roughly of the beam's point spread function (PSF), $\lambda/(2\ NA)$, where $\lambda$ is the laser wavelength and NA is the objective's numerical aperture. But if the laser etching is timely terminated, it would permit the formation of ssNPs much smaller than the PSF size, and with fine control over the process kinetics, it can be used to create nanopores with nanometer resolution.

To image the etching process using TEM, we fabricated a two-layer model substrate consisting of a 50 nm thick $SiN_x$ on which 10 nm $TiO_2$ layer was deposited by Atomic Layer Deposition (ALD). Previous studies revealed that the LD rate is extremely sensitive to the Si/N ratio in the free-standing $SiN_x$ film. Specifically, Nitride-rich membranes or stoichiometric $Si_3N_4$ were found to remain nearly intact even when irradiated with high intensities of blue laser, whereas Si-rich membranes could be readily etched at relatively low laser intensities, even when exposed for brief lengths of time. This phenomenon is attributed to the smaller bandgap of the Si-rich membranes, which permits efficient electron excitation of the membrane by visible light. Consistent with this result, we find that free-standing, high bandgap materials such as $TiO_2$ (3.0 eV for rutile and 3.2 eV for anatase), remain intact even after extremely long (>300 s) and high intensity (>30 mW) 488 nm laser irradiation focused to a diffraction limited spot. Therefore, the $TiO_2$ layer deposited on top of a the $SiN_x$ membrane may provide convenient means for analyzing the thinning progress using high-resolution TEM combined with nanoscopic elemental analysis in which silicon, nitrogen, titanium, and oxygen are easily distinguished.

FIG. 15A displays a TEM (FEI Titan Cubed Themis G2) image of the composite $SiN_x/TiO_2$ 50/10 nm membrane after illuminating the membrane with a focused 488 nm laser beam (18 mW measured before the objective lens, see FIG. 16A) for variable doses from 5 s to 60 s, as indicated. An additional dose (t=110 s) was performed as a long-time reference point, noting that longer exposures (roughly above 2 minutes) may not produce consistent results due to slow mechanical drift of the stage. We used high Si-content (n=2.42) material deposited by Low Pressure Chemical Vapor Deposition (LPCVD) and submerged in alkaline solution (pH 10) in this experiment. Based on previous studies these conditions are expected to result in nanopore formation in just a few seconds, should we use the bare $SiN_x$ membrane. We find, however, that the 10 nm $TiO_2$ layer prevents nanopore formation up to roughly 60 s of irradiation, while providing a strong contrast for imaging of the resulting nano-wells using high resolution TEM. The FWHM of the nano-wells as a function of the laser irradiation is shown in FIG. 15B. Interestingly, and in accordance with previous reports, we see that laser etching can form sub-PSF sized nano-wells, with a diameter that is linearly dependent on the laser exposure time, ranging from about 20 nm to 250 nm. Moreover, a closer examination of the nano-well intensity suggests that for doses smaller than about 35 s, the intensity appears to be brighter than at later times. To further evaluate this finding, we performed Energy Dispersive X-ray Spectroscopy (EDS) analysis of the nano-wells by integrating the signal from a fixed area centered around each of the spots. As summarized in FIG. 15C, Si and N atoms are depleted as time progresses, reaching a plateau at about 30 s. At the same time, and as expected, the content of Ti and O atoms rises in the first 30 s, reaching nearly 30% and 60% respectively for t>30 s.

The results shown in FIG. 15A-C demonstrate that during the laser etching process, the $TiO_2$ layer remained intact while the Si and N atoms were evacuated to the surrounding hydroxyl-rich aqueous solution. Interestingly, the process kinetics indicate that even after a short exposure, the $TiO_2$ layer becomes exposed with the formation of a sub-PSF nano-well: starting from a 5:1 ratio of $SiN_x/TiO_2$ based on the initial layer thicknesses, one can see a steep inversion in the elemental composition already at the 10 s time point. These results demonstrate the capability of a sub-micrometer optical beam to controllably form nanoscale wells. Evidently, a key to the process is maintaining the tightly and well-controlled laser focus at the membrane position and monitoring the process with a real-time algorithm. These are key features for the development of a deterministic LD method.

Example 8: Applying Real-Time Feedback Control for Deterministic LD of ssNPs

Figure 16A:
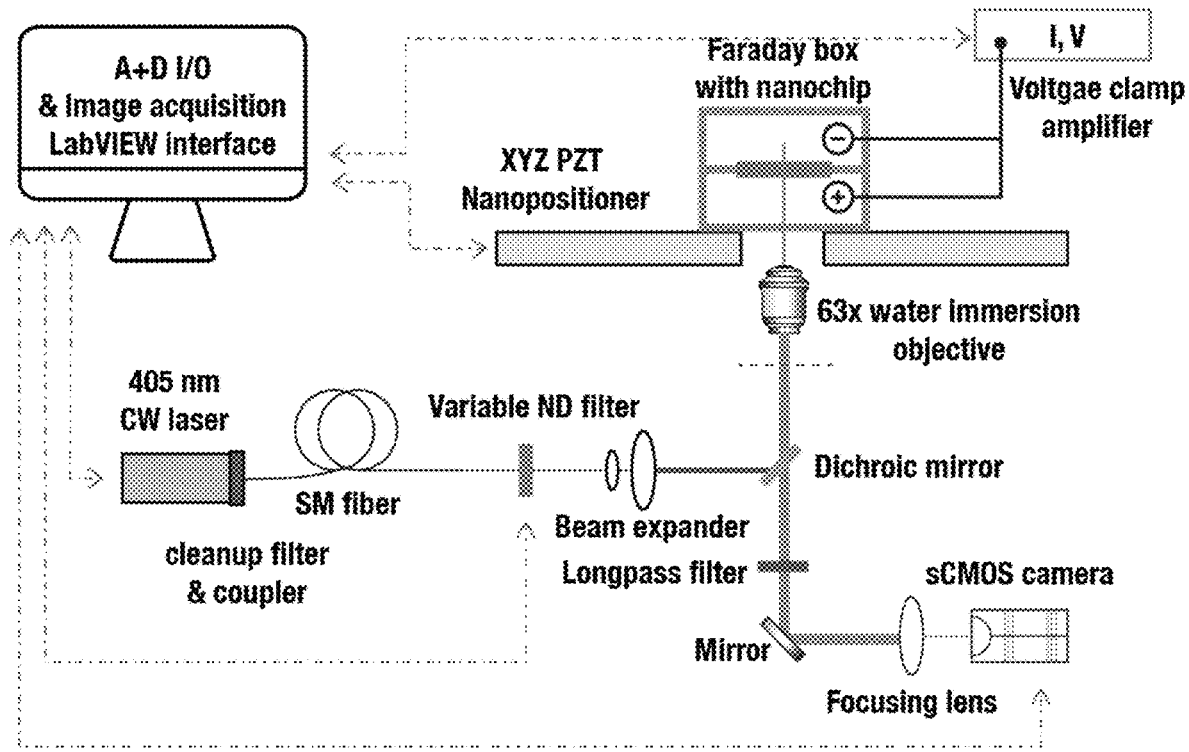
Figure 16B:
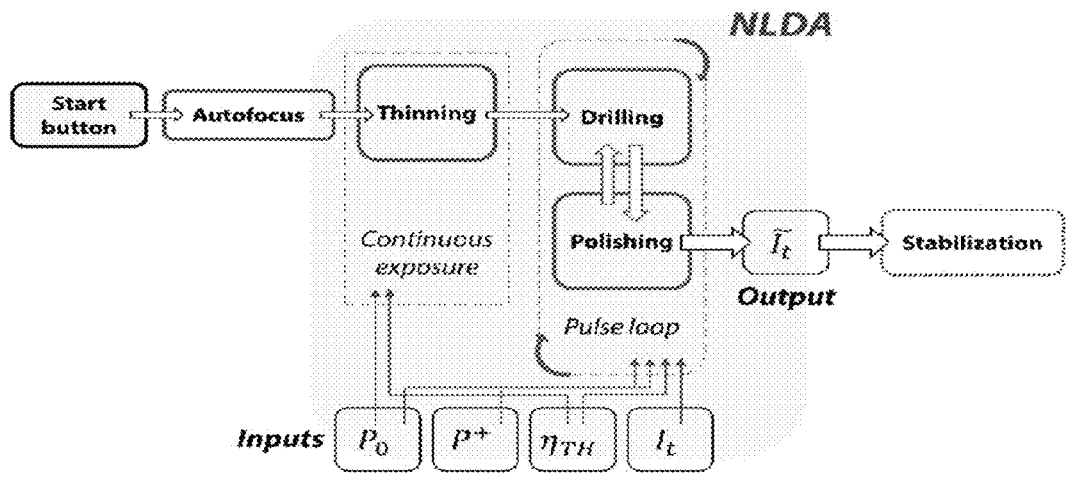
Figure 16C:
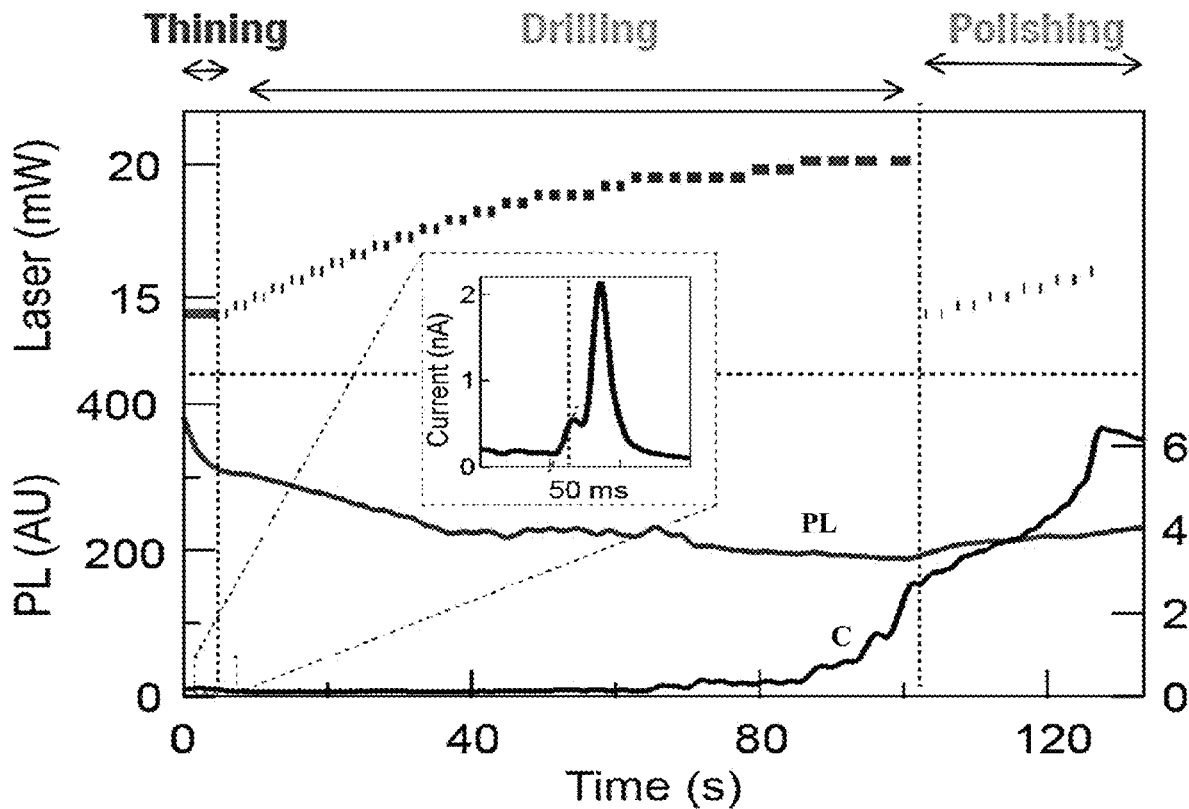

To facilitate the optical feedback process and permit precise autofocusing, we designed an opto-mechanical system and developed a computer program to control the entire LD process, as shown schematically in FIGS. 16A and 16B, respectively. The optical design includes a 405 nm CW laser coupled to a single mode polarization preserving fiber. The single-mode fiber is used as a spatial filter ensuring a clean $TEM_{00}$ mode, which is crucial for producing a diffraction limited Gaussian laser spot. Before entering the microscope, the beam is expanded using a telescope made by two achromatic lenses forming an effective 5× magnifying telescope, which ensures the microscope objective back aperture is filled. The beam intensity is software-controlled by a variable intensity module and an on/off digital port switch for millisecond-scale intensity adjustment. This feature proved to be essential to the algorithm developed here, increasing its ability to deal with different membrane structures, thickness variations, etc. In this study we used a 63×/1.15 NA water immersion objective with a long working distance to permit focusing with minimal stress on the bottom cover slide. The sample is mounted on an XYZ piezo nano-positioner for accurate placement of the sample in front of the objective lens. The emitted light from the sample is filtered using a long pass filter and is imaged using a scientific CMOS (sCMOS) camera. The camera is used to find and center the $SiN_x$ window using white light illumination; to automatically focus the beam prior to drilling; and to measure photoluminescence (PL) during drilling. The sCMOS has a large dynamic range, which by using image processing, allows one to compute the PL at various laser intensities. Accordingly, The PL is calculated by summing the 3-by-3 neighborhood of the brightest pixel in the frame.

It was found that precise focusing of the beam at the membrane plane is critical for successful and reproducible LD. A slight shift in the z of even less than 100 nm may inhibit the LD process. To that end we implemented a simple "search and find" focusing algorithm which converges within typically 10-15 s to the exact focus. FIG. 22 shows the main aspects of the autofocus process. First, the PL PSF is imaged and fitted by a Gaussian function to extract its amplitude and width. Then the software moves the stage along the z-axis in a stepwise manner converging to the optimal focus (within 50 nm resolution) by maximizing the intensity. We define a minimization parameter, δ, which corresponds to the normalized distance from the focus point, where the highest PL value is measured along the z-axis. Minimizing δ equalizes the initial conditions for the subsequent drilling process, thus keeping the process robust and effective.

FIG. 16B shows schematically the general flow of the LD process, which is controlled by the 'Nanopore Laser Drilling Algorithm' (NLDA), integrated into our software (see FIG. 23 for the graphical user interface). The core algorithm was designed to be a "one-button" program, i.e., the user loads the chip into its position, sets the laser in the desired X-Y location, dials the desired nanopore size and pushes a "GO" button. A pseudo-code-representation of the algorithm is provided in the Supporting Information (Algorithm 1) along with an explanation of the variables and parameters with their notations. The algorithm consists of several main blocks to handle the four steps of the LD process (FIG. 16B): thinning, drilling, polishing and stabilization. During the thinning phase, the membrane is continuously irradiated by the laser, resulting in a rapid local thinning which can be monitored by a corresponding decrease in PL intensity. This step is concluded when the software determines the formation of a pore based on monitoring the ion current time derivative, $\delta I/\delta t$. Pore drilling and polishing involves software modulated laser pulsing, which uses feedback Ohmic (DC) measurements of the pore conductance. Finally, pore stabilization occurs with the laser fully blocked. The rationale for this strategy is based on the observation that abrupt changes in the laser intensity (or large dP/dt values) induce $SiN_x$ membrane charging or discharging, which in turn produce large jumps in the ion current followed by relaxation to a steady level. Therefore, to determine the unbiased Ohmic conductance, the software switches off the laser and waits for the current to stabilize.

Figure 16D:
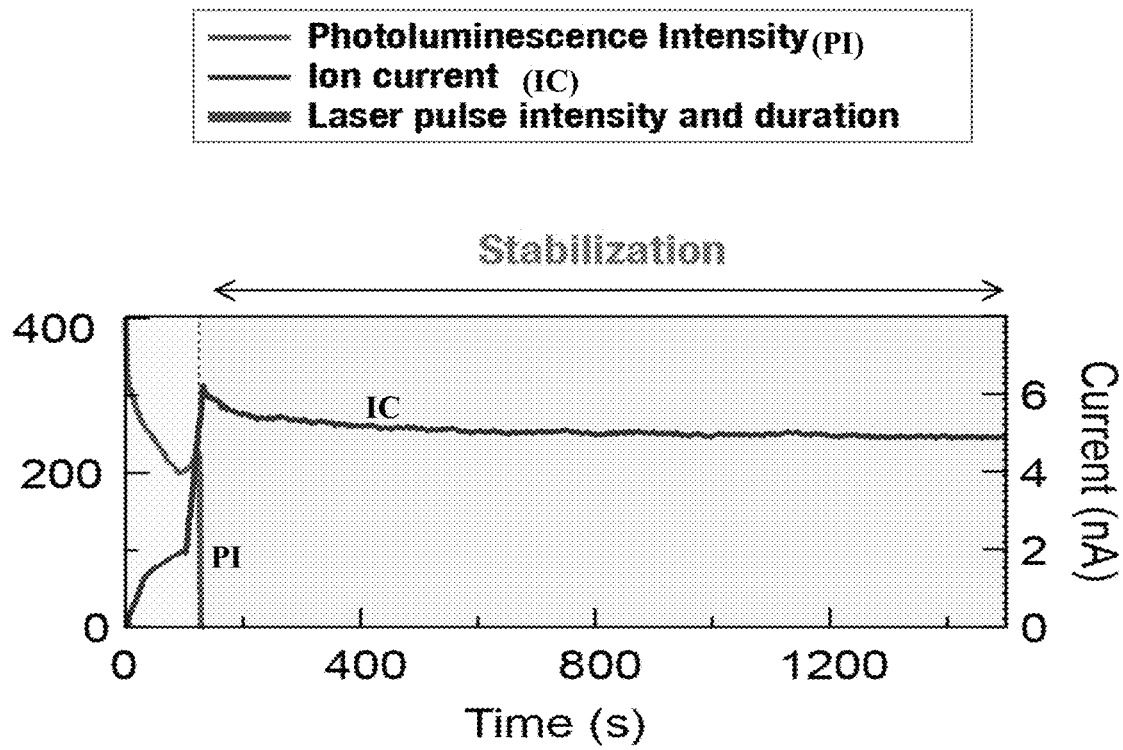

In FIG. 16C-D we provide a typical account of the entire ssNP drilling process, which commences after the autofocusing step is done. FIG. 16C shows time traces of the laser intensity (upper right), PL intensity (PL) and the nanopore ion current (C) during the first three steps of the process: membrane thinning, nanopore drilling and nanopore polishing. Gaps in the laser intensity plot represent the time intervals in which the software turns off the laser. In this example the user sets the target open pore current ($I_t$) to 6 nA (conductance of 20 nS). Once the NLDA determines that the set value has been reached, the system blocks the laser and begins the stabilization step, which typically lasts a few minutes. Typically, 2-3 minutes are sufficient for the stabilization, but in FIG. 16D we show a continuous current measurement of 20 minutes to illustrate its long-term stability.

The main complication in LD in comparison to classical control systems is that at present it is only possible to expand nanopores and not to controllably contract them. Therefore, the NLDA must converge to its target current on its first trial ("over-shoots" are not allowed). Importantly, maximum sensitivity in the measurement, required in the thinning step, is achieved by continuously calculating the ion current gradient ($\delta I/\delta t$) of a smoothed version of the current trace. The thinning step is terminated when the software detects the condition $\delta I/\delta t \geq \eta_{TH}$ where $\eta_{TH}$ is a pre-determined threshold $$\left(e.g., 4\frac{nA}{s}\right)$$

common to all chips in a given batch (≈200 units). This threshold, indicated in the inset of FIG. 2c by a red line, signals the initial formation of the nanopore and the first penetration of electrolytes through the membrane. We observe an abrupt positive change in $\delta I/\delta t$ values, used to trigger laser shutoff and the end of the thinning step. During the drilling and polishing steps, maximum accuracy is achieved by relying on DC Ohmic measurements of the pore conductance when the laser is off. Here we apply laser pulses of about 100-milliseconds, which are modulated by three parameters: i) the pulse duration $t_{pulse}$, ii) the pulse power P, and iii) the inter-pulse delay time $t_{IPD}$. These parameters are calculated in real-time based on the ion-current measurements during the previous inter-pulse delays. The methods section provides additional information regarding the laser pulsing control.

Example 9: Deterministic and Rapid Nanopore LD

Using the fabrication method implemented by the NLDA, we could efficiently and deterministically drill stable ssNPs with an average size of 4 nm, as estimated by our model (see below) and validated by translocation experiments. Once the NLDA was fully optimized, the mean drilling time was just a few minutes, equivalent or shorter than previous reports of laser-based ssNP drilling, and substantially shorter than other ssNP drilling methods when considering the deterministic size control feature. In FIG. 17, we present a summary of 42 NLDA experiments each resulting in a drilled ssNP. The overall drilling time (including thinning, drilling and polishing) are shown in FIG. 17A. We did not include the stabilization time as this is an optional step that is often used with all other nanopore drilling strategies. The histogram is fitted using a normal distribution, with a mean value of 84 s and a STD of 42 s. The large STD in the drilling time can be attributed to the fact that each of the chips was manually assembled in the holder, and in addition each chip was selected from a different area in the wafer where slight variances in membrane thickness and Si/N composition exist, both of which impact the drilling time of the NLDA.

The boxplot in FIG. 17B displays the NLDA performance for different set target values $I_t$. Each of the boxes represent a different target for a group of experiments with respect to the actual final open pore current obtained, $I_{result}$. Each box is statistically separated from its neighbors, where overlapping is found only outside of the majorities. In addition, it demonstrates the process uniformity, where the behavior is similar, regardless of the fabricated nanopore size. The gray line is linear fit between the $I_{result}$ and $I_t$ having a slope=1.026±0.062. FIG. 17C displays the overall performances (as in FIG. 17A), showing the deviation of $I_{result}$ from $I_t$. As can be seen, based on the statistics of 42 nanopores drilled using a range of $I_t$ from 2 nm to 8 nA, a mean error of 0.2 nA (equivalent to ~0.67 nS) between the set value and the stabilized open pore current is obtained. This corresponds to a less than 5% mean error in achieving the setpoint current, or a roughly 2.5% error in the corresponding calculated ssNP diameter. Three typical ssNP LD traces are shown in FIG. 3c having an $I_t$ of 3 nA, 4 nA and 6 nA from top to bottom, respectively (all measured with V=300 mV). Notably, NLDA achieved the desired levels within 26 s to 86 s, before the pores were left for a few minutes of stabilization.

Example 10: Investigating the NLDA-Fabricated ssNP 3D Shape

After developing the NLDA for rapid and deterministic ssNP fabrication, we asked whether the special pore form-factor produced by the Gaussian laser beam has an impact on the nanopore's performance. Nanopore conductance is generally affected by both the in-pore resistance and the access resistance, modeled according to:

$$G = \frac{1}{V} = \left(\frac{4h_{eff}}{\pi d^2} + \frac{1}{d}\right)^{-1} \sigma, \quad (1)$$

where $h_{eff}$ is the membrane effective thickness, d is the nanopore diameter and a is the solution specific conductivity. Equation 1 represents a simplified approximation of the physical ssNP shape as a perfect cylinder and ignores additional effects such surface roughness and surface charge. Nevertheless, it is practically useful in providing an idea of the ssNP dimensions based on the measured conductance and has often been used to approximate the ssNP diameter. Importantly, however, not only the Ohmic characteristics of the nanopore determine its ability to efficiently sense biomolecules. In addition to the pore conductance, the electrical field distribution outside the pore $\vec{E}(z,r)$ affects the rate at which charged biomolecules are transported to the nanopore prior to their entry, hence playing an important role in the functionality of the device. Therefore, when determining the ssNP performance, it is essential to consider not only its diameter and the membrane thickness, but also its physical shape beyond the narrowest constriction.

Previous investigations of TEM-drilled nanopores suggested an approximately hour-glass form factor with a cone angle of roughly 30° and an effective thickness of roughly ⅓ of the membrane nominal thickness. For LD ssNPs, TEM based thickness profiling of the membrane demonstrated that the membrane thinning follows a Gaussian profile having the dimensions of the tightly focused laser beam. As photo-induced etching may occur symmetrically on both sides of the membrane, it is likely that the actual nano-well shape formed by the laser includes two back-to-back Gaussian "bowls" connected by the nanopore. This structure resembles to some extent the "hourglass" shape of nanopores created by the TEM drilling, except with a much wider opening.

To gain deeper insight of the LD ssNP properties, we performed numerical simulations using COMSOL Multiphysics (COMSOL, Inc.) of the electrical potential V(z,r) and electrical field via the ion current density vector $\vec{J}(z,r)=\sigma\vec{E}(z,r)$, as shown in FIG. 18A and FIG. 25. To provide context to our simulations, we compared it with a naïve (perfect cylinder) and hourglass nanopore of similar dimensions, as indicated. Line profiles of the z-components of $\vec{J}(z,r)$ suggest that the LD ssNP electrical field decays away from the ssNP (z axis and r=0) in a similar fashion as the TEM drilled ssNP (hourglass), as shown on the leftmost panel on FIG. 18B. However, in the pore vicinity the electrical field z-component extends to a much broader range as compared with the other form factors, as shown in FIG. 18B, suggesting potentially better biomolecule focusing and capture. We note, however, that an experimental confirmation of this observation would require extensive investigation of the precise nanopore form factors using TEM tomography or alternative approaches that are beyond the scope of this study.

The numerical simulations of the ion current density may be used to evaluate the accuracy of the simplified theoretical description presented in equation 1, for each of the nanopore form factors (cylinder, hourglass and Gaussian). To that end we used the numerical simulations to calculate the open pore current (see Supporting Information section IV) and divided by the full potential drop to obtain the conductance G(d) as a function of the pore diameter. Our results are presented in FIG. 18C with the axes inverted to show d(G), as the nanopore conductance is readily measured in experiments whereas its diameter is not as easily determined. Using equation 1, we globally fit the three data sets, fixing $h_{eff}$ of the naïve (a perfect cylinder) pore to the membrane nominal thickness (50 nm) and forcing a single value for the specific solution conductance. From the fits we obtained $\sigma$=26.86±0.54 (Ω nm)$^{-1}$; $h_{eff}$(HG)=28.6±0.8 nm; $h_{eff}$(LD) =17.5±0.5 nm. Returning to FIG. 17, we added on top of the numerically simulated LD pore the 42 experimentally measured NLDA nanopores. This allowed us to estimate the pore diameter from the measured conductance subject to the assumptions made in the numerical simulation. As shown in the FIG. 18B bottom panel, the nanopore sizes were between 2.5 to 5 nm, within the expected range based on the protein translocation results.

Example 11: Translocation Analysis of SDS-Denatured Carbonic Anhydrase Proteins

To validate the ability of the NLDA to fabricate functional ssNPs, we measured SDS-denatured Carbonic Anhydrase II (CA2) translocations right after LD. CA2 is a 260 amino-acid-long protein (pI 6.87), which is negatively charged in the alkaline LD buffer. The protein was added to the cis chamber of the setup with a final concentration of 10 nM. Importantly, to maintain the proteins' denatured state, translocations were performed in the presence of SDS (see Methods section for more details). FIG. 19A displays a characteristic NLDA trace achieving a stable 13 nS ssNP (about 4 nA at 300 mV), in less than 30 s. According to the LD conductance simulations (FIG. 18C) this corresponds to a ~3.5 nm ssNP diameter. After ~11 s of membrane thinning the program started the pore polishing terminating the process after 7 laser "pulses" when achieving the target open-pore current ($I_f$=4 nA). Inset displays bright light images showing the PL spot before pore formation (left) and the same area after pore formation (laser off). The nanopore measured I-V curve is shown in FIG. 26. As in the NLDA process, the next steps take place under voltage of V=300 mV as well. Right after the ssNP stabilized, we added the protein and SDS sample to the Cis chamber and recorded translocation events for about 20 minutes. We noted that upon analytes addition the open-pore current ($I_O$) slightly increased to about 4.6 nA and remained stable throughout the experiment with $I_O$=4.65±0.05 nA (mean±STD). FIG. 19B top panel displays $I_O$ measured in between the events. The bottom panel in FIG. 19B displays an event diagram (the fractional current $I_B$ versus events dwell time $t_D$ shown in logarithmic scale) consisting of 358 translocation events plotted on top of a heat map representing the 2D histogram density. As can be seen, we obtained relatively deep and long translocation dwell times, suggesting that the nanopore is only slightly larger than the SDS denatured polypeptide chain. Histograms of the fractional current blockage and dwell-time yield mean values of 0.43±0.04 and 900±95 µs, respectively (FIG. 27). These values qualitatively agree with a nominal thickness of the SDS denatured polypeptide chain of about 2 nm. Notably, since the CA2 pI is ~6.87, when using our pH 10 buffer we expected to obtain a beneficial negative charge that can assist with drawing the proteins from the cis reservoir to the trans one, according to the applied electric field. The relatively long measured dwell time of the proteins may suggest a relatively small charge/mass ratio, and/or preferable interactions with the ssNP wall, presumably mediated by the SDS molecules.

Example 12: Photo-Chemical Etching Mechanism

The ability to consistently fabricate large numbers of ssNPs in an unattended manner facilitates further investigation into the photo-chemical laser etching process. Our previous studies indicated that low-intensity/time-efficient LD requires Si-rich $SiN_x$ membranes and alkaline conditions (i.e., pH 10). When the laser energy is greater than the material bandgap energy, the laser irradiation generates electron-hole pairs within the $SiN_x$ surface and charge transfer at the liquid-solid interface. This surface charging catalyzes a rapid photo-chemical etching of the membrane at the beam center. The etching progresses into the membrane resulting in a shape that roughly replicates the Gaussian beam profile. Importantly, however, as the thinning process progresses, the interfacial charges from the two sides of the membrane may gradually repel each other, creating a charge depletion zone. The localized charge depletion zone slows down the etching kinetics, prior to the eventual formation of the nanopore, as schematically depicted in FIG. 20A.

To check this hypothesis, we analyzed the photoluminescence time traces during the membrane thinning stage of 15 LD trials, as defined by the NLDA. We observed a characteristic rapid reduction in PL intensity, followed by a slower decay over longer times (FIG. 20B). We empirically fitted the processes by a sum of two decaying exponential functions, which yielded two clearly distinct rate constants ($\lambda_1$=0.343±0.008 and $\lambda_2$=60.0±0.7×10$^{-4}$ s$^{-1}$ differing by more than two orders of magnitude (additional examples for such traces are found in FIG. 28). Upon the creation of a nanopore (signaled by the ion current jump) the membrane thinning step is terminated and the nanopore expansion/polishing starts. We checked if nanopore expansion proceeds without the laser by keeping the laser off while monitoring the ion current flow under a constant applied voltage (300 mV) typically used in translocation measurements. Over the course of >10 minutes we did not observe any change in the ion current (n=3), hence ruling out the possibility of purely electrically driven pore expansion. In contrast, when short laser pulses are applied, we observe larger spikes in the measured ion current. Presumably, the localized laser induces the creation of electron-hole pairs but the different mobilities of two carriers generate a local electromotive force (EMF) in the radial direction (Dember effect) that acts as a battery leading to the observed current spikes. Moreover, the local and transient charging of the nanopore interfaces facilitates the process of photo-chemical etching of the $SiN_x$ and the controlled enlargement of the nanopore, which would be otherwise too abrupt to finely control.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method of thinning a membrane comprising a first layer comprising an index of refraction of greater than 2.0, the method comprising shining focused light on a spot on said first layer, thereby thinning said membrane.

2. The method of claim 1, wherein said focused light is laser light and said laser light is at a wavelength of between 300 and 600 nm.

3. The method of claim 1, wherein said light is at least one of:
   a. within the purple, blue or green spectrum;
   b. comprising an intensity of at least 100 µW;
   c. comprising an intensity of between 1 and 45 mW; and
   d. continuous-wave laser light or pulsed laser light.

4. The method of claim 1, wherein said first layer
   a. comprises silicon nitride ($SiN_x$);
   b. comprises $SiN_x$ comprising an average silicon to nitrogen ratio of greater than 0.75; or
   c. a combination thereof.

5. The method of claim 1, wherein said membrane is a freely standing membrane, covered by an aqueous solution on both sides.

6. The method of claim 1, further comprising measuring photoluminescent (PL) intensity from said spot on said membrane, wherein said PL intensity is inversely proportional to the thickness of said spot on said membrane, and said thinning is halted at a desired thickness based on a measured PL intensity.

7. The method of claim 1, wherein said thinning comprises
   a. forming a nanopore through said membrane; or
   b. widening a pore through said membrane.

8. The method of claim 7, wherein said membrane is immersed in an aqueous solution and the method further comprising measuring ionic current through said membrane; and wherein an increase in ionic current through said membrane indicates said pore has been formed in said membrane or if said pore is present said increase is proportional to a widening of said pore.

9. The method of claim 7, wherein said method produces a pore of a predetermined size and comprises
   a.
      i. shining a laser light on a spot on said membrane while monitoring ion current from a first side of said membrane to a second side of said membrane;

ii. stopping said laser light when said ion current begins increasing thereby generating a pore through said membrane;
iii. shining a laser light on said pore for a first duration and at a first intensity;
iv. stopping said laser light and measuring at least one of electrical resistance and current through said pore;
v. shining a laser light on said pore for a second duration and at a second intensity wherein said second duration and second intensity are based on said measured at least one of electrical resistance and current; and
vi. repeating steps iv and y until said measured electrical resistance and/or current indicates said pore is at said predetermined size; or b.
i. shining a continuous wave focused laser light on a spot on said membrane while monitoring ion current from a first side of said membrane to a second side of said membrane;
ii. stopping said continuous wave focused laser light when said ion current begins increasing thereby generating a pore through said membrane; and
iii. shining pulsed laser light on said pore until said pore reaches said predetermined size.

10. The method of claim 9, wherein at least one of
a. said second intensity, said second duration or both are increased as compared to said first intensity if said measured electrical current indicates an effectiveness ratio above a predetermined threshold and wherein said effectiveness ratio is determined by $$\frac{\mu^{N-1}}{I_N}$$

wherein $\mu^{N-1}$ is the mean current of previous measurements and $I_N$ is said measured electrical current;
b. said second intensity and said second duration are the same as said first intensity and said first duration if said effectiveness ratio is at or below said predetermined threshold, but a significance parameter is at or below a predetermined threshold, wherein said significance parameter is $I_N - \mu^{N-1}$; and
c. said second intensity, said second duration or both are decreased as compared to said first intensity if said measured electrical current indicates said effectiveness ratio is at or below a predetermined threshold and said significance parameter is above a predetermined threshold.

11. A thinned membrane produced by a method of claim 1.

12. The method of claim 1, wherein said membrane comprises a second layer refractory to thinning by said focused light when not layered on said first layer, wherein said second layer is a dielectric layer or a layer of metal oxide, and wherein said second layer is layered onto said first layer.

13. The method of claim 1, wherein said membrane comprises a second layer comprising metal oxide and wherein said metal oxide is titanium oxide (TiO2), aluminum oxide (AlO2) or hafnium oxide (HfO2).

14. The method of claim 1, wherein said membrane does not comprise a thickness of less than 20 nm.

15. The method of claim 1, wherein said membrane is immersed in ultrapure water or salt buffer comprising an alkaline pH.

16. The method of claim 1, wherein said membrane is at room temperature and pressure.

17. The method of claim 1, wherein said first layer comprises an index of refraction of greater than 2.20.

* * * * *